US012788213B2

(12) United States Patent
Goto

(10) Patent No.: US 12,788,213 B2
(45) Date of Patent: Nov. 10, 2026

(54) MEDICAL SUPPORT DEVICE, ENDOSCOPE APPARATUS, MEDICAL SUPPORT METHOD, AND PROGRAM

(71) Applicant: FUJIFILM Corporation, Tokyo (JP)

(72) Inventor: Misaki Goto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 166 days.

(21) Appl. No.: 18/779,067

(22) Filed: Jul. 21, 2024

(65) Prior Publication Data

US 2025/0049291 A1 Feb. 13, 2025

(30) Foreign Application Priority Data

Aug. 10, 2023 (JP) ................................ 2023-131411

(51) Int. Cl.

| | |
|---|---|
| ***A61B 1/00*** | (2006.01) |
| ***A61B 1/05*** | (2006.01) |
| ***A61B 1/31*** | (2006.01) |
| ***G06T 7/70*** | (2017.01) |
| ***G06V 10/70*** | (2022.01) |

(52) U.S. Cl.

CPC .. *A61B 1/000094* (2022.02); *A61B 1/000096* (2022.02); *A61B 1/00045* (2013.01); *G06T 7/70* (2017.01); *A61B 1/05* (2013.01); *A61B 1/31* (2013.01); *G06T 2207/10068* (2013.01); *G06T 2207/30096* (2013.01); *G06V 10/70* (2022.01); *G06V 2201/03* (2022.01)

(58) Field of Classification Search

CPC ........ A61B 1/000094; A61B 1/000096; A61B 1/00045; A61B 1/05; A61B 1/31; A61B 1/0005; G06T 7/70; G06T 2207/10068; G06T 2207/30096; G06V 10/70; G06V 2201/03

See application file for complete search history.

(56) References Cited

U.S. PATENT DOCUMENTS

| | | | | |
|---|---|---|---|---|
| 2019/0037201 | A1* | 1/2019 | Serizawa | G02B 21/365 |
| 2020/0037856 | A1* | 2/2020 | Watanabe | A61B 1/00045 |
| 2020/0170485 | A1 | 6/2020 | Takahashi et al. | |
| 2021/0022586 | A1 | 1/2021 | Mori et al. | |
| 2021/0110915 | A1* | 4/2021 | Oosake | G09G 5/14 |
| 2021/0153722 | A1 | 5/2021 | Karino | |

(Continued)

FOREIGN PATENT DOCUMENTS

| | | |
|---|---|---|
| JP | 2019180966 | 10/2019 |
| JP | 7225417 | 2/2023 |

(Continued)

*Primary Examiner* — Anhtuan T Nguyen
*Assistant Examiner* — Li-Ting Song
(74) *Attorney, Agent, or Firm* — JCIPRNET

(57) ABSTRACT

A medical support device includes a processor. The processor acquires an image obtained by imaging an inside of a body with a camera. The processor outputs screen generation information used for generation of a screen on which the image and presence position information for specifying a presence position of an in-body feature region recognized by executing an object recognition process using the image on an outside of the image are displayed. A display position of the presence position information with respect to the image in the screen is changed according to a change in a positional relationship between the camera and the in-body feature region.

22 Claims, 26 Drawing Sheets

(56) References Cited

U.S. PATENT DOCUMENTS

| | | | | |
|---|---|---|---|---|
| 2021/0251470 | A1* | 8/2021 | Kimura | G06T 7/20 |
| 2021/0327067 | A1* | 10/2021 | Hayami | G06T 7/0014 |
| 2022/0151467 | A1 | 5/2022 | Meguro | |
| 2022/0172827 | A1 | 6/2022 | Endo | |
| 2022/0277445 | A1* | 9/2022 | Choi | G16H 50/20 |
| 2025/0049291 | A1* | 2/2025 | Goto | A61B 1/00045 |

FOREIGN PATENT DOCUMENTS

| | | |
|---|---|---|
| JP | 7256275 | 4/2023 |
| WO | 2018216618 | 11/2018 |
| WO | 2020039968 | 2/2020 |

* cited by examiner

MEDICAL SUPPORT DEVICE, ENDOSCOPE APPARATUS, MEDICAL SUPPORT METHOD, AND PROGRAM

CROSS-REFERENCE TO RELATED APPLICATIONS

This application claims priority under 35 USC 119 from Japanese Patent Application No. 2023-131411 filed on Aug. 10, 2023, the disclosure of which is incorporated by reference herein.

BACKGROUND

1. Technical Field

The present disclosure relates to a medical support device, an endoscope apparatus, a medical support method, and a program.

2. Related Art

WO2018/216618A discloses an information processing apparatus including detection means, determination means, and notification means. In the information processing apparatus disclosed in WO2018/216618A, the detection means detects an abnormal region inside a body from a moving image obtained by imaging the inside of the body. The determination means determines whether or not a predetermined condition is satisfied in a case where the abnormal region is detected from within a predetermined range of a first moving image frame of the moving image and the abnormal region is not detected from within a predetermined range of a second moving image frame of the moving image, which is generated after the first moving image frame. The notification means performs a first notification in a case where it is determined that the predetermined condition is not satisfied.

JP2019-180966A discloses an endoscope observation support device that supports observation of a luminal organ by an endoscope. The endoscope observation support device disclosed in JP2019-180966A comprises an image information acquisition unit, a lesion information acquisition unit, a determination unit, and a notification unit. In the endoscope observation support device disclosed in JP2019-180966A, the image information acquisition unit acquires a captured image of the luminal organ imaged by the endoscope and displays the captured image on a display unit. The lesion information acquisition unit detects a predetermined lesion based on the captured image and acquires lesion information related to the lesion. The determination unit tracks the lesion based on the captured image and the lesion information, and determines whether or not the lesion has disappeared from the captured image. The notification unit issues a notification of a determination result in a case where the determination unit determines that the lesion has disappeared from the captured image.

JP7256275B discloses an endoscope system comprising an endoscope, an endoscope control device, and a medical image processing device. In the endoscope system disclosed in JP7256275B, the medical image processing device comprises an image acquisition unit, a region-of-interest detection unit, an unobserved condition determination unit, an unobserved image storage unit, and a display signal transmission unit. The image acquisition unit acquires an observation image of a subject. The region-of-interest detection unit detects a region of interest from a frame image constituting the observation image. The unobserved condition determination unit determines whether or not an unobserved condition indicating that the frame image in which the region of interest is detected includes the region of interest overlooked by a user is satisfied. The unobserved image storage unit stores an unobserved image that satisfies the unobserved condition. The display signal transmission unit transmits a first display signal representing the observation image and a second display signal representing the unobserved image to a display device. The region-of-interest detection unit determines an identity between the region of interest of the unobserved image and the region of interest of the observation image. The display signal transmission unit stops the transmission of the second display signal in a case where a determination result that the region of interest of the unobserved image and the region of interest of the observation image are the same is obtained.

In the endoscope system disclosed in JP7256275B, the unobserved condition determination unit determines that the unobserved condition is satisfied in a case where the number of frame images including the same region of interest is equal to or less than a prescribed number within a prescribed period, determines that the unobserved condition is satisfied in a case where a change amount between the frame images is equal to or greater than a prescribed threshold value, or determines that the unobserved condition is satisfied in a case where the same region of interest remains in any region in the screen within a prescribed period.

WO2020/039968A discloses a medical image processing system comprising a medical image acquisition unit, a region-of-interest detection unit, and a display control unit. In the medical image processing system disclosed in WO2020/039968A, the medical image acquisition unit acquires a medical image obtained by imaging an observation target. The region-of-interest detection unit detects a region of interest from the medical image. The display control unit displays a detection result of the region of interest on a display unit in a display aspect that differs depending on at least a detection position of the region of interest.

JP7225417B discloses a medical image processing system comprising an image acquisition unit that acquires a medical image, a display unit that displays the medical image, a region-of-interest detection unit that detects a region of interest from the medical image, a movement amount estimation unit that estimates a movement amount of an apparatus that captures the medical image based on the medical image, and a notification unit that issues a notification of detection of the region of interest by emphasizing the region of interest in the medical image displayed on the display unit in a case where the region of interest is detected and that changes a degree of emphasis of the region of interest according to the movement amount estimated by the movement amount estimation unit after the notification. Here, the notification unit may increase the degree of emphasis of the region of interest in a case where the movement amount estimated by the movement amount estimation unit is equal to or greater than a threshold value after the notification of the detection of the region of interest, or may decrease the degree of emphasis of the region of interest or may turn off the emphasis of the region of interest in a case where the movement amount estimated by the movement amount estimation unit is less than the threshold value after the notification of the detection of the region of interest. In addition, the notification unit surrounds the region of interest with a border to emphasize the region of interest in the medical image displayed on the display unit.

Here, the notification unit changes at least one of a thickness, a line type, a color, a shape, a blinking degree, or a brightness of the border to change the degree of emphasis of the region of interest.

In the medical image processing system disclosed in JP7225417B, the notification unit issues a sound to notify of the detection of the region of interest in a case where the region of interest is detected, and changes a volume of the sound according to the movement amount estimated by the movement amount estimation unit after the notification. Here, the notification unit increases the volume of the sound in a case where the movement amount estimated by the movement amount estimation unit is equal to or greater than the threshold value after the notification of the detection of the region of interest, or decreases the volume of the sound or turns off the sound in a case where the movement amount estimated by the movement amount estimation unit is less than the threshold value after the notification of the detection of the region of interest.

SUMMARY

One embodiment according to the present disclosure provides a medical support device, an endoscope apparatus, a medical support method, and a program with which a user can ascertain a presence position of an in-body feature region outside an image obtained by imaging an inside of a body with a camera even in a case where a positional relationship between the camera and the in-body feature region is changed.

A first aspect according to the present disclosure is a medical support device comprising a processor, in which the processor is configured to: acquire an image obtained by imaging an inside of a body with a camera; and output screen generation information used for generation of a screen on which the image and presence position information for specifying a presence position of an in-body feature region recognized by executing an object recognition process using the image on an outside of the image are displayed, and a display position of the presence position information with respect to the image in the screen is changed according to a change in a positional relationship between the camera and the in-body feature region.

A second aspect according to the present disclosure is the medical support device according to the first aspect, in which the change is caused by an operation of the camera and/or a body movement in the inside of the body.

A third aspect according to the present disclosure is the medical support device according to the second aspect, in which the display position is changed according to the change to follow the operation and/or the body movement.

A fourth aspect according to the present disclosure is the medical support device according to any one of the first to third aspects, in which a display aspect of the presence position information is changed according to a feature of the change.

A fifth aspect according to the present disclosure is the medical support device according to the fourth aspect, in which the feature includes a speed of the change, an amount of the change, and/or a direction of the change.

A sixth aspect according to the present disclosure is the medical support device according to any one of the first to fifth aspects, in which the presence position information includes within-angle-of-view position information for specifying, on the outside, the presence position in a case where the in-body feature region is within an angle of view of the camera, and out-of-angle-of-view position information for specifying, on the outside, the presence position in a case where the in-body feature region is out of the angle of view, the within-angle-of-view position information is displayed on the screen in a case where the in-body feature region is within the angle of view, and the out-of-angle-of-view position information is displayed on the screen in a case where the in-body feature region is out of the angle of view.

A seventh aspect according to the present disclosure is the medical support device according to any one of the first to sixth aspects, in which the presence position information includes out-of-angle-of-view position information for specifying, on the outside, the presence position in a case where the in-body feature region is out of an angle of view of the camera, the out-of-angle-of-view position information is displayed on the screen in a case where the in-body feature region is out of the angle of view, and a display aspect of the out-of-angle-of-view position information is changed according to a feature of the change.

An eighth aspect according to the present disclosure is the medical support device according to the seventh aspect, in which the display aspect includes presence or absence of display, a display intensity, a display time, and/or a speed of changing the display intensity.

A ninth aspect according to the present disclosure is the medical support device according to any one of the first to eighth aspects, in which the presence position information includes out-of-angle-of-view position information for specifying, on the outside, the presence position in a case where the in-body feature region is out of an angle of view of the camera, the out-of-angle-of-view position information is displayed on the screen in a case where the in-body feature region is out of the angle of view, the in-body feature region is a lesion, and a display aspect of the out-of-angle-of-view position information is changed according to a malignancy grade of the lesion, a site where the lesion is present, a kind of the lesion, a type of the lesion, a form of the lesion, an aspect of a boundary between the lesion and a periphery of the lesion, and/or an adhesion aspect of mucus of the lesion.

A tenth aspect according to the present disclosure is the medical support device according to any one of the first to ninth aspects, in which the presence position information includes out-of-angle-of-view position information for specifying, on the outside, the presence position in a case where the in-body feature region is out of an angle of view of the camera, and the out-of-angle-of-view position information is displayed on the screen on a condition that the in-body feature region is out of the angle of view.

An eleventh aspect according to the present disclosure is the medical support device according to the tenth aspect, in which display of the out-of-angle-of-view position information on the screen in a case where a within-angle-of-view time during which the in-body feature region is within the angle of view is less than a certain time is more emphasized than display of the out-of-angle-of-view position information on the screen in a case where the within-angle-of-view time is equal to or longer than the certain time.

A twelfth aspect according to the present disclosure is the medical support device according to any one of the first to ninth aspects, in which the presence position information includes out-of-angle-of-view position information for specifying, on the outside, the presence position in a case where the in-body feature region is out of an angle of view of the camera, and the out-of-angle-of-view position information is displayed on the screen on a condition that a predetermined time has elapsed after the in-body feature region is out of the angle of view.

A thirteenth aspect according to the present disclosure is the medical support device according to any one of the first to twelfth aspects, in which the presence position information includes out-of-angle-of-view position information for specifying, on the outside, the presence position in a case where the in-body feature region is out of an angle of view of the camera, and the out-of-angle-of-view position information is displayed on the screen on a condition that the in-body feature region is out of the angle of view and a degree of the change exceeds a predetermined degree.

A fourteenth aspect according to the present disclosure is the medical support device according to any one of the first to thirteenth aspects, in which the presence position information includes out-of-angle-of-view position information for specifying, on the outside, the presence position in a case where the in-body feature region is out of an angle of view of the camera, the out-of-angle-of-view position information is displayed on the screen in a case where the in-body feature region is out of the angle of view, and display of the out-of-angle-of-view position information on the screen in a case where a frequency at which the in-body feature region enters and exits the angle of view exceeds a predetermined frequency within a unit time is more emphasized than display of the out-of-angle-of-view position information on the screen in a case where the frequency is equal to or less than the predetermined frequency.

A fifteenth aspect according to the present disclosure is the medical support device according to any one of the first to fourteenth aspects, in which the screen generation information includes the image and position indication information for indicating a position of the presence position information in the screen, and the position indication information is updated according to the change.

A sixteenth aspect according to the present disclosure is the medical support device according to the fifteenth aspect, in which the screen generation information includes the image, the presence position information, and the position indication information.

A seventeenth aspect according to the present disclosure is the medical support device according to any one of the first to sixteenth aspects, in which the object recognition process includes a process of recognizing the in-body feature region based on the image by using AI.

An eighteenth aspect according to the present disclosure is the medical support device according to any one of the first to the seventeenth aspects, in which the in-body feature region is a lesion.

A nineteenth aspect according to the present disclosure is the medical support device according to any one of the first to eighteenth aspects, in which the image is included in a plurality of frames obtained in time series by imaging the inside of the body with the camera, and the processor is configured to: specify the change based on the plurality of frames; and change the display position according to the specified change.

A twentieth aspect according to the present disclosure is the medical support device according to any one of the first to nineteenth aspects, in which the processor is configured to: specify the change based on a detection result by a sensor capable of detecting a behavior of the camera in the inside of the body; and change the display position according to the specified change.

A twenty-first aspect according to the present disclosure is a medical support device comprising a processor, in which the processor is configured to: acquire an image obtained by imaging an inside of a body with a camera; and output screen generation information used for generation of a screen on which a medical image generated based on the image and presence position information for specifying a presence position of an in-body feature region recognized by executing an object recognition process using the image on an outside of the image are displayed, and a display position of the presence position information with respect to the medical image in the screen is changed according to a change in a positional relationship between the camera and the in-body feature region.

A twenty-second aspect according to the present disclosure is an endoscope apparatus comprising: the medical support device according to any one of the first to twenty-first aspects; and the camera.

A twenty-third aspect according to the present disclosure is a medical support method comprising: acquiring an image obtained by imaging an inside of a body with a camera; and outputting screen generation information used for generation of a screen on which the image and presence position information for specifying a presence position of an in-body feature region recognized by executing an object recognition process using the image on an outside of the image are displayed, in which a display position of the presence position information with respect to the image in the screen is changed according to a change in a positional relationship between the camera and the in-body feature region.

A twenty-fourth aspect according to the present disclosure is a program for causing a computer to execute a medical support process, the medical support process comprising: acquiring an image obtained by imaging an inside of a body with a camera; and outputting screen generation information used for generation of a screen on which the image and presence position information for specifying a presence position of an in-body feature region recognized by executing an object recognition process using the image on an outside of the image are displayed, in which a display position of the presence position information with respect to the image in the screen is changed according to a change in a positional relationship between the camera and the in-body feature region.

BRIEF DESCRIPTION OF THE DRAWINGS

Exemplary embodiments of the technology of the disclosure will be described in detail based on the following figures, wherein.

DETAILED DESCRIPTION

Figure 1:
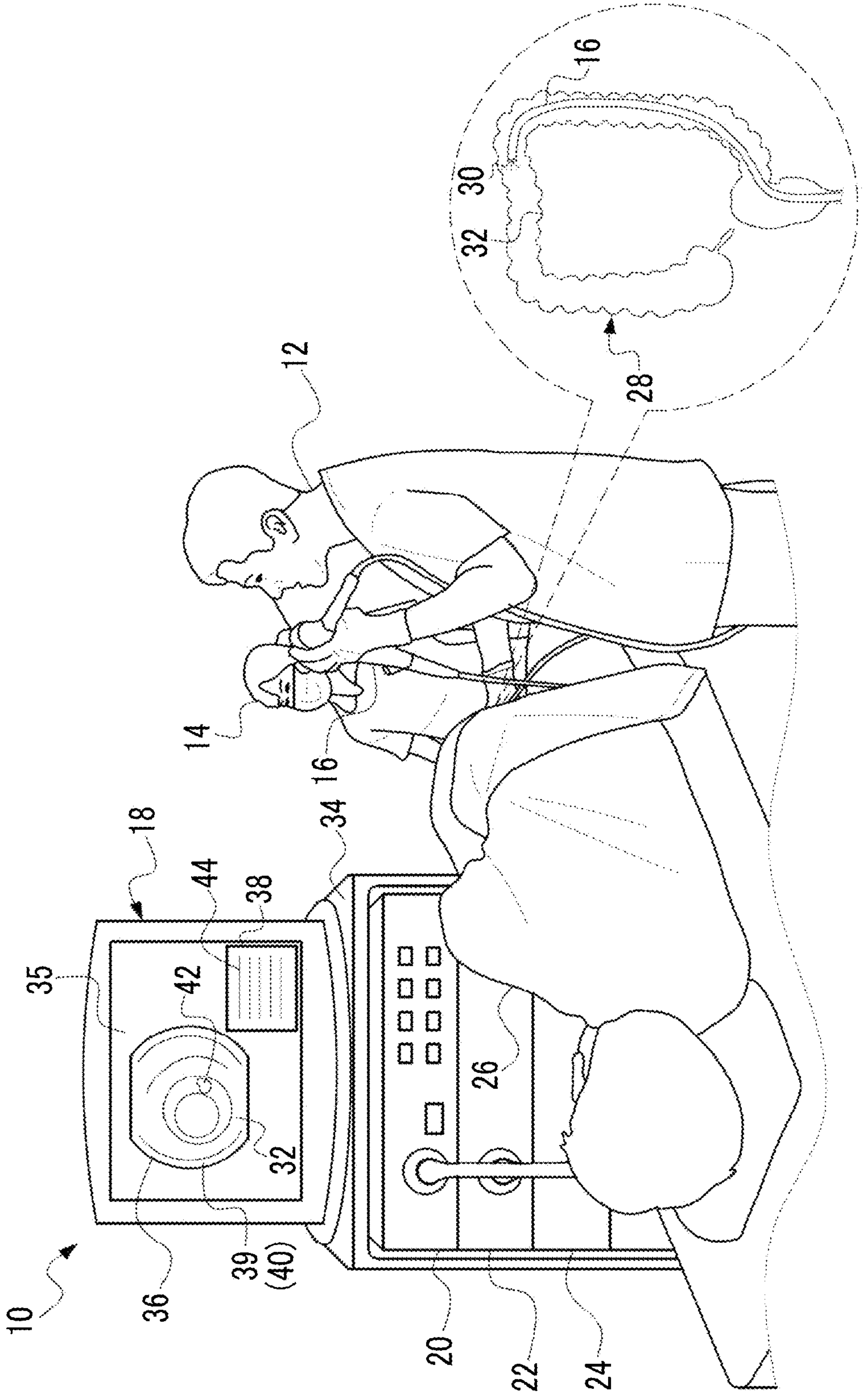
FIG. 1 is a conceptual diagram showing an example of an aspect in which an endoscope apparatus is used.

Hereinafter, examples of embodiments of a medical support device, an endoscope apparatus, a medical support method, and a program according to the present disclosure will be described with reference to the accompanying drawings.

First, the wording used in the following description will be described.

CPU is an abbreviation for a "central processing unit". GPU is an abbreviation for a "graphics processing unit". GPGPU is an abbreviation for "general-purpose computing on graphics processing units". APU is an abbreviation for an "accelerated processing unit". TPU is an abbreviation for a "tensor processing unit". RAM is an abbreviation for a "random access memory". NVM is an abbreviation for a "non-volatile memory". EEPROM is an abbreviation for an "electrically erasable programmable read-only memory". ASIC is an abbreviation for an "application specific integrated circuit". PLD is an abbreviation for a "programmable logic device". FPGA is an abbreviation for a "field-programmable gate array". SoC is an abbreviation for a "system-on-a-chip". SSD is an abbreviation for a "solid state drive". USB is an abbreviation for a "universal serial bus". HDD is an abbreviation for a "hard disk drive". EL is an abbreviation for "electro-luminescence". CMOS is an abbreviation for a "complementary metal oxide semiconductor". CCD is an abbreviation for a "charge coupled device". AI is an abbreviation for "artificial intelligence". BLI is an abbreviation for "blue light imaging". LCI is an abbreviation for "linked color imaging". I/F is an abbreviation for an "Interface". SSL stands for a "sessile serrated lesion". LAN is an abbreviation for a "local area network". WAN is an abbreviation for a "wide area network". 5G is an abbreviation for a "5th generation mobile communication system". FIFO is an abbreviation for "first in first out".

In the following description, a processor with a reference (hereinafter, simply referred to as a "processor") may be one computing device or a combination of a plurality of computing devices. In addition, the processor may be one type of a computing device or a combination of a plurality of types of computing devices. Examples of the computing device include a CPU, a GPU, a GPGPU, an APU, or a TPU.

In the following description, a memory with a reference is a memory (for example, a volatile memory) such as at least one RAM in which information is temporarily stored, and is used as a work memory by the processor.

In the following description, a storage with a reference is one or a plurality of non-volatile storage devices that store various programs, various parameters, and the like. Examples of the non-volatile storage device include a flash memory, a magnetic disk, or a magnetic tape. In addition, other examples of the storage include a cloud storage.

In the following embodiment, an external I/F with a reference transmits and receives various types of information between a plurality of devices connected to each other. Examples of the external I/F include a USB interface. A communication I/F including a communication processor, an antenna, and the like may be applied to the external I/F. The communication I/F performs communication between a plurality of computers. Examples of a communication standard applied to the communication I/F include a wireless communication standard including 5G, Wi-Fi (registered trademark), or Bluetooth (registered trademark).

In the following embodiments, "A and/or B" is synonymous with "at least one of A or B". That is, "A and/or B" means that it may be only A, only B, or a combination of A and B. In addition, in the present specification, in a case where three or more matters are associated and represented by "and/or", the same concept as "A and/or B" is applied.

FIG. 1 is a conceptual diagram showing an example of an aspect in which an endoscope apparatus 10 is used. As shown in FIG. 1, the endoscope apparatus 10 is used by a doctor 12 who is a user in an endoscopy. The endoscopy is assisted by a staff such as a nurse 14. In the present embodiment, the endoscope apparatus 10 is an example of an "endoscope apparatus" according to the present disclosure.

The endoscope apparatus 10 is connected to a communication device (not shown) in a communicable manner, and information obtained by the endoscope apparatus 10 is transmitted to the communication device. Examples of the communication device include a server and/or a client terminal (for example, a personal computer and/or a tablet terminal) that manage various types of information such as an electronic medical record. The communication device receives the information transmitted from the endoscope apparatus 10 and executes a process using the received information (for example, a process of storing the information in an electronic medical record or the like).

The endoscope apparatus 10 comprises an endoscope 16, a display device 18, a light source device 20, a control device 22, and a medical support device 24.

The endoscope apparatus 10 is a modality for performing medical care on a large intestine 28 included in a body of a subject 26 (for example, a patient) by using the endoscope 16. In the present embodiment, the large intestine 28 is a target to be observed by the doctor 12 in the endoscopy.

The endoscope 16 is used by the doctor 12 and is inserted into a luminal organ of the subject 26. In the present embodiment, the endoscope 16 is inserted into the large intestine 28 of the subject 26. The endoscope apparatus 10 causes the endoscope 16 inserted into the large intestine 28 of the subject 26 to image the inside of the large intestine 28 of the subject 26 and performs various medical treatments on the large intestine 28 as necessary.

The endoscope apparatus 10 acquires and outputs an image showing an aspect in the large intestine 28 by imaging the inside of the large intestine 28 of the subject 26. In the present embodiment, the endoscope apparatus 10 is an endoscope apparatus having an optical imaging function of capturing reflected light obtained by being reflected by an intestinal wall 32 of the large intestine 28 by irradiating the inside of the large intestine 28 with light 30.

Here, although the endoscopy of the large intestine 28 is illustrated, this is merely an example, and an endoscopy of a luminal organ such as an esophagus, a stomach, a duodenum, or a trachea may be adopted.

The light source device 20, the control device 22, and the medical support device 24 are installed on a wagon 34. A plurality of tables are provided in the wagon 34 along a vertical direction, and the medical support device 24, the control device 22, and the light source device 20 are installed from a lower table to an upper table. In addition, the display device 18 is installed on the uppermost table in the wagon 34.

The control device 22 controls the entire endoscope apparatus 10. The medical support device 24 performs various types of image processing on an image obtained by imaging the intestinal wall 32 with the endoscope 16 under the control of the control device 22.

The display device 18 displays various types of information including the image. Examples of the display device 18 include a liquid crystal display or an EL display. In addition, a tablet terminal with a display may be used instead of the display device 18 or together with the display device 18.

A screen 35 is displayed on the display device 18. The screen 35 includes a plurality of display regions. The plurality of display regions are arranged side by side in the screen 35. In the example shown in FIG. 1, a first display region 36 and a second display region 38 are shown as an example of the plurality of display regions. A size of the first display region 36 is larger than a size of the second display region 38. The first display region 36 is used as a main display region, and the second display region 38 is used as a sub-display region. A size relationship between the first display region 36 and the second display region 38 is not limited to this, and need only be a size relationship that fits on the screen 35.

An endoscopic moving image 39 is displayed in the first display region 36. The endoscopic moving image 39 is a moving image acquired by imaging the intestinal wall 32 with the endoscope 16 inside the large intestine 28 of the subject 26. In the example shown in FIG. 1, as an example of the endoscopic moving image 39, a moving image in which the intestinal wall 32 is shown is shown.

The intestinal wall 32 shown in the endoscopic moving image 39 includes an in-body feature region which is a region having a feature in the body (here, in the large intestine 28 as an example). Examples of the in-body feature region include a region of interest (that is, an observation target region) that is watched by the doctor 12. In the present embodiment, the doctor 12 can visually recognize an aspect of the intestinal wall 32 including the in-body feature region through the endoscopic moving image 39. Hereinafter, as an example of the in-body feature region, at least one lesion 42 (for example, in the example shown in FIG. 1, one lesion 42) will be described. In the present embodiment, the lesion 42 is an example of an "in-body feature region" and a "lesion" according to the present disclosure.

The lesion 42 has various types, and examples of the type of the lesion 42 include a neoplastic polyp and a non-neoplastic polyp. Examples of the type of the neoplastic polyp include an adenomatous polyp (for example, SSL). Examples of the type of the non-neoplastic polyp include a hamartomatous polyp, a hyperplastic polyp, and an inflammatory polyp. The types illustrated here are types assumed in advance as the types of the lesion 42 in a case where the endoscopy is performed on the large intestine 28, and the types of the lesion may be different depending on the organ on which the endoscopy is performed.

An image displayed in the first display region 36 is one frame 40 included in a moving image including a plurality of frames 40 (that is, a plurality of frames 40 along the time series) obtained in time series by imaging the intestinal wall 32 with the endoscope 16. That is, a plurality of frames 40 along the time series are displayed in the first display region 36 at a predetermined frame rate (for example, several tens of frames/second).

In the present embodiment, the frame 40 is an example of an "image" according to the present disclosure. In addition, in the present embodiment, the plurality of frames 40 obtained in time series by imaging the intestinal wall 32 with the endoscope 16 are an example of a "plurality of frames" according to the present disclosure.

Examples of the moving image displayed in the first display region 36 include a moving image of a live view method. The live view method is only an example, and a moving image which is temporarily stored in a memory or the like and then is displayed, such as a moving image of a post view method, may be employed. In addition, each frame included in a recording moving image stored in a memory or the like may be reproduced and displayed on the screen 35 (for example, the first display region 36) as the endoscopic moving image 39.

In the screen 35, the second display region 38 is present outside the first display region 36. In the example shown in FIG. 1, the second display region 38 is adjacent to the first display region 36 and is displayed on a right side in the screen 35 in a front view. A display position of the second display region 38 may be any position different from the first display region 36. However, the second display region 38 is preferably displayed at a position comparable to the endoscopic moving image 39 displayed in the first display region 36.

Medical information 44, which is information related to a medical care, is displayed in the second display region 38. Examples of the medical information 44 include information for assisting in a medical judgment or the like by the doctor 12. First examples of the information for assisting in the medical judgment or the like by the doctor 12 include various types of visible information (for example, a name, a gender, a medication, a medical history, a blood pressure value, and/or a heart rate) regarding the subject 26 into which the endoscope 16 is inserted. In addition, second examples of the information for assisting in the medical judgment or the like by the doctor 12 include visible information such as a text and/or an image (for example, a feature amount map and/or information obtained by processing the feature amount map) obtained by performing processing using AI on the endoscopic moving image 39.

Figure 2:
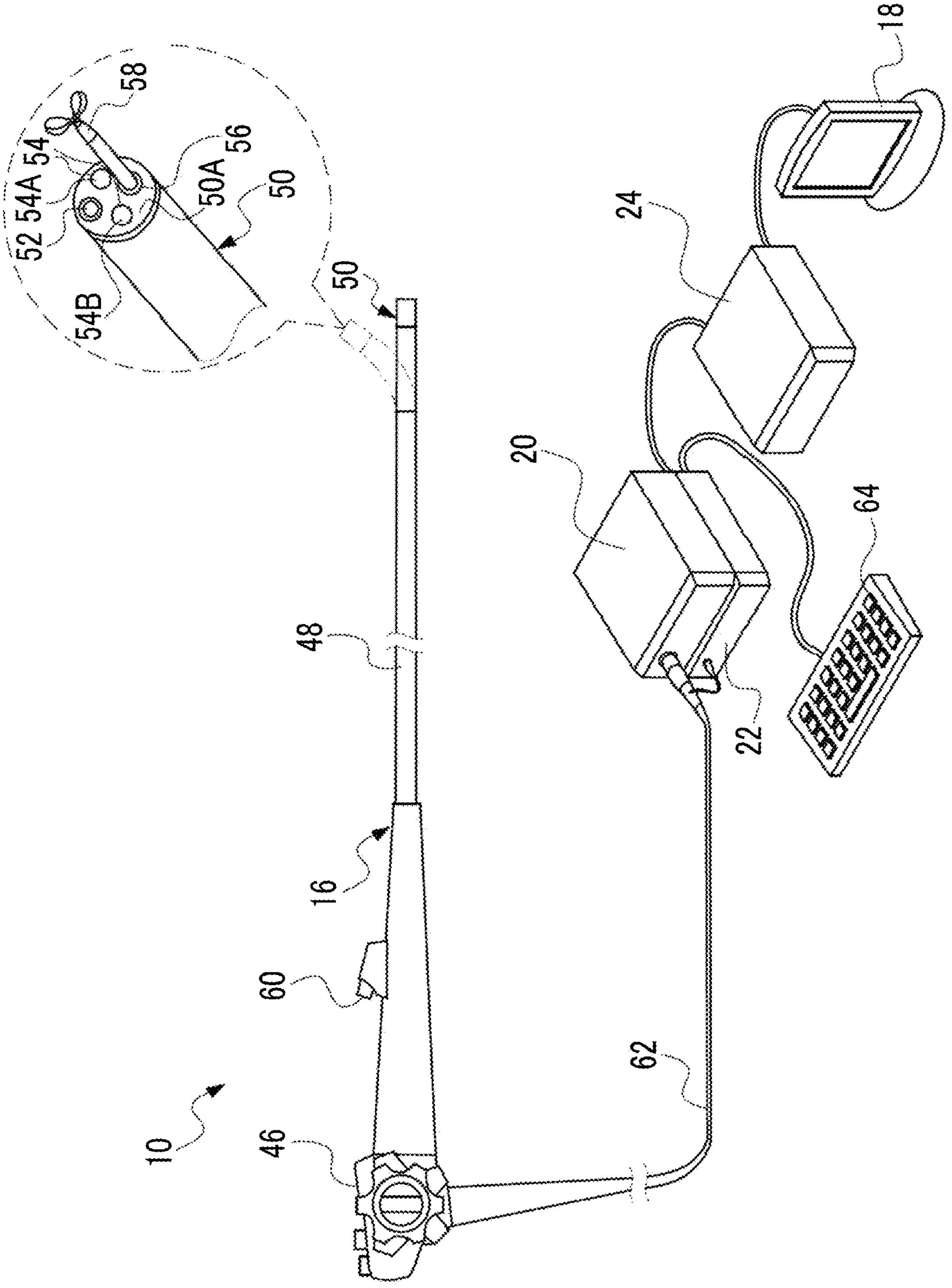
FIG. 2 is a conceptual diagram showing an example of an overall configuration of the endoscope apparatus.

FIG. 2 is a conceptual diagram showing an example of an overall configuration of the endoscope apparatus 10. As shown in FIG. 2, the endoscope 16 comprises an operating part 46 and an insertion part 48. The insertion part 48 is partially bent by operating the operating part 46. The insertion part 48 is inserted into the large intestine 28 while being bent according to a shape of the large intestine 28 (see FIG. 1) in response to the operation of the operating part 46 by the doctor 12 (see FIG. 1).

A camera 52, an illumination device 54, and a treatment tool opening 56 are provided in a distal end part 50 of the insertion part 48. The camera 52 and the illumination device 54 are provided on a distal end surface 50A of the distal end part 50. Here, although a form example is described in which the camera 52 and the illumination device 54 are provided on the distal end surface 50A of the distal end part 50, this is merely an example. The camera 52 and the illumination device 54 may be provided on a side surface of the distal end part 50, so that the endoscope 16 may be configured as a side-viewing endoscope.

The camera 52 is inserted into a body cavity of the subject 26 to image the observation target region. In the present embodiment, the camera 52 acquires the endoscopic moving image 39 by imaging the inside of the body (for example, the inside of the large intestine 28) of the subject 26. Examples of the camera 52 include a CMOS camera. However, this is only an example, and the camera may be other types of camera such as a CCD camera. In the present embodiment, the camera 52 is an example of a "camera" according to the present disclosure.

The illumination device 54 has illumination windows 54A and 54B. The illumination device 54 emits the light 30 (see FIG. 1) through illumination windows 54A and 54B. Examples of the type of the light 30 emitted from the illumination device 54 include visible light (for example, white light) and invisible light (for example, near-infrared light). In addition, the illumination device 54 emits special light through the illumination windows 54A and 54B. Examples of the special light include light for BLI and/or light for LCI. The camera 52 images the inside of the large intestine 28 by an optical method in a state in which the light 30 is emitted inside the large intestine 28 by the illumination device 54.

The treatment tool opening 56 is an opening through which a treatment tool 58 protrudes from the distal end part 50. In addition, the treatment tool opening 56 is also used as a suction port for sucking blood, internal filth, and the like and a delivery port for sending out a fluid.

A treatment tool insertion port 60 is formed in the operating part 46, and the treatment tool 58 is inserted into the insertion part 48 through the treatment tool insertion port 60. The treatment tool 58 passes through the insertion part 48 and protrudes from the treatment tool opening 56 to the outside. Examples of the treatment tool 58 include a hemostatic forceps, a puncture needle, a high-frequency knife, a snare, a catheter, a guide wire, or a cannula. In the example shown in FIG. 2, an aspect is shown in which a hemostatic forceps protrudes from the treatment tool opening 56 as the treatment tool 58.

The endoscope 16 is connected to the light source device 20 and the control device 22 via a universal cord 62. The medical support device 24 and a reception device 64 are connected to the control device 22. In addition, the display device 18 is connected to the medical support device 24. That is, the control device 22 is connected to the display device 18 via the medical support device 24.

Here, since the medical support device 24 is illustrated as an externally connected device for expanding a function performed by the control device 22, a form example is described in which the control device 22 and the display device 18 are indirectly connected to each other via the medical support device 24, but this is merely an example. For example, the display device 18 may be directly connected to the control device 22. In this case, for example, the functions of the medical support device 24 may be provided in the control device 22, or the control device 22 may be provided with a function of causing a server (not shown) to execute the same process as the process (for example, a medical support process which will be described below) executed by the medical support device 24, receiving a processing result of the server, and using the processing result.

The reception device 64 receives an instruction from the doctor 12 and outputs the received instruction as an electric signal to the control device 22. Examples of the reception device 64 include a keyboard, a mouse, a touch panel, a foot switch, a microphone, and/or a remote control device.

The control device 22 controls the light source device 20, transmits and receives various signals to and from the camera 52, or transmits and receives various signals to and from the medical support device 24.

The light source device 20 emits light under the control of the control device 22 and supplies the light to the illumination device 54. A light guide is provided in the illumination device 54, and the light supplied from the light source device 20 is emitted from the illumination windows 54A and 54B through the light guide. The control device 22 causes the camera 52 to perform imaging, acquires the endoscopic moving image 39 (see FIG. 1) from the camera 52, and outputs the endoscopic moving image 39 to a predetermined output destination (for example, the medical support device 24).

The medical support device 24 supports medical care (here, as an example, an endoscopy) by performing various types of image processing on the endoscopic moving image 39 input from the control device 22. The medical support device 24 outputs the endoscopic moving image 39 that has been subjected to various types of image processing to a predetermined output destination (for example, the display device 18).

Here, a form example is described in which the endoscopic moving image 39 output from the control device 22 is output to the display device 18 via the medical support device 24, but this is merely an example. For example, the control device 22 and the display device 18 may be connected to each other, and the endoscopic moving image 39 that has been subjected to the image processing by the medical support device 24 may be displayed on the display device 18 via the control device 22.

Figure 3:
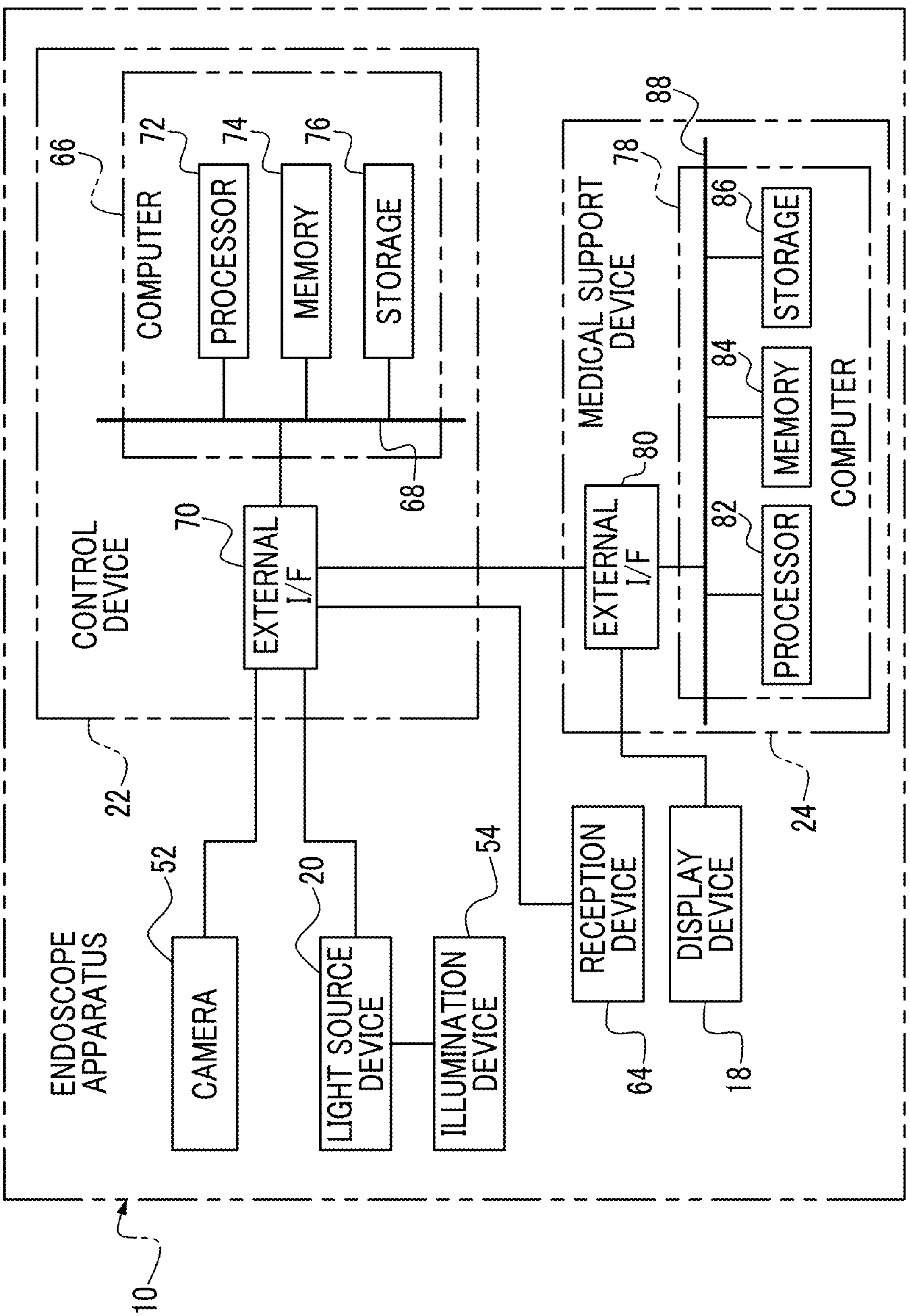
FIG. 3 is a block diagram showing an example of a hardware configuration of an electric system of the endoscope apparatus.

FIG. 3 is a block diagram showing an example of a hardware configuration of an electric system of the endoscope apparatus 10. As shown in FIG. 3, the control device 22 comprises a computer 66, a bus 68, and an external I/F 70. The computer 66 comprises a processor 72, a memory 74, and a storage 76. The processor 72, the memory 74, the storage 76, and the external I/F 70 are connected to the bus 68. The processor 72 controls the entire control device 22. The memory 74 and the storage 76 are used by the processor 72.

The external I/F 70 transmits and receives various types of information between one or more devices (hereinafter, also referred to as "first external devices") outside the control device 22 and the processor 72.

As one of the first external devices, the camera 52 is connected to the external I/F 70, and the external I/F 70 transmits and receives various types of information between the camera 52 and the processor 72. The processor 72 controls the camera 52 via the external I/F 70. In addition, the processor 72 acquires the endoscopic moving image 39 (see FIG. 1) obtained by imaging the inside of the large intestine 28 (see FIG. 1) by the camera 52 via the external I/F 70.

As one of the first external devices, the light source device 20 is connected to the external I/F 70, and the external I/F 70 transmits and receives various types of information between the light source device 20 and the processor 72. The light source device 20 supplies light to the illumination device 54 under the control of the processor 72. The illumination device 54 performs irradiation with the light supplied from the light source device 20.

As one of the first external devices, the reception device 64 is connected to the external I/F 70. The processor 72 acquires the instruction received by the reception device 64 via the external I/F 70 and performs a process corresponding to the acquired instruction.

The medical support device 24 comprises a computer 78 and an external I/F 80. The computer 78 comprises a processor 82, a memory 84, and a storage 86. The processor 82, the memory 84, the storage 86, and the external I/F 80 are connected to a bus 88. In the present embodiment, the medical support device 24 is an example of a "medical support device" according to the present disclosure, the computer 78 is an example of a "computer" according to the present disclosure, and the processor 82 is an example of a "processor" according to the present disclosure.

Since a hardware configuration (that is, the processor 82, the memory 84, and the storage 86) of the computer 78 is basically the same as the hardware configuration of the computer 66, the hardware configuration of the computer 78 will not be described here.

The external I/F 80 transmits and receives various types of information between one or more devices (hereinafter, also referred to as "second external devices") outside the medical support device 24 and the processor 82.

As one of the second external devices, the control device 22 is connected to the external I/F 80. In the example shown in FIG. 3, the external I/F 70 of the control device 22 is connected to the external I/F 80. The external I/F 80 transmits and receives various types of information between the processor 82 of the medical support device 24 and the processor 72 of the control device 22. For example, the processor 82 acquires the endoscopic moving image 39 (see FIG. 1) from the processor 72 of the control device 22 via the external I/Fs 70 and 80 and performs various types of image processing on the acquired endoscopic moving image 39.

As one of the second external devices, the display device 18 is connected to the external I/F 80. The processor 82 controls the display device 18 via the external I/F 80 so that various types of information (for example, the endoscopic moving image 39 subjected to various types of image processing) are displayed on the display device 18.

Meanwhile, in the endoscopy, the doctor 12 visually recognizes the lesion 42 present in the large intestine 28 while observing the endoscopic moving image 39 displayed in the first display region 36. However, in a case where the doctor 12 cannot operate the camera 52 as desired or a body movement (for example, a movement of the large intestine 28) is larger than expected, a positional relationship between the camera 52 and the lesion 42 becomes an unexpected positional relationship. In this case, the lesion 42 may be out of an angle of view of the camera 52 (hereinafter, also simply referred to as an "angle of view"). In a case where the lesion 42 is out of the angle of view, the doctor 12 cannot observe the lesion 42 through the first display region 36. As a result, the doctor 12 loses sight of the lesion 42 that is out of the angle of view. In a case where the doctor 12 loses sight of the lesion 42, there is a concern that the doctor 12 may forget to perform a medical treatment (for example, discrimination and/or resection) for the lost lesion 42. In order to prevent such a situation from occurring, it is important to make the doctor 12 aware of the presence of the lesion 42 that is out of the angle of view.

Figure 4:
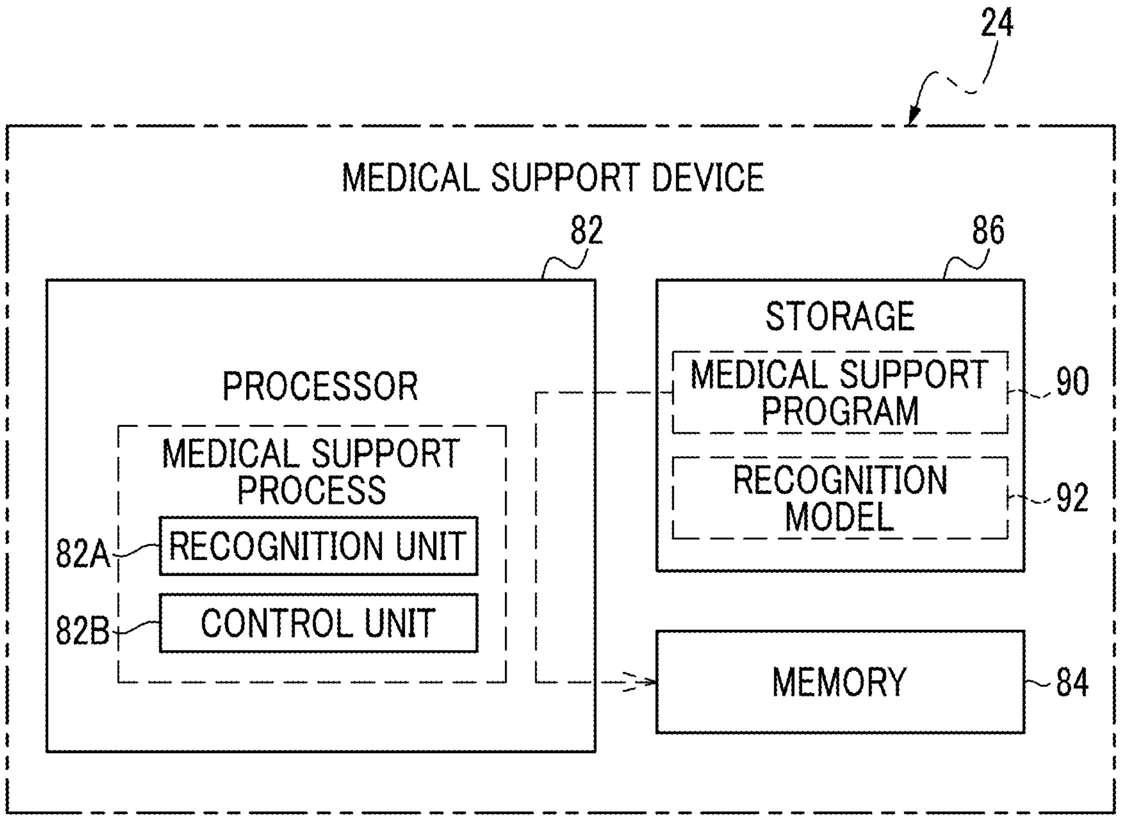
FIG. 4 is a block diagram showing an example of functions of main units according to an embodiment of a processor included in a medical support device and an example of information stored in a storage.

Therefore, in view of such circumstances, in the present embodiment, as shown in FIG. 4 as an example, the medical support process is performed by the processor 82 of the medical support device 24. FIG. 4 is a block diagram showing an example of functions of main units of the processor 82 included in the medical support device 24 and an example of information stored in the storage 86.

A medical support program 90 is stored in the storage 86. The medical support program 90 is an example of a "program" according to the present disclosure. The processor 82 reads out the medical support program 90 from the storage 86 and executes the read-out medical support program 90 on the memory 84 to perform the medical support process. The medical support process is realized by the processor 82 operating as a recognition unit 82A and a control unit 82B according to the medical support program 90 executed on the memory 84.

The storage 86 stores a recognition model 92. Although the details will be described below, the recognition model 92 is used by the recognition unit 82A.

Figure 5:
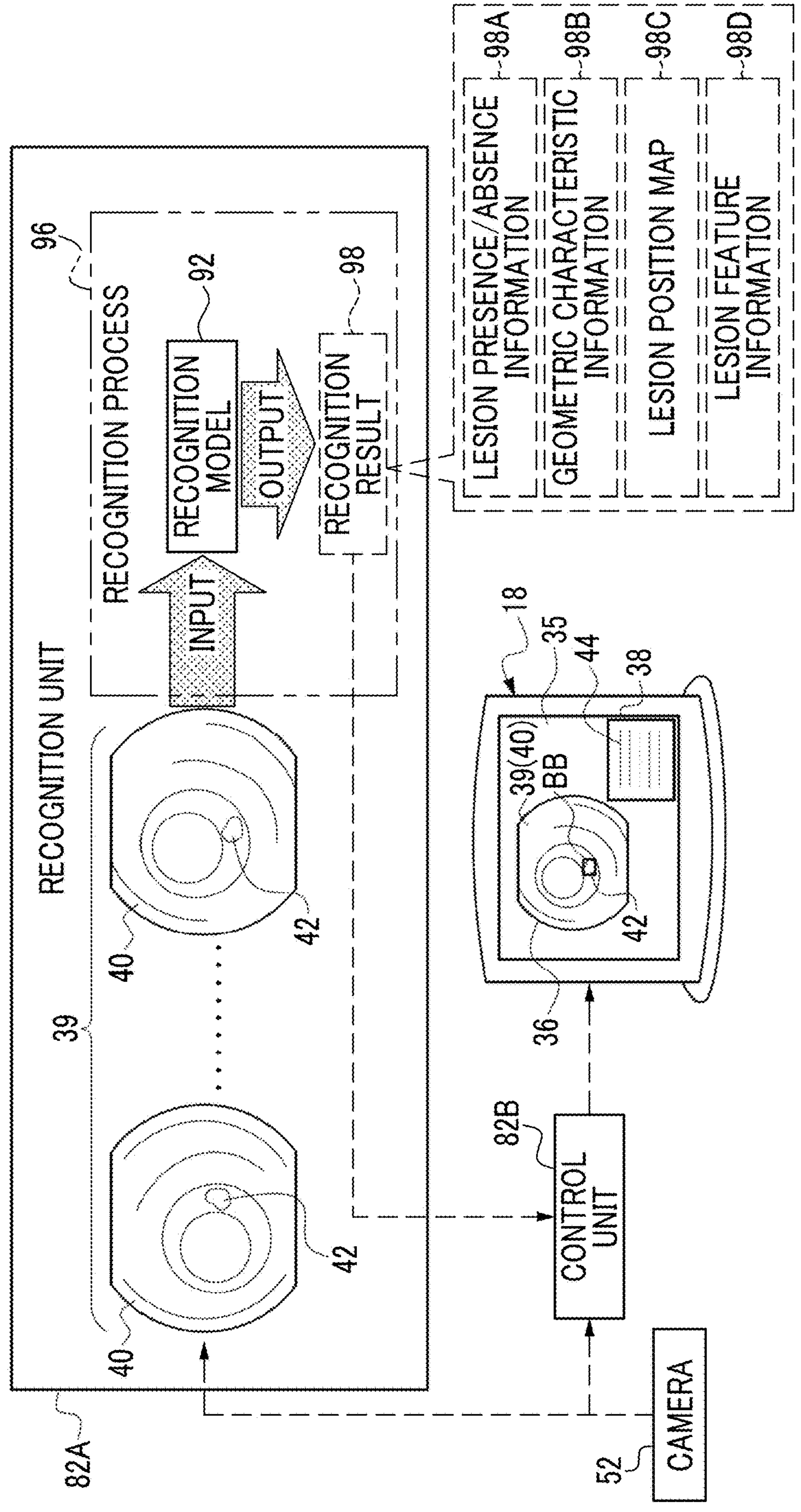
FIG. 5 is a conceptual diagram showing an example of processing contents of a recognition unit and a control unit.

FIG. 5 is a conceptual diagram showing an example of processing contents of the recognition unit 82A and the control unit 82B. As shown in FIG. 5, the recognition unit 82A and the control unit 82B acquire each of the plurality of frames 40 along the time series included in the endoscopic moving image 39, which is generated by imaging the inside of the large intestine 28 by the camera 52 at an imaging frame rate (for example, several tens of frames/second), from the camera 52 in units of one frame along the time series. In the example shown in FIG. 5, an aspect is shown in which the plurality of frames 40 in which the lesion 42 is shown are acquired by the recognition unit 82A. In addition, the frame 40 acquired from the camera 52 by the recognition unit 82A is acquired in synchronization with the recognition unit 82A by the control unit 82B.

The control unit 82B outputs the endoscopic moving image 39 including the plurality of frames 40 along the time series to the display device 18. For example, the control unit 82B displays the endoscopic moving image 39 in the first display region 36 as a live view image. That is, each time the frame 40 is acquired from the camera 52, the control unit 82B displays the acquired frame 40 in the first display region 36 in order at a display frame rate (for example, several tens of frames/second). In addition, the control unit 82B displays the medical information 44 in the second display region 38. In addition, for example, the control unit 82B updates the display content (for example, the medical information 44) of the second display region 38 according to the display content of the first display region 36.

The recognition unit 82A recognizes the lesion 42 shown in the endoscopic moving image 39 by using the endoscopic moving image 39 acquired from the camera 52. That is, the recognition unit 82A recognizes the lesion 42 shown in the frame 40 by sequentially performing a recognition process 96 on each of the plurality of frames 40 along the time series included in the endoscopic moving image 39 acquired from the camera 52. For example, the recognition unit 82A recognizes the presence or absence of the lesion 42, a size of an image region showing the lesion 42 (hereinafter, also referred to as a "lesion image region"), a position of the lesion image region in the frame 40, and features of the lesion 42 (for example, a malignancy grade of the lesion 42, a site where the lesion 42 is present, a kind of the lesion 42, a type of the lesion 42, a form of the lesion 42 (for example, an appearance), an aspect of a boundary between the lesion 42 and a periphery of the lesion 42, and an adhesion aspect of mucus of the lesion 42).

The recognition process 96 is an example of an "object recognition process using an image" according to the present disclosure. The recognition process 96 is performed on the acquired frame 40 each time the frame 40 is acquired by the recognition unit 82A. The recognition process 96 is a process of recognizing the lesion 42 based on the frame 40 by using AI. Here, as the recognition process 96, a process using the recognition model 92 is performed. The recognition model 92 is a trained model for object recognition in a bounding box method using AI.

The recognition model 92 is optimized by performing machine learning on a neural network using first training data. The first training data is a data set including a plurality of data (that is, a plurality of frames of data) in which first example data and first correct answer data are associated with each other.

The first example data is an image assuming the frame 40. First examples of the image assuming the frame 40 include an image obtained by actually imaging the inside of the large intestine with the camera. Second examples of the image assuming the frame 40 include an image virtually created. The first correct answer data is correct answer data (that is, an annotation) for the first example data. Here, as an example of the first correct answer data, annotation for specifying geometric characteristics of the lesion 42 shown in an image used as the first example data, a malignancy grade of the lesion 42, a site where the lesion 42 is present, a kind of the lesion 42, a type of the lesion 42, a form of the lesion 42, an aspect of a boundary between the lesion 42 and a periphery of the lesion 42, an adhesion aspect of mucus of the lesion 42, and the like is used.

The recognition unit 82A acquires the frame 40 from the camera 52 and inputs the acquired frame 40 to the recognition model 92. As a result, the recognition model 92 recognizes the lesion 42 shown in the input frame 40 each time the frame 40 is input, and outputs a recognition result 98.

The recognition result 98 includes lesion presence/absence information 98A. The lesion presence/absence information 98A is information indicating whether or not the lesion 42 is shown in the frame 40 input to the recognition model 92. In addition, in a case where the lesion 42 is shown in the frame 40 input to the recognition model 92, the recognition result 98 includes geometric characteristic information 98B, a lesion position map 98C, lesion feature information 98D, and the like.

The geometric characteristic information 98B is information (for example, coordinates) for specifying a size, a shape, and a position of the lesion 42 in the frame 40. The lesion position map 98C is a map for specifying the position of the lesion 42 in the frame 40. The lesion feature information 98D is information for specifying features of the lesion 42 shown in the frame 40 input to the recognition model 92. Here, the features of the lesion 42 refer to a malignancy grade of the lesion 42, a site where the lesion 42 is present, a kind of the lesion 42, a type of the lesion 42, a form of the lesion 42, an aspect of a boundary between the lesion 42 and a periphery of the lesion 42, an adhesion aspect of mucus of the lesion 42, and the like.

Geometric characteristics (for example, a shape and a size of an outer contour) of the lesion position map 98C correspond to geometric characteristics (for example, a shape and a size of an outer contour) of the frame 40. The lesion position map 98C includes a bounding box BB. The bounding box BB is a rectangular frame (for example, a rectangular border circumscribing the lesion image region) for specifying a position recognized by the recognition model 92 as the position of the lesion 42 in the frame 40, which is shown in the frame 40. In the example shown in FIG. 5, the bounding box BB is displayed to be superimposed on the first display region 36. The display of the bounding box BB is updated in synchronization with a display timing of the endoscopic moving image 39 displayed in the first display region 36.

Here, although an example is described in which the bounding box BB is displayed, this is merely an example, and the bounding box BB may not be displayed. In addition, display and non-display of the bounding box BB may be switched according to various conditions. For example, the display and the non-display of the bounding box BB may be switched in response to the instruction received by the reception device 64, or the display and the non-display of the bounding box BB may be switched in response to the content of processing (for example, the content of the medical support process) performed by the endoscope apparatus 10. In addition, the bounding box BB is merely an example, and an identifier (for example, a code) that replaces the bounding box BB may be displayed instead of the bounding box BB. In this case, for example, the control unit 82B need only specify the position of the lesion 42 in the frame 40 from the geometric characteristic information 98B, and display the identifier instead of the bounding box BB in the vicinity of the specified position.

The lesion position map 98C may be displayed in the second display region 38 as a part of the medical information 44, or may be displayed in a region other than the second display region 38 in the screen 35. The lesion position map 98C displayed on the screen 35 is updated according to a display frame rate applied to the first display region 36. The display of the lesion position map 98C is updated in synchronization with a display timing of the endoscopic moving image 39 displayed in the first display region 36. With such a configuration, the doctor 12 can ascertain an approximate position of the lesion 42 in the endoscopic moving image 39 displayed in the first display region 36 by referring to the lesion position map 98C while observing the endoscopic moving image 39 displayed in the first display region 36. The display and the non-display of the lesion position map 98C may be switched in the same manner as the display and the non-display of the bounding box BB in the first display region 36.

The control unit 82B displays the lesion feature information 98D on the screen 35. In this case, for example, the lesion feature information 98D is displayed in the second display region 38 as a part of the medical information 44.

Figure 6:
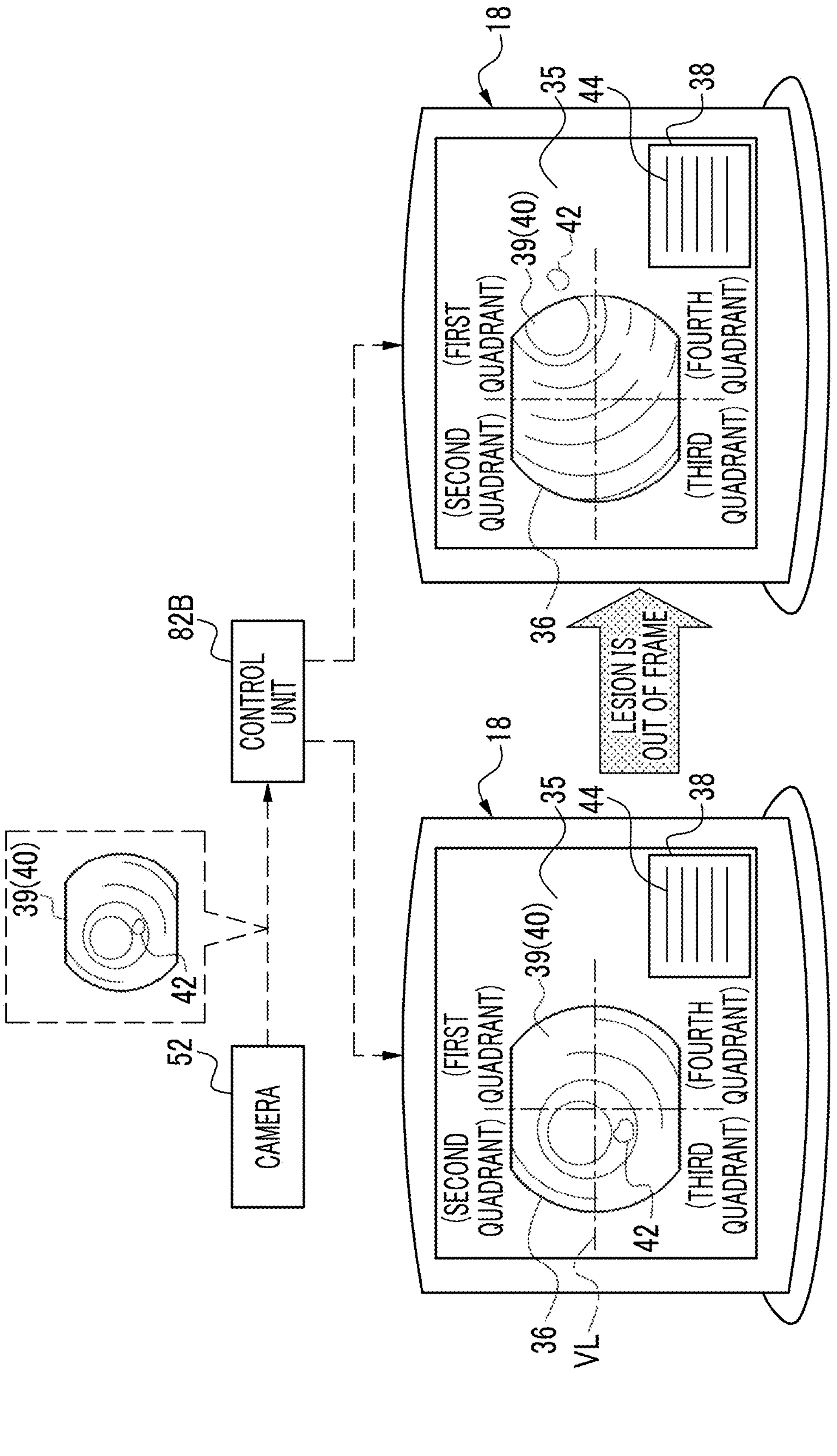
FIG. 6 is a conceptual diagram showing an example of a display content of a first display region in a case where a lesion is within an angle of view and an example of a display content of the first display region in a case where the lesion is out of the angle of view.

FIG. 6 is a conceptual diagram showing an example of the display content of the first display region 36 in a case where the lesion 42 is within the angle of view and an example of the display content of the first display region 36 in a case where the lesion 42 is out of the angle of view. As shown in FIG. 6, a region including the frame 40 and an outer periphery of the frame 40 is divided into first to fourth quadrants by a virtual cross line VL that is not displayed on the screen 35. The cross line VL is formed of a line in a horizontal direction in a front view with respect to the frame 40 and a line in a vertical direction in a front view with respect to the frame 40. A center of the cross line VL (that is, an intersection between the line in a horizontal direction in a front view with respect to the frame 40 and the line in a vertical direction in a front view with respect to the frame 40) is located at a center of the frame 40. The first to fourth quadrants are set in order in a counterclockwise direction with the center of the frame 40 as an axis. Here, although a form example is described in which the region including the frame 40 and the outer periphery of the frame 40 is divided into the first to fourth quadrants, this is merely an example, and the region including the frame 40 and the outer periphery of the frame 40 may be divided into three or fewer regions or may be divided into five or more regions.

In a case where the frame 40 is acquired from the camera 52, the control unit 82B displays the acquired frame 40 in the first display region 36. Here, in a case where the lesion 42 is within the angle of view, the frame 40 in which the lesion 42 is shown is displayed in the first display region 36. In the example shown in FIG. 6, the lesion 42 is shown in the third quadrant in the frame 40. On the other hand, in a case where the lesion 42 is out of the angle of view, the frame 40 in which the lesion 42 is not shown is displayed in the first display region 36. In the example shown in FIG. 6, since the lesion 42 is out of the angle of view toward a first quadrant side, the lesion 42 is not shown in the frame 40 displayed in the first display region 36. Therefore, the doctor 12 cannot visually recognize the presence of the lesion 42 that is out of the angle of view toward the first quadrant side.

Figure 7:
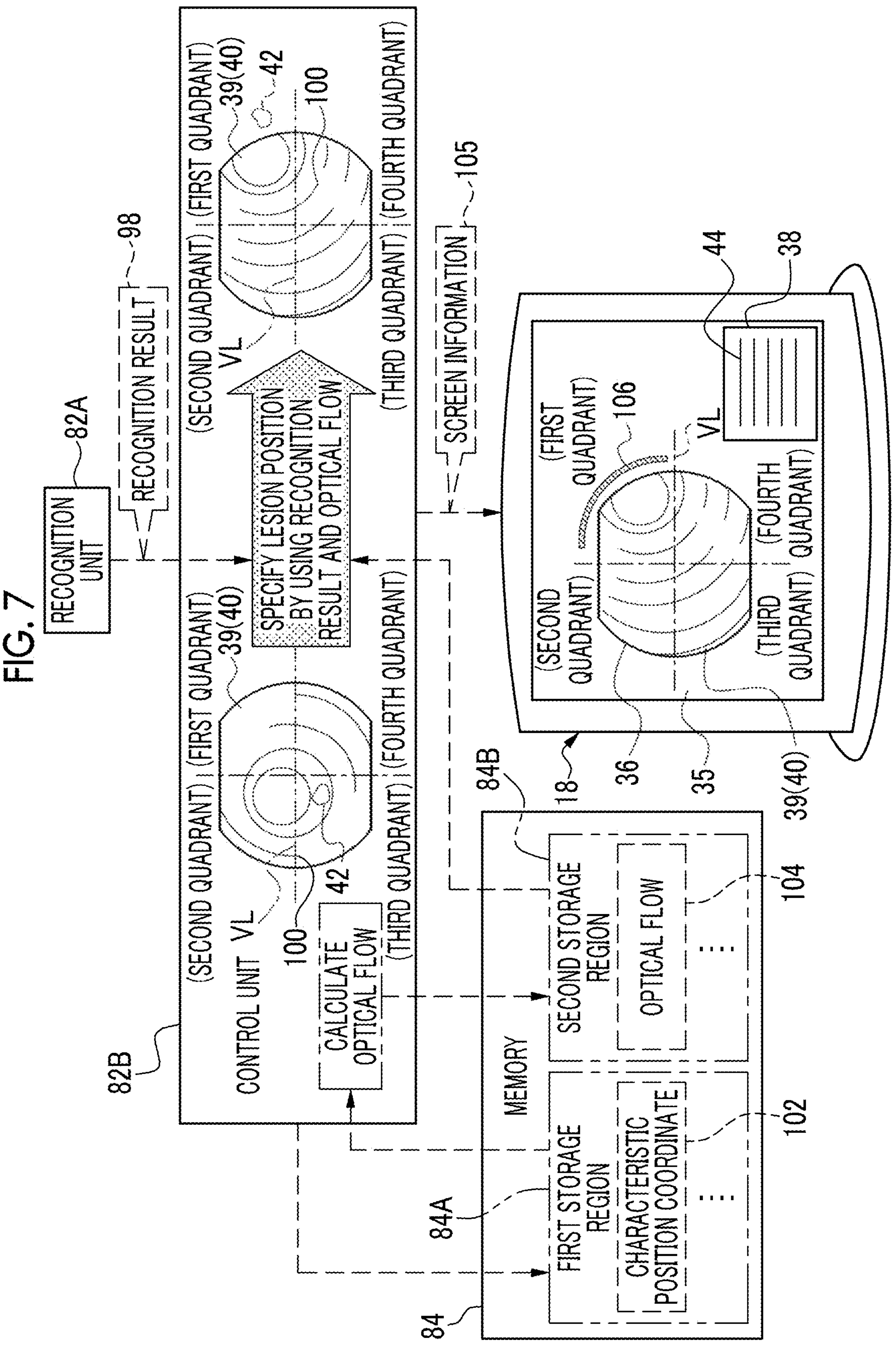
FIG. 7 is a conceptual diagram showing an example of an aspect in which screen information is generated by the control unit and a screen indicated by the screen information is displayed on a display device.

Therefore, as shown in FIG. 7 as an example, the control unit 82B specifies a presence position of the lesion 42 (hereinafter, also referred to as a "lesion position") regardless of whether or not the lesion 42 is shown in the frame 40 by using the recognition result 98 or the like, and displays a specifying result on the screen 35. In order to realize this, the control unit 82B acquires a characteristic position coordinate 102 from the frame 40 acquired from the camera 52 each time the frame 40 is acquired from the camera 52. The characteristic position coordinate 102 is a coordinate for specifying a characteristic location in the frame 40. The characteristic location in the frame 40 refers to, for example, an edge 100 of a high-frequency component region having a characteristic shape (for example, an edge of a characteristic curve) . . . . For example, the high-frequency component region having a characteristic shape is extracted by using a frequency component filter.

The memory 84 is provided with a first storage region 84A, and the control unit 82B stores the acquired characteristic position coordinate 102 in the first storage region 84A in a FIFO manner each time the characteristic position coordinate 102 is acquired from the frame 40. As a result, a plurality of characteristic position coordinates 102 obtained from the plurality of frames 40 are stored in the first storage region 84A in time series. Here, for convenience of description, a form example is described in which one characteristic position coordinate 102 is acquired from each frame 40 and is stored in the first storage region 84A in a FIFO manner, but this is merely an example. A plurality of characteristic position coordinates 102 may be acquired from each frame 40 and may be stored in the first storage region 84A in a FIFO manner. In this case, for example, the characteristic position coordinates 102 are acquired from each of a plurality of high-frequency component regions having a characteristic shape, and the characteristic position coordinates 102 are stored in the first storage region 84A in a FIFO manner for each of the high-frequency component regions having a characteristic shape.

The control unit 82B calculates an optical flow 104 (that is, a movement vector between the frames 40 along the time series) based on the plurality of characteristic position coordinates 102 stored in the first storage region 84A in time series. For example, the calculation of the optical flow 104 is realized by a gradient method. The gradient method is merely an example, and the calculation of the optical flow 104 may be realized by a block matching method or the like. In addition, here, although a form example is described in which the edge 100 is used for the calculation of the optical flow 104, this is merely an example, and a location that can be tracked between the frames 40 along the time series, such as a centroid of the high-frequency component region having a characteristic shape, may be used for the calculation of the optical flow 104.

The memory 84 is provided with a second storage region 84B, and the control unit 82B calculates the optical flow 104 for each frame 40 and stores the optical flow 104 in the second storage region 84B in a FIFO manner. As a result, a plurality of the optical flows 104 obtained by the calculation for each frame 40 are stored in the second storage region 84B in time series.

The control unit 82B specifies the lesion position based on the recognition result 98 obtained by performing the recognition process 96 (see FIG. 5) on the frame 40 acquired from the camera 52 by the recognition unit 82A and one or more optical flows 104 stored in the second storage region 84B (for example, the latest optical flow 104 and/or a plurality of the optical flows 104 along the time series including the latest optical flow 104). For example, the control unit 82B specifies the lesion position of the lesion 42 shown in the frame 40 from the geometric characteristic information 98B included in the recognition result 98 acquired from the recognition unit 82A. Then, the control unit 82B specifies the lesion position of the lesion 42 that is not shown in the frame 40 (in the example shown in FIG. 7, the lesion 42 that is out of the angle of view toward the first quadrant side) based on the lesion position of the lesion 42 shown in the frame 40 and one or more optical flows 104 stored in the second storage region 84B. The specifying of the lesion position by the control unit 82B is realized by acquisition of two-dimensional coordinates by the control unit 82B. Here, the two-dimensional coordinates acquired by the control unit 82B refer to two-dimensional coordinates with a center of the frame 40 as an origin, which can specify the lesion position.

The control unit 82B generates and outputs screen information 105. The screen information 105 is information indicating the screen 35 and is information used for generation of the screen 35. The frame 40, the medical information 44, and the visual assist mark 106 are displayed on the screen 35. Here, the screen information 105 is an example of "screen generation information" according to the present disclosure, and the visual assist mark 106 is an example of "presence position information" and "out-of-angle-of-view position information" according to the present disclosure.

The frame 40 included in the screen information 105 is displayed in the first display region 36. The medical information 44 included in the screen information 105 is displayed in the second display region 38.

The visual assist mark 106 is displayed on the screen 35 in a case where the lesion 42 is out of the angle of view. The visual assist mark 106 is information for specifying the lesion position in a case where the lesion 42 is out of the angle of view on the outside of the frame 40 displayed in the first display region 36. In the example shown in FIG. 7, as an example of the visual assist mark 106, a mark displayed in the screen 35 and assisting in visually specifying the lesion position on the outside of the frame 40 displayed in the first display region 36 is shown. A shape of the visual assist mark 106 is an arc shape. The visual assist mark 106 is displayed on the screen 35 in units of quadrants. The visual assist mark 106 is curved along an outer edge of the first display region 36 in units of quadrants. In the example shown in FIG. 7, since the lesion 42 is out of the angle of view toward the first quadrant side, the visual assist mark 106 is displayed in the first quadrant on the outside of the first display region 36 in which the frame 40 in which the lesion 42 is not shown is displayed, in the screen 35.

Figure 8:
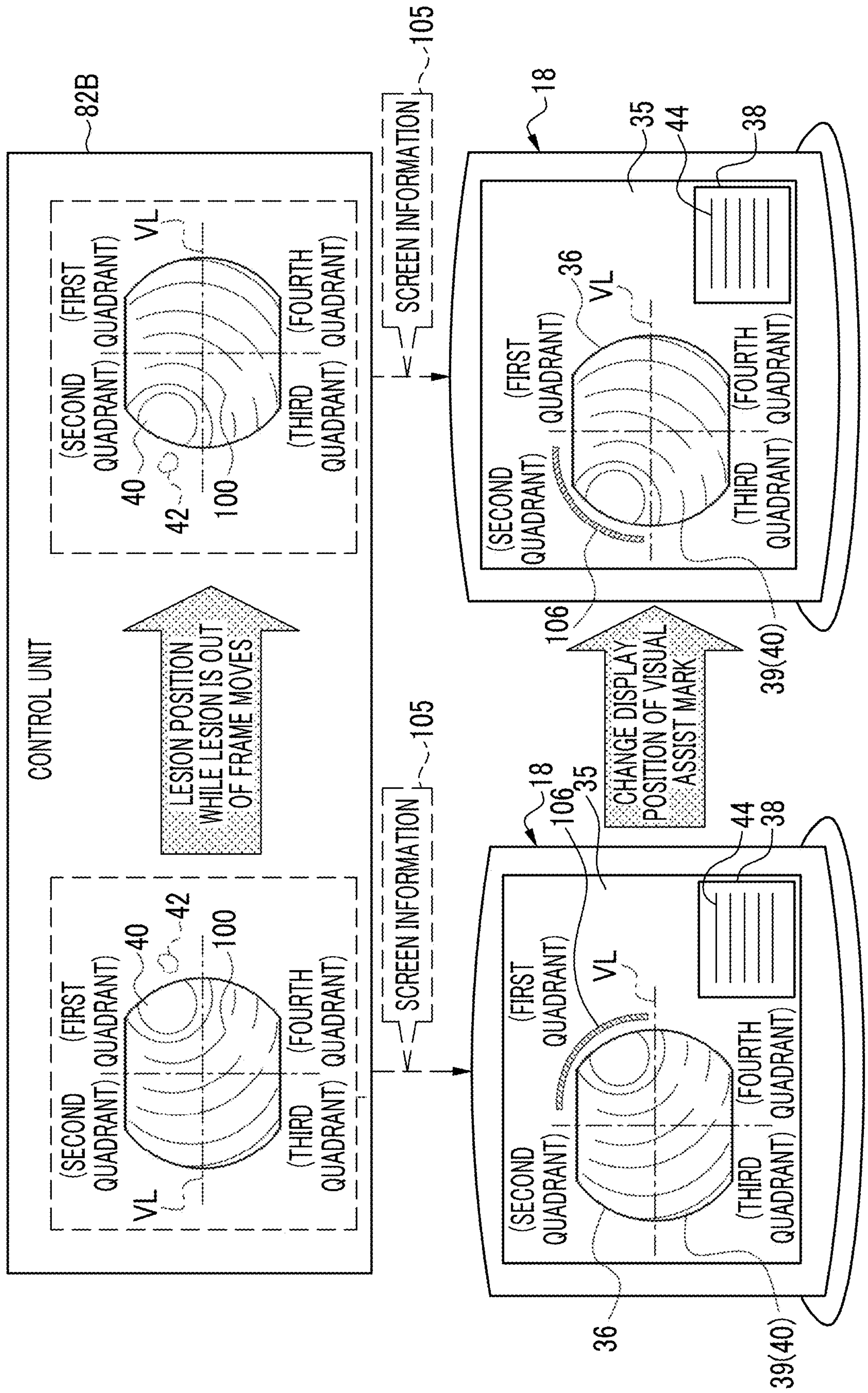
FIG. 8 is a conceptual diagram showing an example of a display content in a case where a lesion position while the lesion is out of a frame (that is, a lesion position of the lesion that is not shown in the frame) is changed.

FIG. 8 is a conceptual diagram showing an example of a display content in a case where the lesion position while the lesion is out of the frame (that is, the lesion position of the lesion 42 that is not shown in the frame 40) is changed. As shown in FIG. 8, in a case where the lesion position while the lesion is out of the frame moves to the outside of the angle of view, the control unit 82B changes a display position of the visual assist mark 106 with respect to the frame 40 in the screen 35 by the method described above (that is, the method using one or more optical flows 104).

The display position of the visual assist mark 106 with respect to the frame 40 in the screen 35 is changed according to a change in the positional relationship between the camera 52 and the lesion 42. The change in the positional relationship between the camera 52 and the lesion 42 is specified from one or more optical flows 104 stored in the second storage region 84B by the control unit 82B.

The control unit 82B specifies the change in the positional relationship between the camera 52 and the lesion 42 based on one or more optical flows 104 stored in the second storage region 84B, and changes the display position of the visual assist mark 106 with respect to the frame 40 in the screen 35 according to the specified change. The change in the positional relationship between the camera 52 and the lesion 42 is caused by the operation of the camera 52 by the doctor 12 and/or the body movement in the large intestine 28. Therefore, the display position of the visual assist mark 106 is changed according to the change in the positional relationship between the camera 52 and the lesion 42, thereby following the operation of the camera 52 by the doctor 12 and/or the body movement in the large intestine 28.

FIG. 8 shows an example in which the lesion position is moved from the first quadrant to the second quadrant on the outside of the angle of view due to the operation of the camera 52 by the doctor 12 and/or the body movement in the large intestine 28. In a case where the lesion position moves from the first quadrant to the second quadrant on the outside of the angle of view, the control unit 82B specifies a route in which the lesion position moves from the first quadrant to the second quadrant on the outside of the angle of view from the optical flow 104. Then, the control unit 82B changes the display position of the visual assist mark 106 in the screen 35 from the first quadrant to the second quadrant on the outside of the first display region 36 in which the frame 40 in which the lesion 42 is not shown is displayed, according to the specified route.

Figure 9:
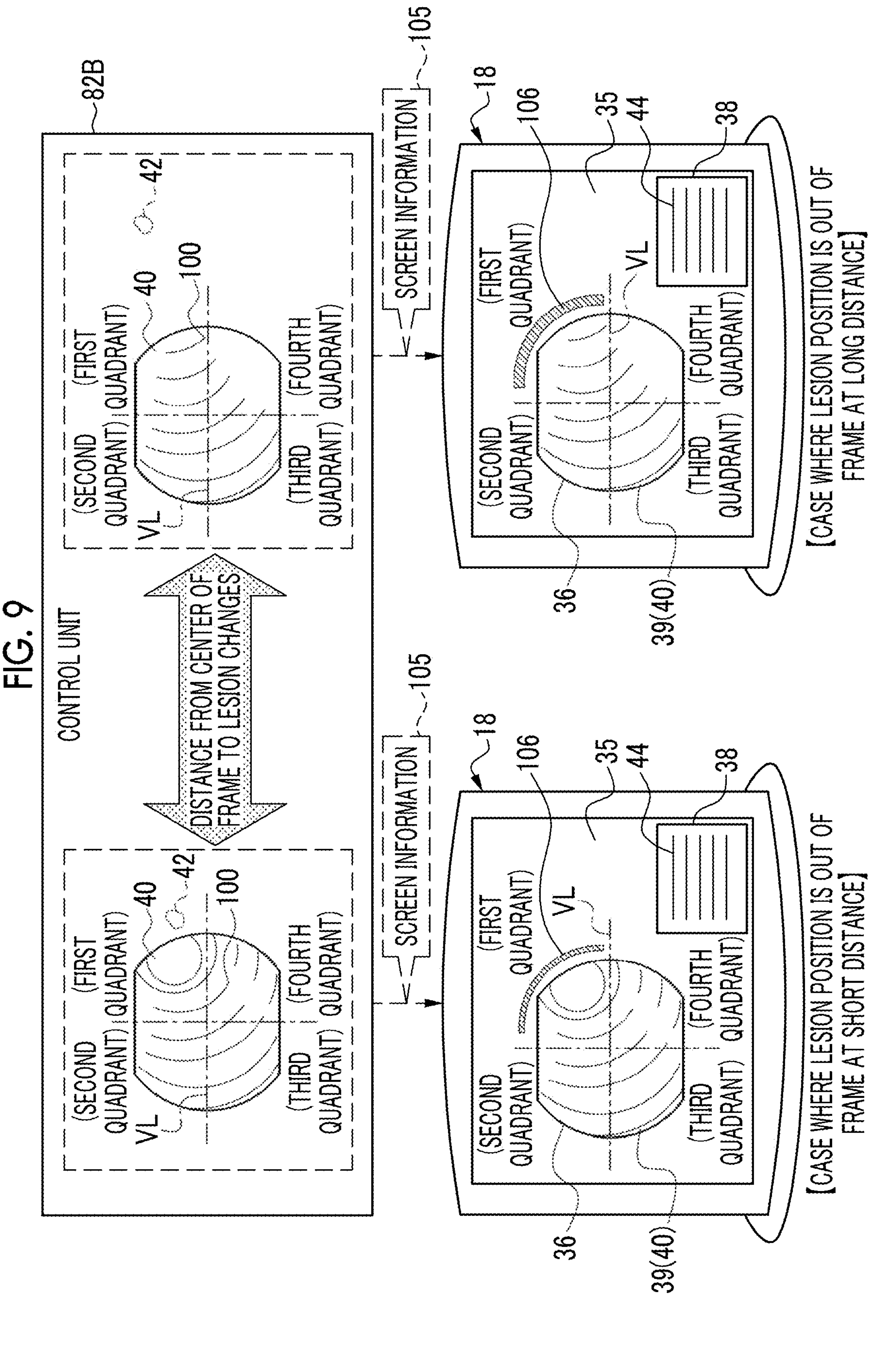
FIG. 9 is a conceptual diagram showing an example of a display aspect of a visual assist mark in a case where a distance from a center of the frame to the lesion is changed.

FIG. 9 is a conceptual diagram showing an example of a display aspect of the visual assist mark 106 in a case where a distance from the center of the frame 40 to the lesion 42 is changed. As shown in FIG. 9, in a case where the distance from the center of the frame 40 to the lesion 42 is changed, the display aspect of the visual assist mark 106 displayed on the screen 35 is changed according to the distance from the center of the frame 40 to the lesion 42.

In the example shown in FIG. 9, a thickness of the visual assist mark 106 displayed on the screen 35 is changed according to the distance from the center of the frame 40 to the lesion 42. The farther the lesion position is from the center of the frame 40, the thicker the visual assist mark 106 displayed on the screen 35 is within a certain range. In this case, for example, the control unit 82B changes the display aspect (here, as an example, the thickness) of the visual assist mark 106 according to the distance from the center of the frame 40 to the lesion 42. The distance from the center of the frame 40 to the lesion 42 is specified based on one or more optical flows 104 stored in the second storage region 84B. Here, the distance from the center of the frame 40 to the lesion 42 is an example of a "feature amount" and an "amount of change" according to the present disclosure.

In addition, here, as the display aspect of the visual assist mark 106, a form example is described in which the thickness of the visual assist mark 106 is changed, but the display aspect of the visual assist mark 106 is not limited to this. For example, the display aspect of the visual assist mark 106 includes a size of at least a part of the visual assist mark 106, a shape of at least a part of the visual assist mark 106, a color of at least a part of the visual assist mark 106, a brightness of at least a part of the visual assist mark 106, a transparency of at least a part of the visual assist mark 106, a pattern of at least a part of the visual assist mark 106, and/or a form of an edge of at least a part of the visual assist mark 106.

Even in a case where the display aspect of the visual assist mark 106 is the display aspect other than the thickness of the visual assist mark 106, the display aspect of the visual assist mark 106 need only be changed such that the visual assist mark 106 is more noticeable as the distance from the center of the frame 40 to the lesion 42 is longer. In addition, on the contrary, the display aspect of the visual assist mark 106 may be changed such that the visual assist mark 106 is more noticeable as the distance from the center of the frame 40 to the lesion 42 is shorter. The display in the display aspect in which the visual assist mark 106 is more noticeable as the distance from the center of the frame 40 to the lesion 42 is longer and the display in the display aspect in which the visual assist mark 106 is noticeable as the distance from the center of the frame 40 to the lesion 42 is shorter may be switched according to various conditions (for example, an instruction received by the reception device 64).

Figure 10:
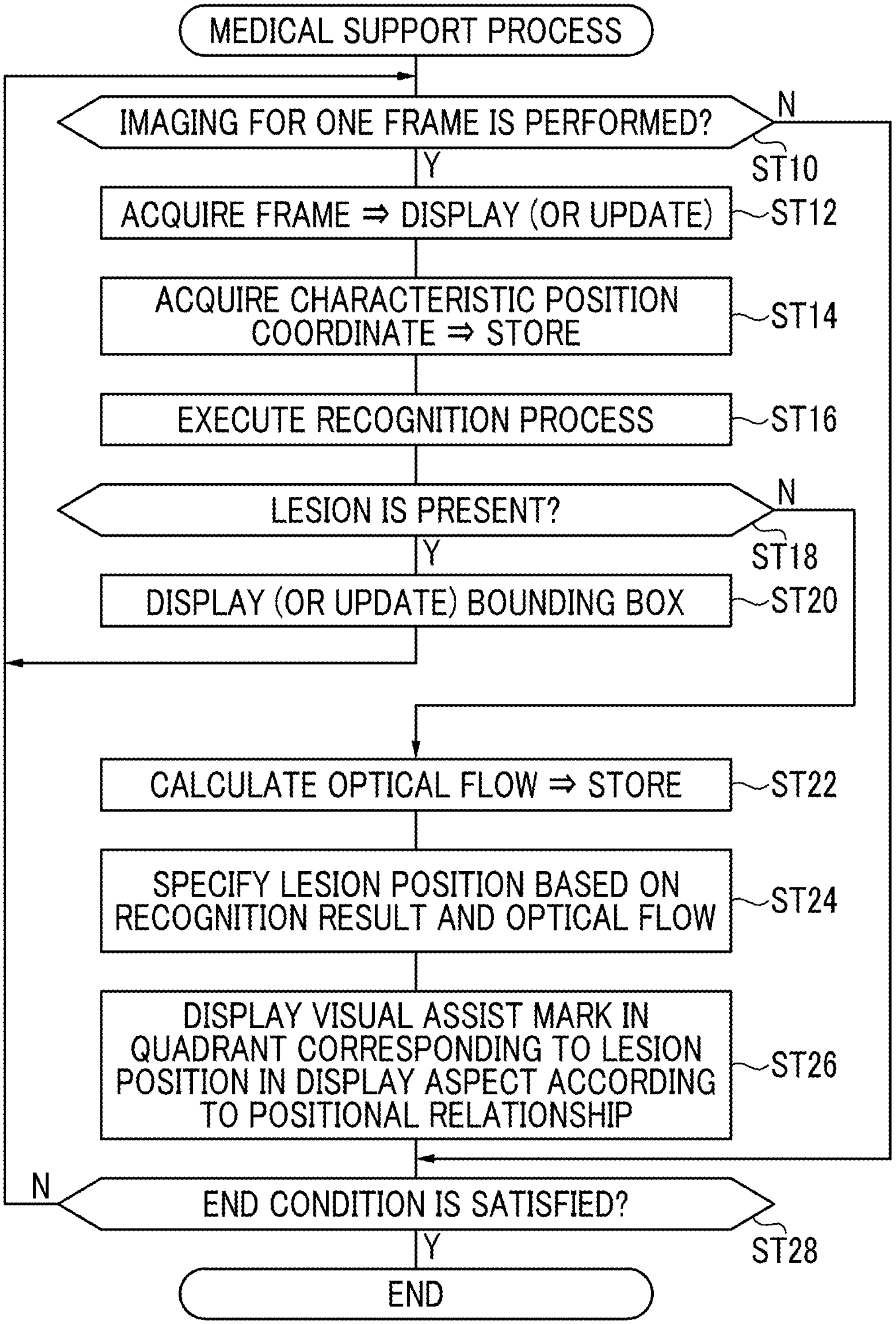
FIG. 10 is a flowchart showing an example of a flow of a medical support process.

Next, an operation of a part of the endoscope apparatus 10 according to the present disclosure will be described with reference to FIG. 10. A flow of the medical support process shown in FIG. 10 is an example of a "medical support method" according to the present disclosure. The medical support process shown in FIG. 10 is executed by the processor 82 in a case where a condition for starting the medical support process is satisfied. Examples of the condition for starting the medical support process include a condition that an instruction to start the medical support process is given to the endoscope apparatus 10 (for example, a condition that the instruction to start the medical support process is received by the reception device 64).

In the medical support process shown in FIG. 10, first, in step ST10, the recognition unit 82A determines whether or not imaging for one frame is performed by the camera 52 in the large intestine 28. In step ST10, in a case where the imaging for one frame is not performed by the camera 52 in the large intestine 28, a negative determination is made, and the medical support process proceeds to step ST28. In step ST10, in a case where the imaging for one frame is performed by the camera 52 in the large intestine 28, a positive determination is made, and the medical support process proceeds to step ST12.

In step ST12, the recognition unit 82A and the control unit 82B acquire the frame 40 obtained by imaging the large intestine 28 by the camera 52. Then, the control unit 82B displays the frame 40 in the first display region 36. Here, in a case where the frame 40 obtained by imaging one frame before is displayed in the first display region 36, the control unit 82B updates the frame 40 displayed in the first display region 36 to the latest frame 40. After the process in step ST12 is executed, the medical support process proceeds to step ST14.

In step ST14, the control unit 82B acquires the characteristic position coordinate 102 from the frame 40 acquired in step ST12. Then, the control unit 82B stores the characteristic position coordinate 102 acquired from the frame 40 in the first storage region 84A in a FIFO manner. After the process in step ST14 is executed, the medical support process proceeds to step ST16. In the following description, for convenience of description, it is assumed that a plurality of the characteristic position coordinates 102 are stored in the first storage region 84A in time series.

In step ST16, the recognition unit 82A executes the recognition process 96 on the frame 40 acquired in step ST12. After the process in step ST16 is executed, the medical support process proceeds to step ST18.

In step ST18, the control unit 82B determines whether or not the lesion 42 is shown in the frame 40 acquired in step ST12 (that is, whether or not the lesion 42 is recognized by the recognition unit 82A) based on the recognition result 98 obtained by performing the recognition process 96 in step ST14. In step ST18, in a case where the lesion 42 is not shown in the frame 40 acquired in step ST12, a negative determination is made, and the medical support process proceeds to step ST22. In step ST18, in a case where the lesion 42 is shown in the frame 40 acquired in step ST12, a positive determination is made, and the medical support process proceeds to step ST20.

In step ST20, the control unit 82B displays the bounding box BB to be superimposed on the frame 40 in the first display region 36 based on the recognition result 98 obtained by performing the recognition process 96 in step ST16. As a result, the bounding box BB is displayed to be superimposed at a display position of the lesion image region in the first display region 36. In addition, in a case where the bounding box BB is displayed in the first display region 36 by executing the previous process of step ST20, the control unit 82B updates the bounding box BB displayed in the first display region 36 based on the recognition result 98 obtained by performing the recognition process 96 in step ST16. After the process in step ST20 is executed, the medical support process proceeds to step ST10.

In step ST22, the control unit 82B calculates the optical flow 104 based on the plurality of characteristic position coordinates 102 stored in the first storage region 84A in time series. Then, the control unit 82B stores the calculated optical flow 104 in the second storage region 84B in a FIFO method. After the process in step ST22 is executed, the medical support process proceeds to step ST24.

In step ST24, the control unit 82B specifies the lesion position based on the recognition result 98 obtained by performing the recognition process 96 in step ST14 and one or more optical flows 104 stored in the second storage region 84B in time series. After the process in step ST24 is performed, the medical support process proceeds to step ST26.

In step ST26, the control unit 82B displays the visual assist mark 106 in the quadrant corresponding to the lesion position specified in step ST24 among the first to fourth quadrants in the screen 35 in a display aspect according to a positional relationship between the frame 40 and the lesion position specified in step ST24 (for example, the distance from the center of the frame 40 to the lesion 42). After the process in step ST26 is executed, the medical support process proceeds to step ST28.

In step ST28, the control unit 82B determines whether or not a medical support process end condition is satisfied. An example of the medical support process end condition is a condition that an instruction for the endoscope apparatus 10 to end the medical support process is given (for example, a condition that the reception device 64 receives an instruction to end the medical support process).

In a case where the medical support process end condition is not satisfied in step ST28, a negative determination is made, and the medical support process proceeds to step ST10. In a case where the medical support process end condition is satisfied in step ST28, a positive determination is made, and the medical support process ends.

As described above, in the present embodiment, the screen information 105 indicating the screen 35 is generated by the control unit 82B and output to the display device 18. The screen 35 indicated by the screen information 105 includes the frame 40 obtained by imaging the large intestine 28 with the camera 52 and the visual assist mark 106. The frame 40 is displayed in the first display region 36 (see FIG. 7). The visual assist mark 106 is a mark for specifying the lesion position that is out of the angle of view on the outside of the first display region 36 in which the frame 40 is displayed (see FIG. 7). The display position of the visual assist mark 106 with respect to the frame 40 in the screen 35 is changed according to a change in the positional relationship between the camera 52 and the lesion 42 (see FIGS. 8 and 9).

As a result, even in a case where the positional relationship between the camera 52 and the lesion 42 is changed, the lesion position can be ascertained by the doctor 12 on the outside of the first display region 36 in which the frame 40 obtained by imaging the large intestine 28 by the camera 52 is displayed, in the screen 35. As a result, even in a case where the lesion 42 is out of the angle of view, the doctor 12 can visually ascertain that the lesion 42 is present outside the angle of view and can also visually estimate the lesion position outside the angle of view by visually recognizing the positional relationship between the visual assist mark 106 and the frame 40 displayed on the screen 35. In addition, since the visual assist mark 106 is displayed on the outside of the first display region 36 in which the frame 40 is displayed in the screen 35, visibility of the frame 40 displayed in the first display region 36 can be favorably maintained as compared to a case where the information indicating that the lesion position is present outside the angle of view is displayed to be superimposed on the frame 40 in the first display region 36.

In addition, in the present embodiment, the change in the positional relationship between the camera 52 and the lesion 42 is caused by the operation of the camera 52 by the doctor 12 and/or the body movement in the large intestine 28. As a result, even in a case where the positional relationship between the camera 52 and the lesion 42 is changed due to the operation of the camera 52 by the doctor 12 and/or the body movement in the large intestine 28, the lesion position can be visually ascertained by the doctor 12 on the outside of the first display region 36 in which the frame 40 obtained by imaging the large intestine 28 by the camera 52 is displayed, in the screen 35.

In addition, in the present embodiment, the display position of the visual assist mark 106 is changed according to the change in the positional relationship between the camera 52 and the lesion 42, thereby following the operation of the camera 52 by the doctor 12 and/or the body movement in the large intestine 28 (see FIGS. 8 and 9). Therefore, even in a case where the positional relationship between the camera 52 and the lesion 42 is changed due to the operation of the camera 52 by the doctor 12 and/or the body movement in the large intestine 28, the doctor 12 can visually track the display position of the visual assist mark 106.

In addition, in the present embodiment, the display aspect of the visual assist mark 106 is changed according to a feature of change in the positional relationship between the camera 52 and the lesion 42 (here, as an example, the distance between the center of the frame 40 and the lesion position) (see FIG. 9). Therefore, as compared to a case where the display aspect of the visual assist mark 106 is always constant regardless of the feature of change in the positional relationship between the camera 52 and the lesion 42, the doctor 12 can visually ascertain a behavior of the feature of change in the positional relationship between the camera 52 and the lesion 42.

In addition, in the present embodiment, the visual assist mark 106 is displayed on the screen 35 on a condition that the lesion 42 is out of the angle of view. Therefore, the doctor 12 can ascertain that the lesion 42 is out of the angle of view at an appropriate timing.

In addition, in the present embodiment, in a case where the lesion 42 is out of the angle of view, the visual assist mark 106 is displayed on the screen 35, and the display aspect of the visual assist mark 106 is changed according to the feature of change in the positional relationship between the camera 52 and the lesion 42 (here, as an example, the distance between the center of the frame 40 and the lesion position) (see FIG. 9). Therefore, even in a case where the lesion 42 is out of the angle of view, the doctor 12 can visually ascertain the behavior of the feature of change in the positional relationship between the camera 52 and the lesion 42.

In addition, in the present embodiment, the recognition process 96 is a process of recognizing the lesion 42 based on the frame 40 by using AI. Therefore, the endoscope apparatus 10 can quickly and accurately recognize the lesion 42 as compared to a case where the lesion 42 is recognized only based on intuition and/or experience of the doctor 12 or the like.

Modification Examples

Figure 11:
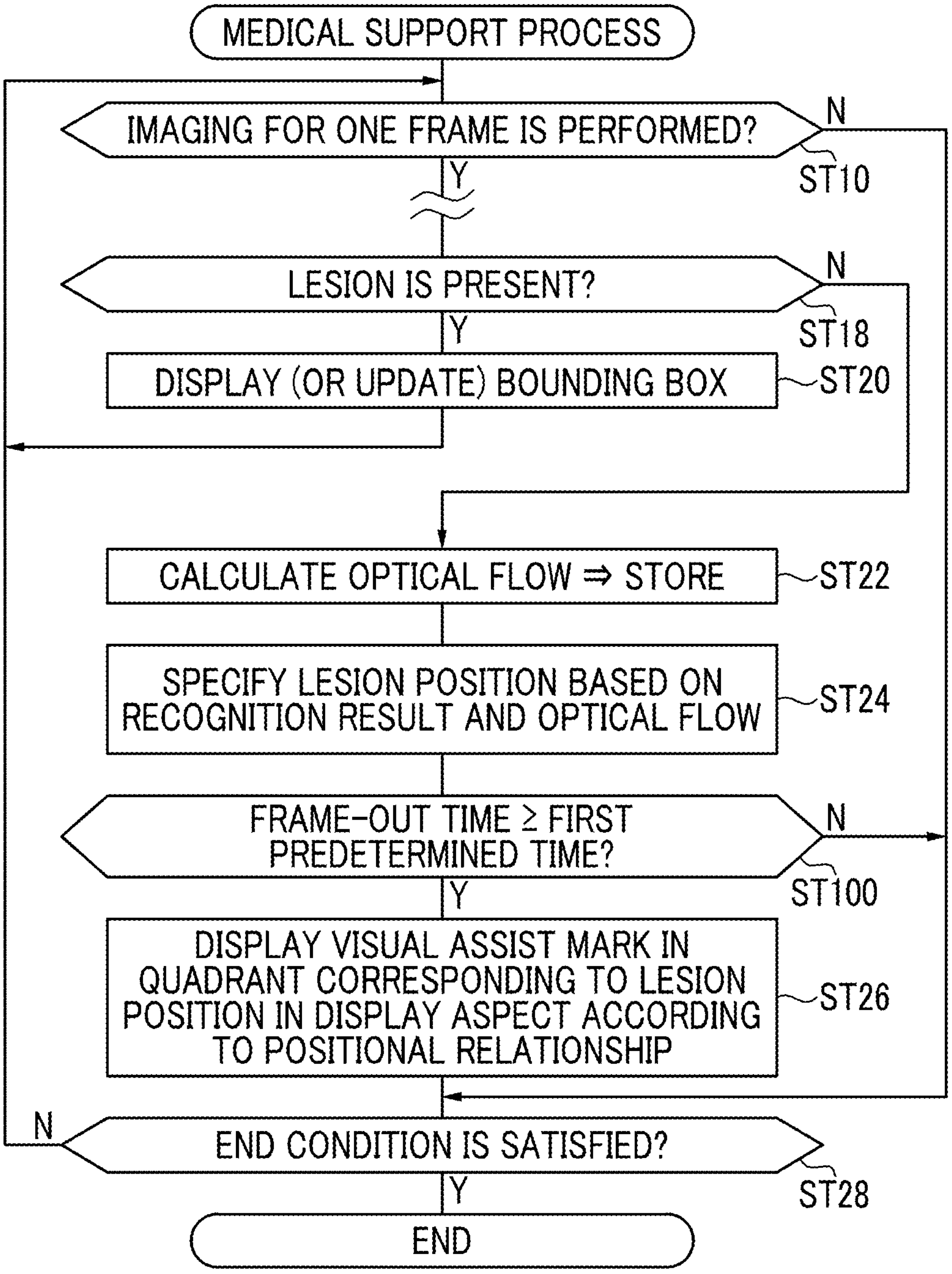
FIG. 11 is a flowchart showing a first modification example of the flow of the medical support process.

In the above-described embodiment, a form example is described in which the medical support process shown in FIG. 10 is executed by the processor 82, but this is merely an example. For example, the medical support process shown in FIG. 11 may be executed by the processor 82. The medical support process shown in FIG. 11 is different from the medical support process shown in FIG. 10 in that a process of step ST100 is provided. The process of step ST100 is provided between the process of step ST24 and the process of step ST26.

In the medical support process shown in FIG. 11, in step ST100, the control unit 82B determines whether or not a time during which the lesion 42 is out of the frame (hereinafter, also referred to as a "frame-out time") is equal to or longer than a first predetermined time (for example, the number of seconds designated in advance within a range of several seconds to several tens of seconds). That is, in step ST100, it is determined whether or not a time during which the lesion 42 is out of the angle of view is equal to or longer than the first predetermined time. Here, the first predetermined time is an example of a "predetermined time" according to the present disclosure.

In step ST100, in a case where the frame-out time is shorter than the first predetermined time, a negative determination is made, and the medical support process proceeds to step ST28. In step ST100, in a case where the frame-out time is equal to or longer than the first predetermined time, a positive determination is made, and the medical support process proceeds to step ST26.

In this way, in a case where the frame-out time is shorter than the first predetermined time, the visual assist mark 106 is not displayed on the screen 35, and in a case where the frame-out time is equal to or longer than the first predetermined time, the visual assist mark 106 is displayed on the screen 35 by executing the process of step ST26. As a result, the visual assist mark 106 is displayed on the screen 35 in a case where there is a high possibility that the lesion 42 that is out of the frame is forgotten by the doctor 12, so that it is possible to suppress occurrence of a situation in which the doctor 12 forgets the presence of the lesion 42 that is out of the angle of view.

The first predetermined time is a time during which the lesion 42 is out of the angle of view and is preferably a time derived by a statistical method and/or a computer simulation or the like using a plurality of pieces of data collected in advance through a plurality of endoscopies, as a time during which the presence of the lesion 42 that is out of the angle of view is forgotten by the doctor 12. In addition, the first predetermined time may be a time determined according to the instruction received by the reception device 64 or the like.

In the medical support process shown in FIG. 11, the process of step ST26 is executed in a case where the condition that the frame-out time is equal to or longer than the first predetermined time is satisfied in step ST100. However, in the medical support process shown in FIG. 12, the process of step ST26 is executed in a case where a plurality of mark display conditions are satisfied. The medical support process shown in FIG. 12 is different from the medical support process shown in FIG. 11 in that a process of step ST200 is applied instead of the process of step ST100.

Figure 12:
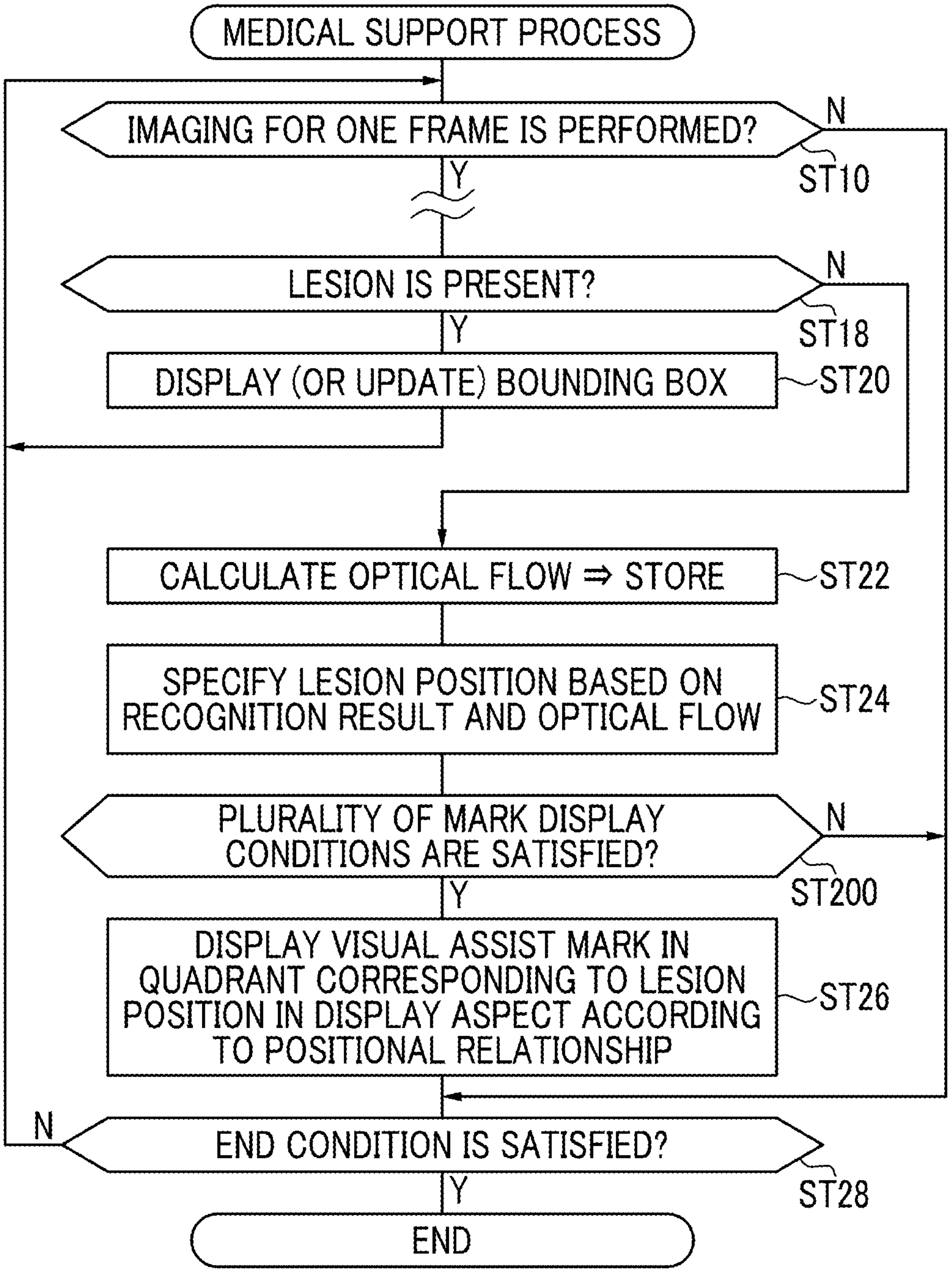
FIG. 12 is a flowchart showing a second modification example of the flow of the medical support process.

In the medical support process shown in FIG. 12, in step ST200, the control unit 82B determines whether or not both of the plurality of mark display conditions are satisfied. The plurality of mark display conditions are a first mark display condition and a second mark display condition. The first mark display condition is a condition defined in step ST100 included in the medical support process shown in FIG. 11, that is, a condition that the frame-out time is equal to or longer than the first predetermined time. The second mark display condition is a condition that a degree of change in the positional relationship between the camera 52 and the lesion 42 exceeds a predetermined degree.

Here, first examples of the degree of change in the positional relationship between the camera 52 and the lesion 42 include the distance from the center of the frame 40 to the lesion 42, that is, an amount of change in the positional relationship between the camera 52 and the lesion 42. Second examples of the degree of change in the positional relationship between the camera 52 and the lesion 42 include a speed of change in the positional relationship between the camera 52 and the lesion 42. Third examples of the degree of change in the positional relationship between the camera 52 and the lesion 42 include a combination of the amount of change in the positional relationship between the camera 52 and the lesion 42 and the speed of change in the positional relationship between the camera 52 and the lesion 42. The combination of the amount of change in the positional relationship between the camera 52 and the lesion 42 and the speed of change in the positional relationship between the camera 52 and the lesion 42 may be represented by a score obtained by integrating a score indicating the amount of change in the positional relationship between the camera 52 and the lesion 42 and a score indicating the speed of change in the positional relationship between the camera 52 and the lesion 42. Examples of the integrated score include a sum of a score indicating the amount of change in the positional relationship between the camera 52 and the lesion 42 and a score indicating the speed of change in the positional relationship between the camera 52 and the lesion 42, or a product of a score indicating the amount of change in the positional relationship between the camera 52 and the lesion 42 and a score indicating the speed of change in the positional relationship between the camera 52 and the lesion 42.

The predetermined degree is a degree of change in the positional relationship between the camera 52 and the lesion 42 and is preferably a degree derived by a statistical method and/or a computer simulation or the like using a plurality of pieces of data collected in advance through a plurality of endoscopies, as a degree to which the presence of the lesion 42 that is out of the angle of view is forgotten by the doctor 12. In addition, the predetermined degree may be a degree determined according to the instruction received by the reception device 64 or the like.

In step ST200, in a case where both of the plurality of mark display conditions are not satisfied, a negative determination is made, and the medical support process proceeds to step ST28. In step ST200, in a case where both of the plurality of mark display conditions are satisfied, a positive determination is made, and the medical support process proceeds to step ST26.

In this way, in a case where both of the plurality of mark display conditions are not satisfied, the visual assist mark 106 is not displayed on the screen 35, and in a case where both of the plurality of mark display conditions are satisfied, the visual assist mark 106 is displayed on the screen 35 by executing the process of step ST26. As a result, the visual assist mark 106 is displayed on the screen 35 in a case where there is a high possibility that the presence of the lesion 42 that is out of the frame is forgotten by the doctor 12, so that it is possible to suppress occurrence of a situation in which the doctor 12 forgets the presence of the lesion 42 that is out of the angle of view.

In step ST200 shown in FIG. 12, it is determined whether or not both of the plurality of mark display conditions are satisfied, but the present disclosure is not limited to this. In step ST200 shown in FIG. 12, it may be determined only whether or not the second mark display condition is satisfied.

Figure 13:
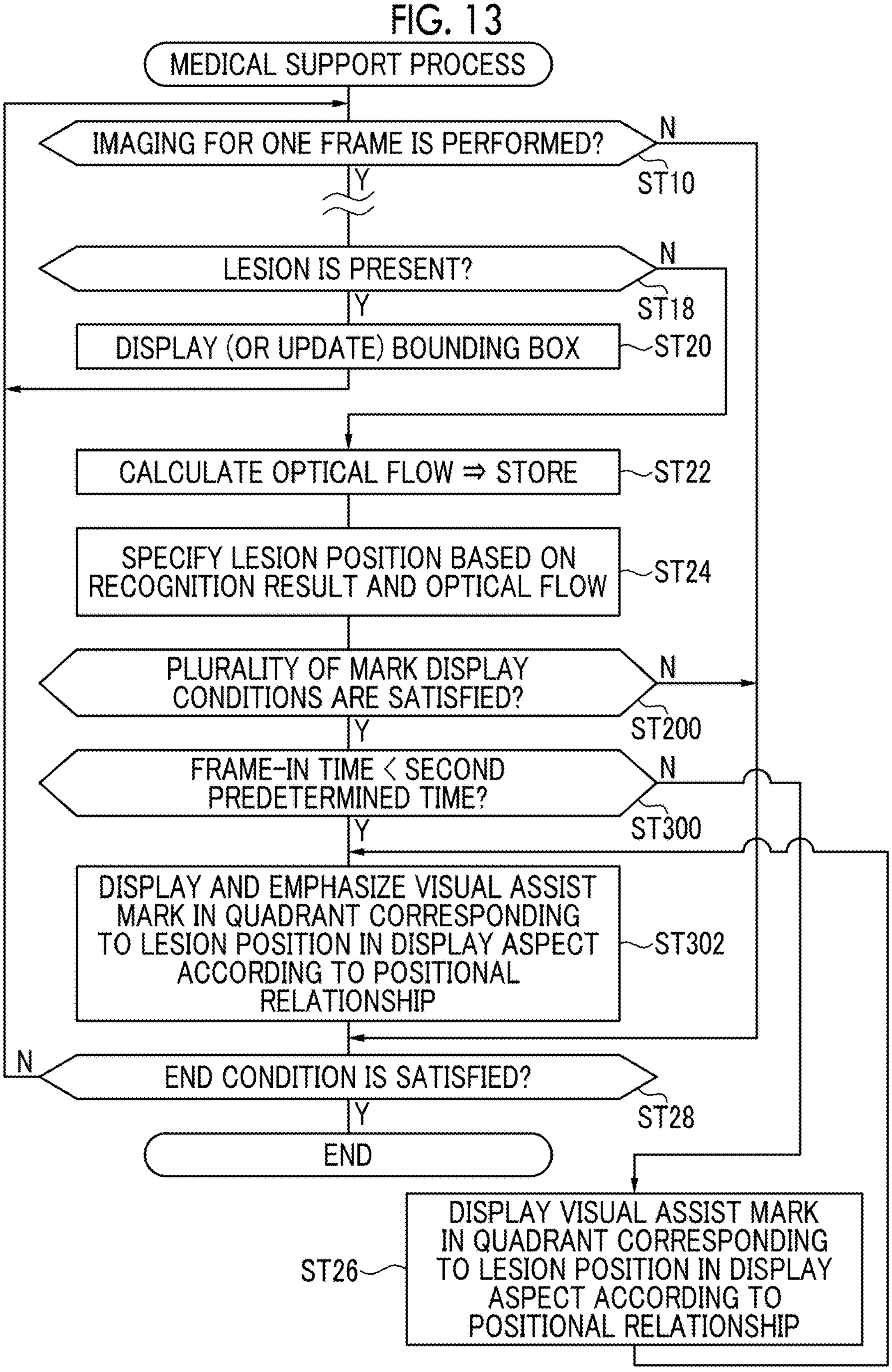
FIG. 13 is a flowchart showing a third modification example of the flow of the medical support process.

Meanwhile, there is a high possibility that the lesion 42, which is shown only for a moment in the frame 40 and then goes out of the frame 40, is overlooked by the doctor 12. In order to reduce the possibility of overlooking such a lesion 42, the medical support process shown in FIG. 13 is executed by the processor 82. The medical support process shown in FIG. 13 is different from the medical support process shown in FIG. 12 in that a process of step ST300 and a process of step ST302 are provided.

In step ST200 included in the medical support process shown in FIG. 13, in a case where a positive determination is made, the medical support process proceeds to step ST300. In step ST300, the control unit 82B determines whether or not a time during which the lesion 42 is in the frame (hereinafter, also referred to as a "frame-in time") is shorter than a second predetermined time (for example, several seconds designated in advance). That is, in step ST300, it is determined whether or not a time during which the lesion 42 is within the angle of view is shorter than the second predetermined time. Here, the frame-in time is an example of a "within-angle-of-view time" according to the present disclosure, and the second predetermined time is an example of a "certain time" according to the present disclosure.

In step ST300, in a case where the frame-in time is equal to or longer than the second predetermined time, a negative determination is made, and the medical support process proceeds to step ST26. Then, after the process of step ST26 is executed, the medical support process proceeds to step ST302. In step ST300, in a case where the frame-in time is shorter than the second predetermined time, a positive determination is made, and the medical support process proceeds to step ST302.

In step ST302, the control unit 82B displays the visual assist mark 106 in the quadrant corresponding to the lesion position specified in step ST24 (that is, a quadrant in which the lesion position is present) among the first to fourth quadrants in the screen 35 in a display aspect according to the positional relationship between the frame 40 and the lesion position specified in step ST24 (for example, the distance from the center of the frame 40 to the lesion 42). Here, the control unit 82B displays the visual assist mark 106 in an emphasized manner as compared to a case where the frame-in time is equal to or longer than the second predetermined time. After the process in step ST302 is executed, the medical support process proceeds to step ST28.

In this way, by performing the process of step ST300 and the process of step ST302, the doctor 12 can easily visually ascertain the presence of the lesion 42 that is shown only for a moment in the frame 40 and then goes out of the frame 40. As a result, it is possible to suppress occurrence of a situation in which the doctor 12 overlooks the lesion 42 that is shown only for a moment in the frame 40 and then goes out of the frame 40.

The second predetermined time is preferably a time that is derived by a statistical method and/or a computer simulation or the like using a plurality of pieces of data collected in advance through a plurality of endoscopies, as a lower limit value of a time during which the doctor 12 can recognize the lesion 42 that is temporarily in the frame and the doctor 12 does not forget the presence of the lesion 42 after the lesion 42 goes out of the frame even in a case where the lesion 42 is out of the frame. In addition, the second predetermined time may be a time determined according to the instruction received by the reception device 64 or the like.

Figure 14:
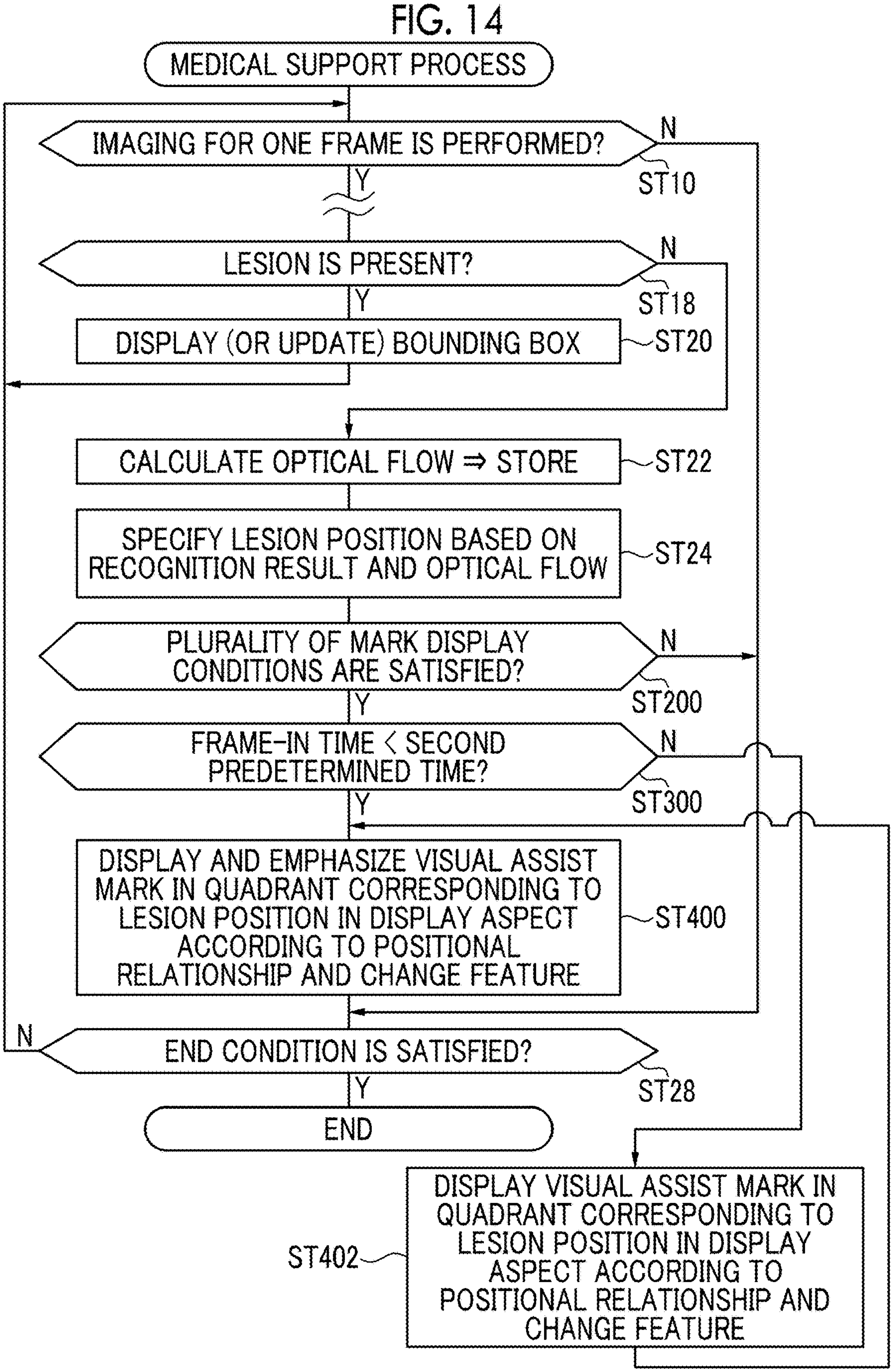
FIG. 14 is a flowchart showing a fourth modification example of the flow of the medical support process.

FIG. 14 is a modification example of the medical support process shown in FIG. 13. The medical support process shown in FIG. 14 is different from the medical support process shown in FIG. 13 in that a process of step ST400 is provided instead of the process of step ST302, and a process of step ST402 is provided instead of the process of step ST26.

In step ST400, the control unit 82B displays the visual assist mark 106 in the quadrant corresponding to the lesion position specified in step ST24 (that is, a quadrant in which the lesion position is present) among the first to fourth quadrants in the screen 35 in a display aspect according to the positional relationship between the frame 40 and the lesion position specified in step ST24 (for example, the distance from the center of the frame 40 to the lesion 42) and a change feature. In addition, the control unit 82B displays the visual assist mark 106 in an emphasized manner as compared to a case where the frame-in time is equal to or longer than the second predetermined time.

In step ST402, the control unit 82B displays the visual assist mark 106 in the quadrant corresponding to the lesion position specified in step ST24 (that is, a quadrant in which the lesion position is present) among the first to fourth quadrants in the screen 35 in a display aspect according to the positional relationship between the frame 40 and the lesion position specified in step ST24 (for example, the distance from the center of the frame 40 to the lesion 42) and a change feature.

Here, the change feature refers to, for example, a feature of change in the positional relationship between the camera 52 and the lesion 42. Examples of the change feature include a speed of change in the positional relationship between the camera 52 and the lesion 42 and/or a direction of change in the positional relationship between the camera 52 and the lesion 42. The speed of change in the positional relationship between the camera 52 and the lesion 42 and the direction of change in the positional relationship between the camera 52 and the lesion 42 are specified from one or more optical flows 104 by the control unit 82B.

Examples of the display aspect of specifying the speed of change in the positional relationship between the camera 52 and the lesion 42 include a display aspect of making the visual assist mark 106 blink and shortening a blinking time interval as the speed of change in the positional relationship between the camera 52 and the lesion 42 increases, or a display aspect of including a numerical value or the like indicating the speed of change in the positional relationship between the camera 52 and the lesion 42 in the visual assist mark 106. The display aspect illustrated here is merely an example, and any display aspect may be adopted as long as the speed of change in the positional relationship between the camera 52 and the lesion 42 can be specified.

Examples of the display aspect of specifying the direction of change in the positional relationship between the camera 52 and the lesion 42 include a display aspect in which an arrow pointing to the direction of change in the positional relationship between the camera 52 and the lesion 42 is used as a pattern of the visual assist mark 106, or a display aspect in which a text or the like representing the direction of change in the positional relationship between the camera 52 and the lesion 42 is included in the visual assist mark 106. The display aspect described here is merely an example, and any display aspect may be adopted as long as the direction of change in the positional relationship between the camera 52 and the lesion 42 can be specified.

As described above, by performing the process of step ST400 and the process of step ST402, the doctor 12 can visually ascertain the feature of change in the positional relationship between the camera 52 and the lesion 42 (for example, the distance from the center of the frame 40 to the lesion 42, the speed of change in the positional relationship between the camera 52 and the lesion 42, and the direction of change in the positional relationship between the camera 52 and the lesion 42).

Figure 15:
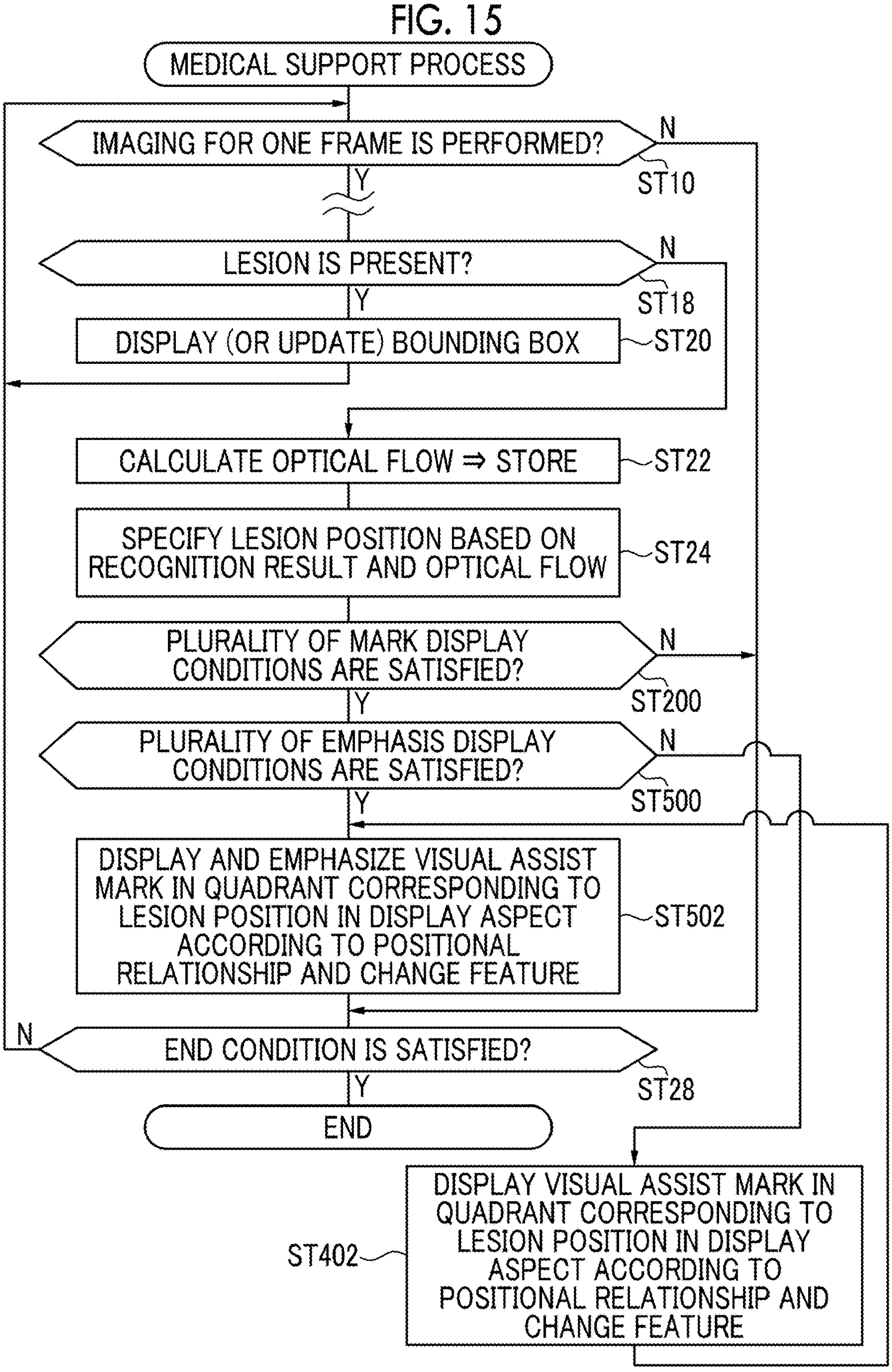
FIG. 15 is a flowchart showing a fifth modification example of the flow of the medical support process.

In the medical support process shown in FIG. 14, a form example is described in which the visual assist mark 106 is displayed in an emphasized manner in a case where a condition that the frame-in time is shorter than the second predetermined time is satisfied in step ST300, but the present disclosure is not limited to this. For example, as shown in FIG. 15, the visual assist mark 106 may be displayed in an emphasized manner in a case where a plurality of emphasis display conditions are satisfied. The medical support process shown in FIG. 15 is different from the medical support process shown in FIG. 14 in that a process of step ST500 and a process of step ST502 are provided between the process of step ST200 and the process of step ST28.

In the medical support process shown in FIG. 14, in step ST500, the control unit 82B determines whether or not both of the plurality of emphasis display conditions are satisfied. The plurality of emphasis display conditions are a first emphasis display condition and a second emphasis display condition. The first emphasis display condition is a condition defined in step ST300 included in the medical support process shown in FIG. 14, that is, a condition that the frame-in time is shorter than the second predetermined time. The second emphasis display condition is a condition that a frequency at which the lesion 42 is repeatedly in and out of the frame in a unit time, that is, a frequency at which the lesion 42 enters and exits the angle of view in a unit time (for example, within 1 second) (hereinafter, also referred to as an "entering and exiting frequency") exceeds a predetermined frequency.

The predetermined frequency is a frequency at which the lesion 42 is repeatedly in and out of the frame in a unit time and is preferably a value derived by a statistical method and/or a computer simulation or the like using a plurality of pieces of data collected in advance through a plurality of endoscopies, as a lower limit value of the entering and exiting frequency at which the doctor 12 is likely to overlook the lesion 42. In addition, the predetermined frequency may be a frequency determined according to the instruction received by the reception device 64 or the like.

In step ST500, in a case where both of the plurality of emphasis display conditions are not satisfied, a negative determination is made, and the medical support process proceeds to step ST402. In step ST500, in a case where both of the plurality of emphasis display conditions are satisfied, a positive determination is made, and the medical support process proceeds to step ST502.

In step ST502, the control unit 82B displays the visual assist mark 106 in the quadrant corresponding to the lesion position specified in step ST24 (that is, a quadrant in which the lesion position is present) among the first to fourth quadrants in the screen 35 in a display aspect according to the positional relationship between the frame 40 and the lesion position specified in step ST24 (for example, the distance from the center of the frame 40 to the lesion 42) and a change feature. In addition, the control unit 82B displays the visual assist mark 106 in an emphasized manner as compared to a case where both of the plurality of emphasis display conditions are not satisfied.

In this way, in a case where both of the plurality of emphasis display conditions are not satisfied, the visual assist mark 106 is not displayed in an emphasized manner, and in a case where both of the plurality of emphasis display conditions are satisfied, the visual assist mark 106 is displayed in an emphasized manner by executing the process of step ST502. As a result, it is possible to suppress occurrence of a situation in which the lesion 42 that frequently enters and exits the angle of view is overlooked by the doctor 12.

In step ST500 shown in FIG. 15, it is determined whether or not both of the plurality of emphasis display conditions are satisfied, but the present disclosure is not limited to this. In step ST500 shown in FIG. 15, it may be determined only whether or not the second emphasis display condition is satisfied.

In the above-described embodiment, as an example of the feature of change in the positional relationship between the camera 52 and the lesion 42, the distance from the center of the frame 40 to the lesion 42 (that is, the amount of change in the positional relationship between the camera 52 and the lesion 42) has been illustrated, but this is merely an example. Examples of the feature of change in the positional relationship between the camera 52 and the lesion 42 include a speed of change in the positional relationship between the camera 52 and the lesion 42 and/or a direction of change in the positional relationship between the camera 52 and the lesion 42. In addition, the feature of change in the positional relationship between the camera 52 and the lesion 42 may be a combination of the speed of change in the positional relationship between the camera 52 and the lesion 42 and the amount of change in the positional relationship between the camera 52 and the lesion 42. In addition, the feature of change in the positional relationship between the camera 52 and the lesion 42 may be a combination of the direction of change in the positional relationship between the camera 52 and the lesion 42 and the amount of change in the positional relationship between the camera 52 and the lesion 42. In addition, the feature of change in the positional relationship between the camera 52 and the lesion 42 may be a combination of the speed of change in the positional relationship between the camera 52 and the lesion 42, the direction of change in the positional relationship between the camera 52 and the lesion 42, and the amount of change in the positional relationship between the camera 52 and the lesion 42.

In the above-described embodiment, a form example is described in which the thickness of the visual assist mark 106 is changed as the display aspect of the visual assist mark 106, but the display aspect of the visual assist mark 106 is not limited to this. For example, the display aspect of the visual assist mark 106 may be presence or absence of display of the visual assist mark 106, a display intensity of the visual assist mark 106, a display time of the visual assist mark 106, and/or a speed of changing the display intensity of the visual assist mark 106.

In a case where the display aspect of the visual assist mark 106 is the presence or absence of the display of the visual assist mark 106, for example, display and non-display of the visual assist mark 106 are switched according to the feature of change in the positional relationship between the camera 52 and the lesion 42. More specifically, for example, in a case where the speed of change in the positional relationship between the camera 52 and the lesion 42 is equal to or higher than a predetermined speed, the visual assist mark 106 is displayed, and in a case where the speed of change in the positional relationship between the camera 52 and the lesion 42 is lower than the predetermined speed, the visual assist mark 106 is not displayed. In addition, for example, in a case where the amount of change in the positional relationship between the camera 52 and the lesion 42 is equal to or greater than a predetermined amount, the visual assist mark 106 is displayed, and in a case where the amount of change in the positional relationship between the camera 52 and the lesion 42 is smaller than the predetermined amount, the visual assist mark 106 is not displayed. In addition, for example, in a case where the direction of change in the positional relationship between the camera 52 and the lesion 42 is a predetermined direction, the visual assist mark 106 is displayed, and in a case where the direction of change in the positional relationship between the camera 52 and the lesion 42 is a direction other than the predetermined direction, the visual assist mark 106 is not displayed.

In a case where the display aspect of the visual assist mark 106 is the display intensity of the visual assist mark 106, for example, the display intensity of the visual assist mark 106 is changed according to the feature of change in the positional relationship between the camera 52 and the lesion 42. More specifically, for example, in a case where the speed of change in the positional relationship between the camera 52 and the lesion 42 is equal to or higher than a predetermined speed, the display intensity of the visual assist mark 106 is set to be equal to or higher than a predetermined intensity, and in a case where the speed of change in the positional relationship between the camera 52 and the lesion 42 is lower than the predetermined speed, the display intensity of the visual assist mark 106 is set to be lower than the predetermined intensity. In addition, for example, in a case where the amount of change in the positional relationship between the camera 52 and the lesion 42 is equal to or greater than the predetermined amount, the display intensity of the visual assist mark 106 is set to be equal to or higher than the predetermined intensity, and in a case where the amount of change in the positional relationship between the camera 52 and the lesion 42 is smaller than the predetermined amount, the display intensity of the visual assist mark 106 is set to lower than the predetermined intensity. In addition, for example, in a case where the direction of change in the positional relationship between the camera 52 and the lesion 42 is the predetermined direction, the display intensity of the visual assist mark 106 is set to be equal to or higher than the predetermined intensity, and in a case where the direction of change in the positional relationship between the camera 52 and the lesion 42 is a direction other than the predetermined direction, the display intensity of the visual assist mark 106 is set to lower than the predetermined intensity.

In a case where the display aspect of the visual assist mark 106 is the display time of the visual assist mark 106, for example, the display time of the visual assist mark 106 (for example, a time during which the visual assist mark 106 is continuously displayed) is changed according to the feature of change in the positional relationship between the camera 52 and the lesion 42. More specifically, for example, in a case where the speed of change in the positional relationship between the camera 52 and the lesion 42 is equal to or higher than the predetermined speed, the display time of the visual assist mark 106 is set to be equal to or longer than a certain time, and in a case where the speed of change in the positional relationship between the camera 52 and the lesion 42 is lower than the predetermined speed, the display time of the visual assist mark 106 is set to be shorter than the certain time. In addition, for example, in a case where the amount of change in the positional relationship between the camera 52 and the lesion 42 is equal to or greater than the predetermined amount, the display time of the visual assist mark 106 is set to be equal to or longer than the certain time, and in a case where the amount of change in the positional relationship between the camera 52 and the lesion 42 is smaller than the predetermined amount, the display time of the visual assist mark 106 is set to be shorter than the certain time. In addition, for example, in a case where the direction of change in the positional relationship between the camera 52 and the lesion 42 is the predetermined direction, the display time of the visual assist mark 106 is set to be equal to or longer than the certain time, and in a case where the direction of change in the positional relationship between the camera 52 and the lesion 42 is a direction other than the predetermined direction, the display time of the visual assist mark 106 is set to be shorter than the certain time.

In a case where the display aspect of the visual assist mark 106 is the speed of changing the display intensity of the visual assist mark 106, for example, the speed of changing the display intensity of the visual assist mark 106 is changed according to the feature of change in the positional relationship between the camera 52 and the lesion 42. More specifically, for example, the speed of changing the display intensity of the visual assist mark 106 increases as the speed of change in the positional relationship between the camera 52 and the lesion 42 increases.

In this way, the presence or absence of the display of the visual assist mark 106, the display intensity of the visual assist mark 106, the display time of the visual assist mark 106, and/or the speed of changing the display intensity of the visual assist mark 106 are changed according to the feature of change in the positional relationship between the camera 52 and the lesion 42, so that the doctor 12 can visually recognize the feature of change in the positional relationship between the camera 52 and the lesion 42 even in a case where the lesion 42 is out of the angle of view.

Figure 16:
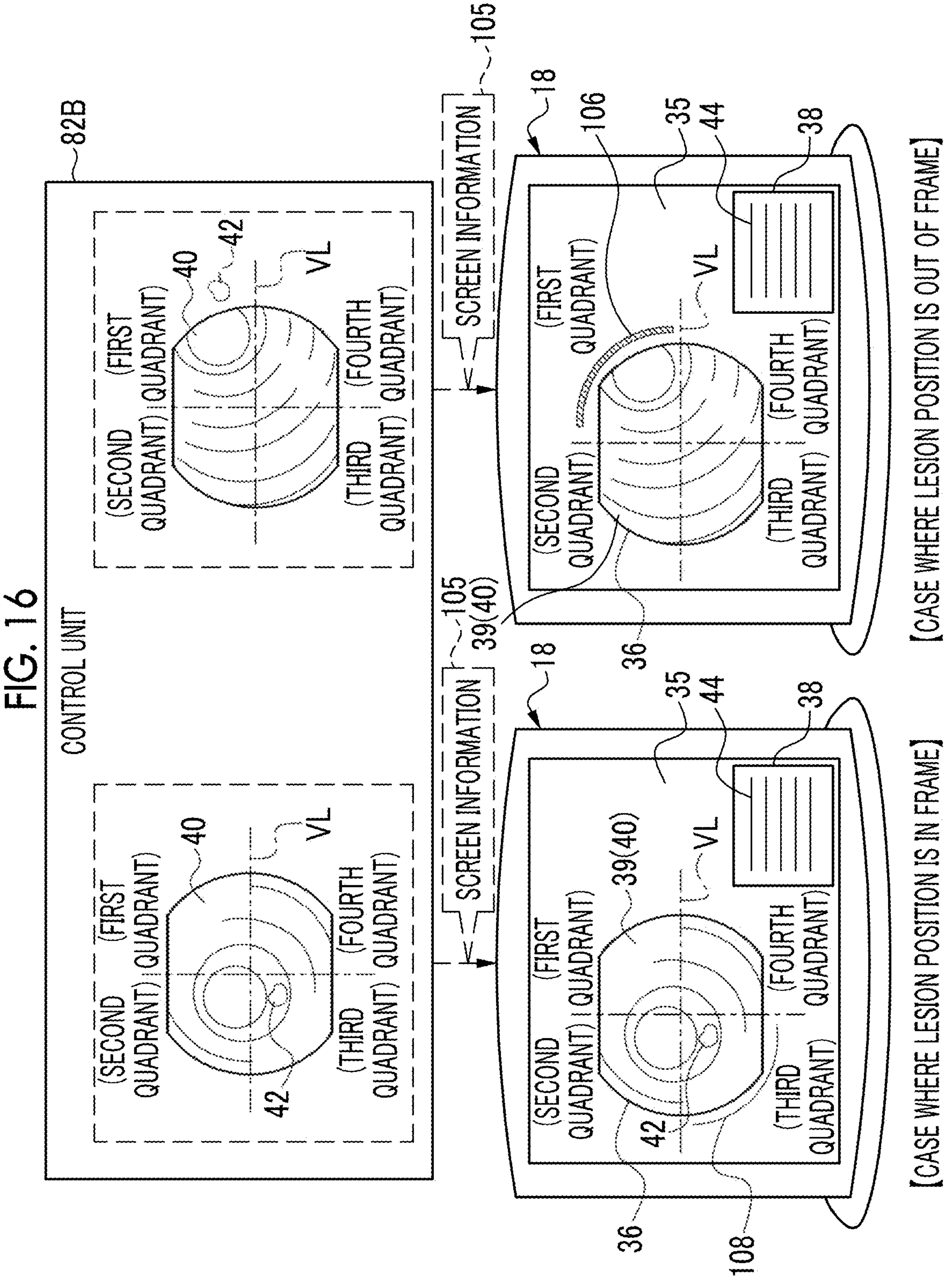
FIG. 16 is a conceptual diagram showing a display example of the screen in a case where the lesion position is in the frame and a display example of the screen in a case where the lesion position is out of the frame.

In the above-described embodiment, a form example is described in which the visual assist mark 106 is displayed on the screen 35 in order to allow the doctor 12 to visually ascertain the lesion position of the lesion 42 that is not shown in the frame 40, but the present disclosure is not limited to this. For example, as shown in FIG. 16, even in a case where the lesion 42 is shown in the frame 40 (that is, in a case where the lesion 42 is within the angle of view), a visual assist mark 108 may be displayed on the outside of the first display region 36 in which the frame 40 in which the lesion 42 is shown is displayed, in the screen 35. The visual assist mark 108 is information for specifying the presence position of the lesion 42 in a case where the lesion 42 is within the angle of view on the outside of the first display region 36 in which the frame 40 in which the lesion 42 is shown is displayed. In the example shown in FIG. 16, the visual assist mark 108 is an example of "within-angle-of-view position information" according to the present disclosure.

Here, the visual assist mark 108 is illustrated, but this is merely an example. For example, a text, a code, or the like may be applied instead of the visual assist mark 108, and any information may be used as long as the information is for specifying the presence position of the lesion 42 in a case where the lesion 42 is within the angle of view on the outside of the first display region 36 in which the frame 40 in which the lesion 42 is shown is displayed.

In a case where the visual assist mark 108 is displayed on the outside of the first display region 36 in which the frame 40 in which the lesion 42 is shown is displayed, the bounding box BB may not be displayed. In this way, it is possible to prevent the visibility of the frame 40 from being impaired due to the presence of the bounding box BB, and it is possible to visually specify in which quadrant of the frame 40 the lesion 42 is shown.

In addition, it is preferable that the visual assist mark 108 is displayed in a display aspect distinguishable from the visual assist mark 106. In the example shown in FIG. 16, the visual assist mark 106 is represented by an arc-shaped thin line and is displayed in a display aspect that is less noticeable than the visual assist mark 108. In this way, the doctor 12 can visually ascertain which lesion 42 is within the angle of view and which lesion 42 is out of the angle of view.

Figure 17:
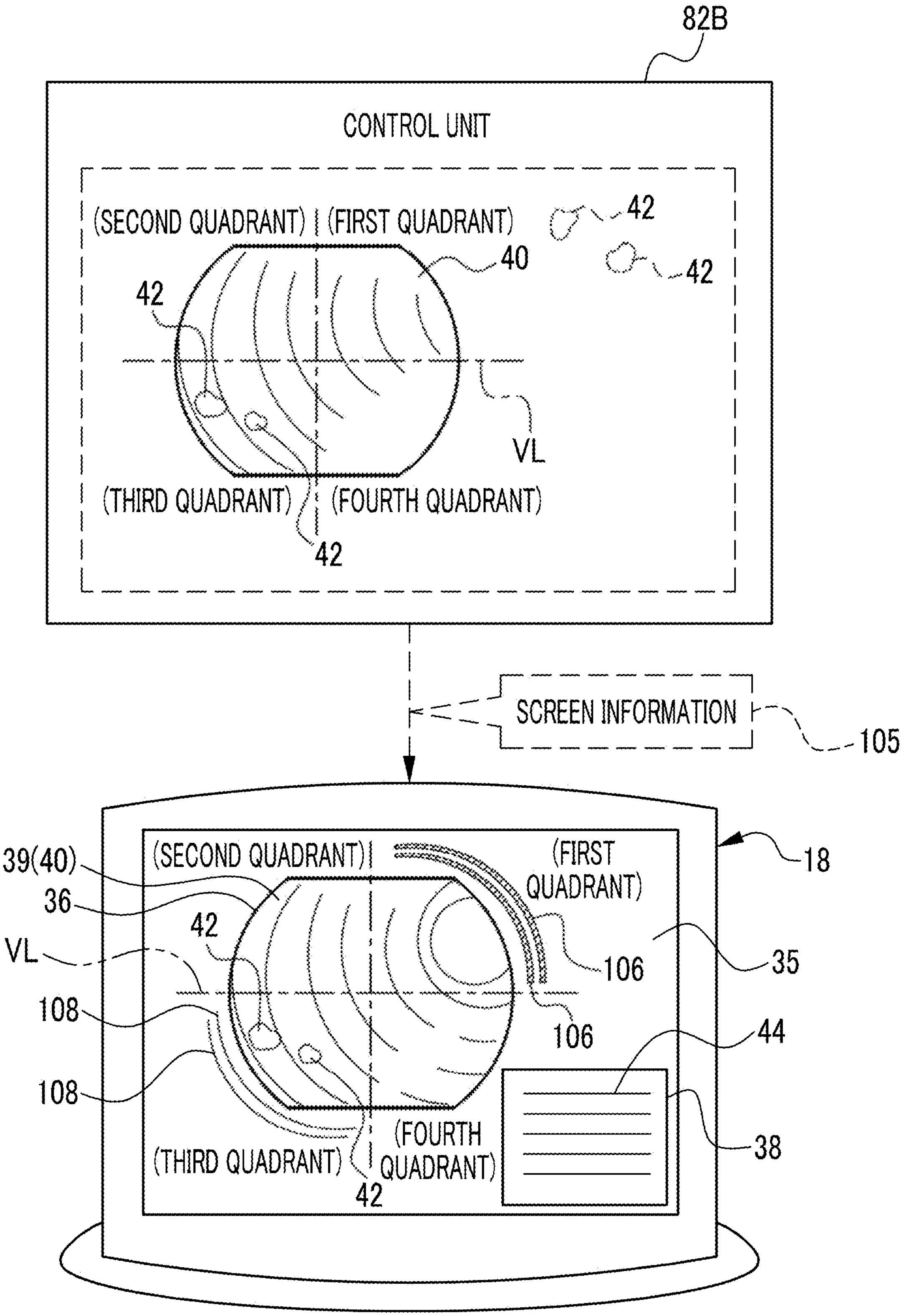
FIG. 17 is a conceptual diagram showing a first display example of the screen in a case where a plurality of lesions are present inside and outside the angle of view.

In the above-described embodiment, a form example is described in which a single visual assist mark 106 is displayed on the screen 35 in a case where a single lesion 42 is out of the angle of view, but the present disclosure is not limited to this. For example, as shown in FIG. 17, in a case where a plurality of the lesions 42 (in the example shown in FIG. 17, two lesions 42) are out of the angle of view, the visual assist marks 108 in a number corresponding to the number of the lesions 42 (in the example shown in FIG. 17, two visual assist marks 108) may be displayed on the screen 35. In this case as well, as in the above-described embodiment, the visual assist mark 108 is displayed in a quadrant corresponding to each lesion position on the outside of the first display region 36 in which the frame 40 is displayed such that the quadrant in which the lesion 42 is present can be visually specified.

In addition, in a case where a plurality of the lesions 42 (in the example shown in FIG. 17, two lesions 42) are shown in the frame 40, the visual assist marks 106 in a number corresponding to the number of the lesions 42 shown in the frame 40 (in the example shown in FIG. 17, two visual assist marks 106) may be displayed on the screen 35. In this case as well, as in the example shown in FIG. 16, each visual assist mark 108 is displayed in a quadrant corresponding to each lesion position on the outside of the first display region 36 in which the frame 40 is displayed such that the quadrant in which each lesion 42 is present can be visually specified.

Figure 18:
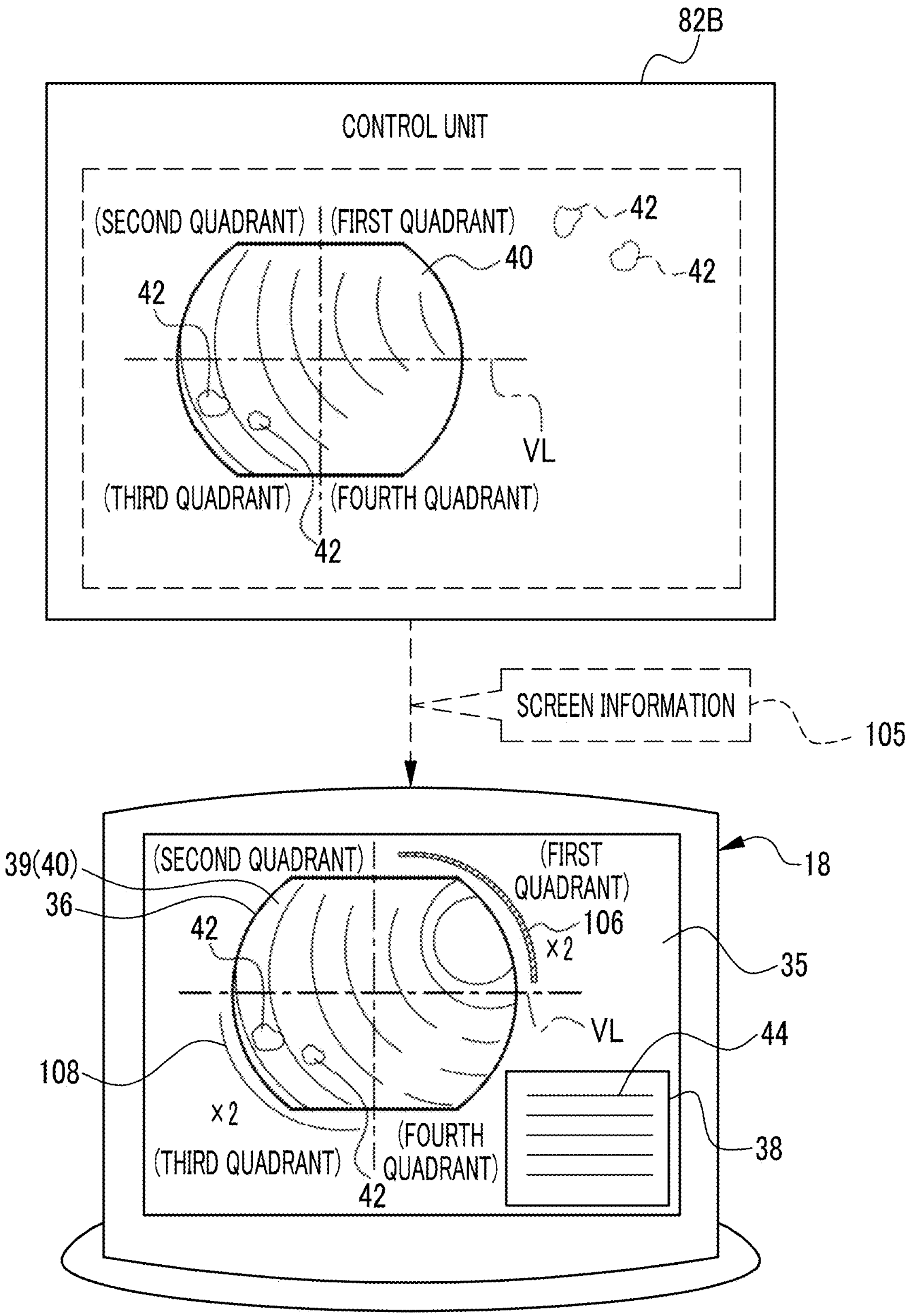
FIG. 18 is a conceptual diagram showing a second display example of the screen in a case where a plurality of lesions are present inside and outside the angle of view.

In addition, in the example shown in FIG. 17, a form example is described in which the visual assist marks 108 in a number corresponding to the number of the lesions 42 are displayed on the screen 35, but this is merely an example. For example, as shown in FIG. 18, in a case where a plurality of the lesions 42 that are out of the angle of view are present in the same quadrant (in the example shown in FIG. 18, the first quadrant), it is sufficient that, in the screen 35, one visual assist mark 108 is displayed in the same quadrant (in the example shown in FIG. 18, the first quadrant), and a symbol, a text, or the like indicating the number of the lesions 42 (in the example shown in FIG. 18, a text "×2" indicating two) is displayed.

In addition, in a case where a plurality of the lesions 42 that are within the angle of view are present in the same quadrant (in the example shown in FIG. 18, the third quadrant), it is sufficient that, in the screen 35, one visual assist mark 106 is displayed in the same quadrant (in the example shown in FIG. 18, the third quadrant), and a symbol, a text, or the like indicating the number of the lesions 42 (in the example shown in FIG. 18, a text "×2" indicating two) is displayed.

Figure 19:
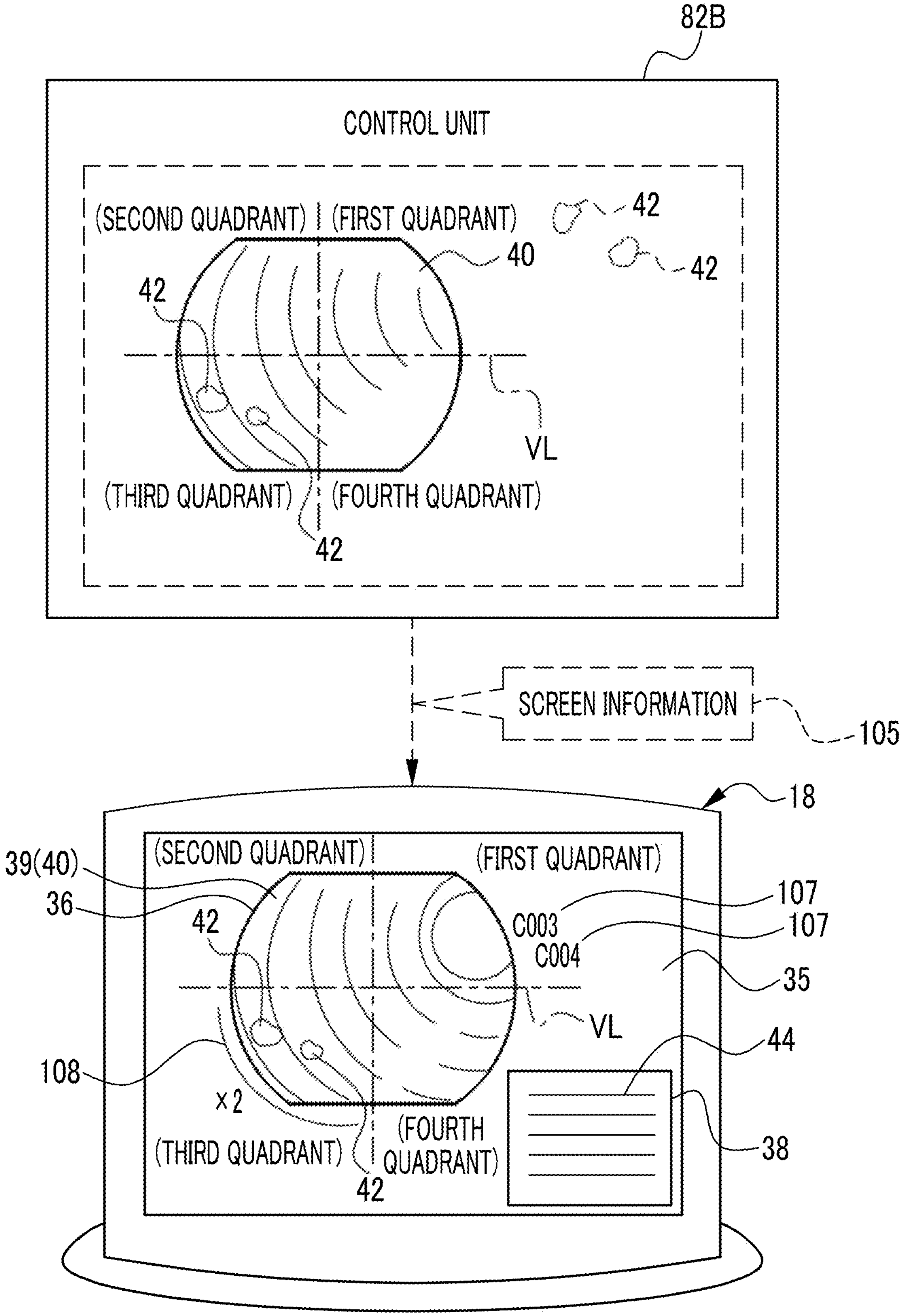
FIG. 19 is a conceptual diagram showing a third display example of the screen in a case where a plurality of lesions are present inside and outside the angle of view.

In the above-described embodiment, the presence of the lesion 42 that is out of the angle of view is visually ascertained by the doctor 12 by displaying the visual assist mark 108 on the screen 35, but the present disclosure is not limited to this. For example, as shown in FIG. 19, a code 107 may be displayed on the screen 35 instead of the visual assist mark 108. The code 107 is an identifier uniquely determined for the lesion 42. Therefore, by displaying different codes 107 on the screen 35, it is possible to visually ascertain that different lesions 42 are present outside the angle of view. In addition, the code 107 may be a code for specifying the feature of the lesion 42 (for example, a malignancy grade of the lesion 42, a site where the lesion 42 is present, a kind of the lesion 42, a type of the lesion 42, a form of the lesion 42, an aspect of a boundary between the lesion 42 and a periphery of the lesion 42, and an adhesion aspect of mucus of the lesion 42). In addition, a display aspect of the code 107 (for example, a color, a brightness, a thickness, and/or a blinking pattern) may be changed according to the change feature described above.

In the example shown in FIG. 19, an aspect is shown in which the visual assist mark 106 is displayed on the screen 35, but the code 107 may be displayed on the screen 35 instead of the visual assist mark 106.

Figure 20:
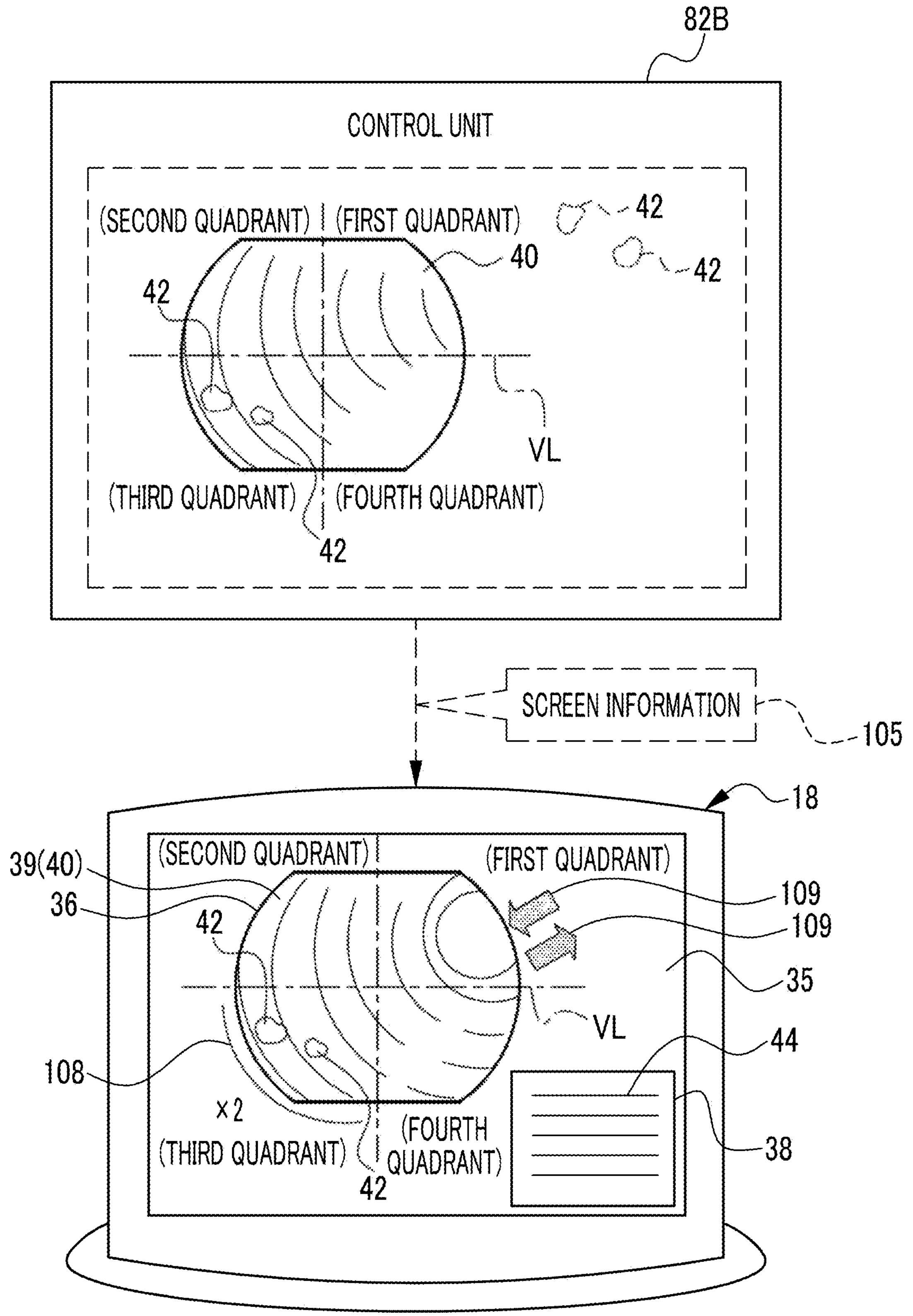
FIG. 20 is a conceptual diagram showing a fourth display example of the screen in a case where a plurality of lesions are present inside and outside the angle of view.

In the example shown in FIG. 19, a form example is described in which the presence of the lesion 42 that is out of the angle of view is visually ascertained by the doctor 12 by displaying the code 107 on the screen 35, but the present disclosure is not limited to this. For example, as shown in FIG. 20, in a case where the lesion 42 that is out of the angle of view is present, an arrow 109 for specifying the presence of the lesion 42 that is out of the angle of view may be displayed on the screen 35 instead of the code 107.

For example, a direction of the arrow 109 is determined according to a positional relationship between the camera 52 and the lesion 42 that is out of the angle of view, and is changed according to a change in the positional relationship between the camera 52 and the lesion 42 that is out of the angle of view. For example, in a case where the distance between the camera 52 and the lesion 42 that is out of the angle of view is smaller than a threshold value, a tip of the arrow 109 is directed to the first display region 36 side, and in a case where the distance between the camera 52 and the lesion 42 that is out of the angle of view is equal to or greater than the threshold value, the tip of the arrow 109 is directed to the outside of the first display region 36. In addition, as the distance between the camera 52 and the lesion 42 that is out of the angle of view increases, a length of the arrow 109 may also increase within a certain range. In addition, a display aspect of the arrow 109 (for example, a color, a brightness, a thickness, and/or a blinking pattern) may be changed according to the change feature described above.

Figure 21:
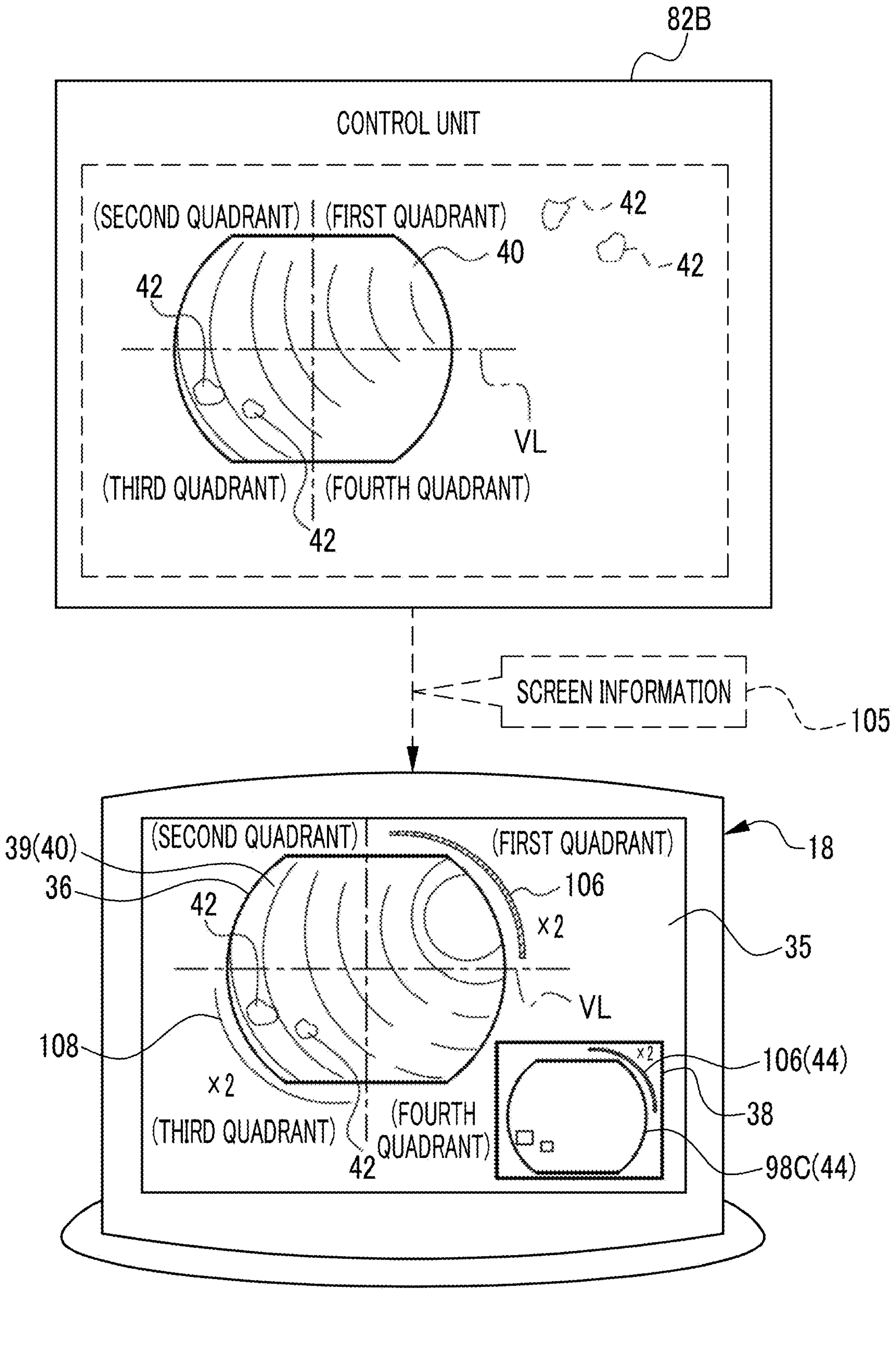
FIG. 21 is a conceptual diagram showing an example of an aspect in which a lesion position map and the visual assist mark are displayed in a second display region.

In the above-described embodiment, a form example is described in which the visual assist mark 106 is displayed on the outside of the first display region 36. However, for example, as shown in FIG. 21, the visual assist mark 106 may be displayed in the second display region 38 as a part of the medical information 44. In this case, the lesion position map 98C may be displayed in the second display region 38 as a part of the medical information 44. In a case where the lesion position map 98C is displayed in the second display region 38, the visual assist mark 106 need only be positioned with respect to the lesion position map 98C also in the second display region 38 in the same manner as the visual assist mark 106 is positioned with respect to the frame 40 in the above-described embodiment. That is, the visual assist mark 106 need only be displayed on the outside of the lesion position map 98C. In addition, the code 107 or the arrow 109 may be displayed in the second display region 38 instead of the visual assist mark 106. In addition, the visual assist mark 108 may be displayed in the second display region 38 in the same manner as shown in FIGS. 16 to 18.

In the example shown in FIG. 21, the lesion position map 98C displayed in the second display region 38 is an example of a "medical image generated based on an image" according to the present disclosure, and the visual assist mark 106 displayed in the second display region 38 is an example of "presence position information" and "out-of-angle-of-view position information" according to the present disclosure.

In the example shown in FIG. 21, a form example is described in which the lesion position map 98C is displayed in the second display region 38, but the frame 40 may be displayed in the second display region 38 instead of the lesion position map 98C. In this case as well, the visual assist mark 106 need only be positioned with respect to the frame 40 in the second display region 38 in the same manner as in the above-described embodiment. In addition, an image in which the frame 40 is processed may be displayed in the second display region 38 instead of the lesion position map 98C. Examples of the image in which the frame 40 is processed include an image in which the frame 40 is deteriorated in image quality (for example, an image with reduced number of pixels and/or gradation), or an image in which the frame 40 is improved in image quality (for example, an image obtained by removing noise or the like from the frame 40 by a non-linear filter using AI or an image newly generated by AI based on the frame 40).

As described above, in the second display region 38, the frame 40 or the image generated based on the frame 40 is displayed and the visual assist mark 106 and/or 108 is displayed in the same manner as in the above-described embodiment, so that the same effects as those in the above-described embodiment can be expected.

In the example shown in FIG. 21, a form example is described in which, in the second display region 38, the lesion position map 98C is displayed as an example of the image generated based on the frame 40, and the visual assist mark 106 and/or 108 is displayed in the same manner as in the above-described embodiment, but this is merely an example. For example, the image generated based on the frame 40 (for example, the lesion position map 98C or the like) may be displayed in the first display region 36, and the visual assist mark 106 and/or 108 may be displayed on the outside of the first display region 36 in the same manner as in the above-described embodiment.

Figure 22:
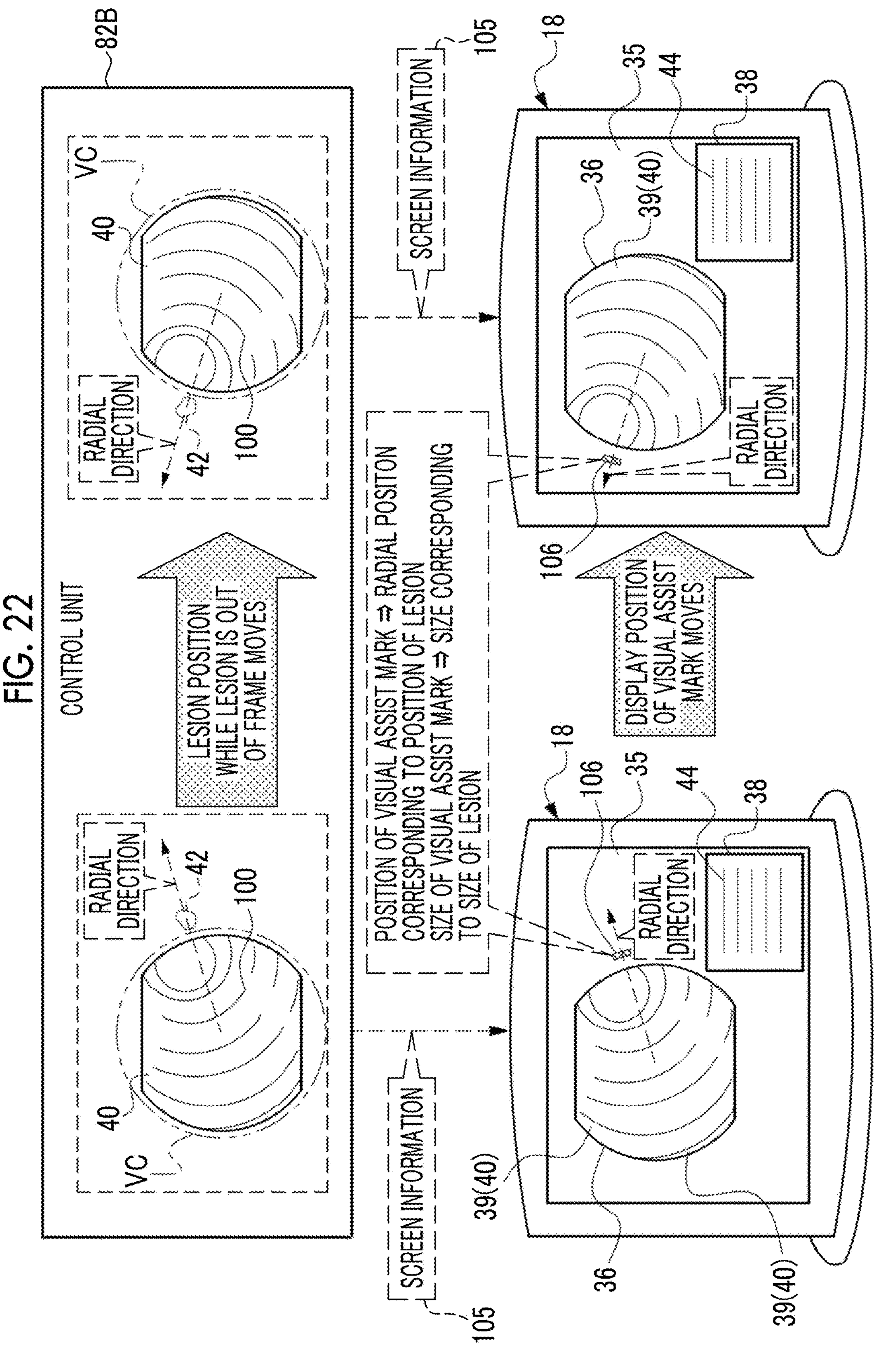
FIG. 22 is a conceptual diagram showing a modification example of the visual assist mark displayed on the screen.

In the above-described embodiment, a form example is described in which the visual assist mark 106 is displayed in units of quadrant, but the present disclosure is not limited to this. For example, as shown in FIG. 22, in a case where the center of the frame 40 is defined as a center of a virtual circle VC, the control unit 82B specifies a radial position corresponding to the position of the lesion 42 that is out of the angle of view (that is, the position of the lesion 42 on a radial direction of the circle VC) based on one or more optical flows 104. In addition, the control unit 82B specifies the size of the lesion 42 that is out of the angle of view based on the geometric characteristic information 98B included in the recognition result 98. Then, the control unit 82B displays the visual assist mark 106 having a size corresponding to the size of the lesion 42 at a radial position on the outside of the first display region 36 in which the frame 40 is displayed, in the screen 35. Even in a case where the lesion 42 that is out of the angle of view is moved, in the same manner, the control unit 82B specifies the radial position and the size of the lesion 42 and displays the visual assist mark 106 having a size corresponding to the size of the lesion 42 at the specified radial position. In this case as well, the display position of the visual assist mark 106 is on the outside of the first display region 36 in which the frame 40 is displayed, but the display position is not limited to units of quadrants as in the above-described embodiment and has a high degree of freedom. Therefore, the doctor 12 can visually accurately ascertain the presence position of the lesion 42 that is out of the angle of view from the display position of the visual assist mark 106.

In the example shown in FIG. 14, a form example is described in which the visual assist mark 106 is displayed on the screen 35 in a display aspect according to the change feature, but the present disclosure is not limited to this. For example, the display aspect of the visual assist mark 106 may be changed according to the feature of the lesion 42. In this case, for example, the control unit 82B specifies the feature of the lesion 42 based on the lesion feature information 98D (see FIG. 5) included in the recognition result 98. Then, the control unit 82B displays the visual assist mark 106 on the screen 35 in a display aspect according to the feature of the lesion 42.

Figure 23:
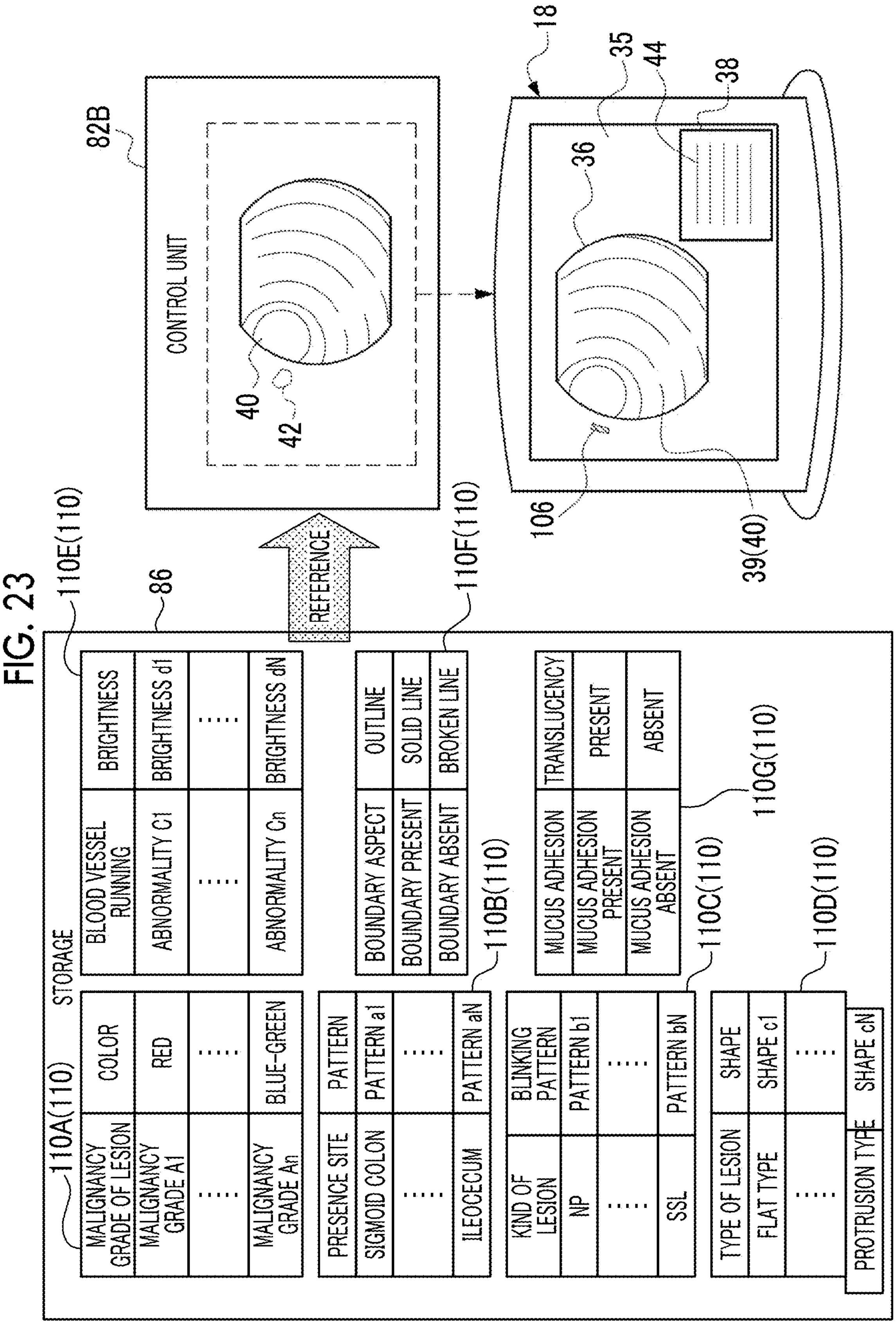
FIG. 23 is a conceptual diagram showing an example of processing contents in a case where a display aspect of the visual assist mark displayed on the screen is changed according to a feature of the lesion.

As shown in FIG. 23 as an example, the display aspect according to the feature of the lesion 42 is defined by a display aspect table 110. The display aspect table 110 is stored in the storage 86. The display aspect table 110 is classified into first to seventh display aspect tables 110A to 110G.

In the first display aspect table 110A, a malignancy grade of the lesion 42 and the display aspect are associated with each other. The display aspect associated with the malignancy grade of the lesion 42 is a color. In the example shown in FIG. 23, different colors are associated with respective malignancy grades of the lesion 42. The control unit 82B specifies the malignancy grade of the lesion 42 from the lesion feature information 98D. Then, the control unit 82B specifies a color corresponding to the malignancy grade specified from the lesion feature information 98D by referring to the first display aspect table 110A, and displays the visual assist mark 106 on the screen 35 in the specified color.

In the second display aspect table 110B, a site where the lesion 42 is present and the display aspect are associated with each other. The display aspect associated with the site where the lesion 42 is present is a pattern included in the visual assist mark 106. In the example shown in FIG. 23, different patterns are associated with respective sites where the lesion 42 is present. The control unit 82B specifies a site where the lesion 42 is present from the lesion feature information 98D. Then, the control unit 82B specifies a pattern corresponding to the specific site from the lesion feature information 98D by referring to the second display aspect table 110B, and displays the visual assist mark 106 including the specified pattern on the screen 35.

In the third display aspect table 110C, a kind of the lesion 42 and the display aspect are associated with each other. The display aspect associated with the kind of the lesion 42 is a blinking pattern in which the visual assist mark 106 blinks. In the example shown in FIG. 23, different blinking patterns are associated with respective kinds of the lesion 42. The control unit 82B specifies the kind of the lesion 42 from the lesion feature information 98D. Then, the control unit 82B specifies a blinking pattern corresponding to the specified type from the lesion feature information 98D by referring to the third display aspect table 110C, and displays the visual assist mark 106 on the screen 35 with the specified blinking pattern. In the fourth display aspect table 110D, a type of the lesion 42 and the display aspect are associated with each other. The display aspect associated with the type of the lesion 42 is a shape of the visual assist mark 106. In the example shown in FIG. 23, different shapes are associated with respective types of the lesion 42. The control unit 82B specifies the type of the lesion 42 from the lesion feature information 98D. Then, the control unit 82B specifies a shape corresponding to the specified type from the lesion feature information 98D by referring to the fourth display aspect table 110D, and displays the visual assist mark 106 formed in the specified shape on the screen 35.

In the fifth display aspect table 110E, a form of the lesion 42 and the display aspect are associated with each other. The display aspect associated with the form of the lesion 42 is a brightness of the visual assist mark 106. In the example shown in FIG. 23, different brightnesses are associated with respective forms of the lesion 42. The control unit 82B specifies the form of the lesion 42 from the lesion feature information 98D. Then, the control unit 82B specifies the brightness corresponding to the specified form from the lesion feature information 98D by referring to the fifth display aspect table 110E, and displays the visual assist mark 106 on the screen 35 at the specified brightness.

In the sixth display aspect table 110F, an aspect of a boundary between the lesion 42 and a periphery of the lesion 42 and the display aspect are associated with each other. The display aspect associated with the aspect of the boundary between the lesion 42 and the periphery of the lesion 42 is an outline of the visual assist mark 106. In the example shown in FIG. 23, different outlines are associated with respective aspects of the boundary between the lesion 42 and the periphery of the lesion 42 (in the example shown in FIG. 23, an aspect in which the boundary between the lesion 42 and the periphery of the lesion 42 is present and an aspect in which the boundary between the lesion 42 and the periphery of the lesion 42 is absent). The control unit 82B specifies an aspect of the boundary between the lesion 42 and the periphery of the lesion 42 from the lesion feature information 98D. Then, the control unit 82B specifies an outline corresponding to the specific aspect from the lesion feature information 98D by referring to the sixth display aspect table 110F, and displays the visual assist mark 106 having the specified outline on the screen 35.

In the seventh display aspect table 110G, an adhesion aspect of mucus of the lesion 42 and the display aspect are associated with each other. The display aspect associated with the adhesion aspect of the mucus of the lesion 42 is the presence or absence of translucency of the visual assist mark 106. In the example shown in FIG. 23, the presence or absence of the translucency is associated with each of the adhesion aspects of the mucus of the lesion 42 (in the example shown in FIG. 23, the presence or absence of adhesion of the mucus). The control unit 82B specifies the adhesion aspect of the mucus of the lesion 42 from the lesion feature information 98D. Then, the control unit 82B specifies the presence or absence of the translucency corresponding to the specified adhesion aspect from the lesion feature information 98D by referring to the seventh display aspect table 110G, and displays the visual assist mark 106 on the screen 35 according to the specified presence or absence of the translucency. In this case, for example, in a case where the adhesion of the mucus of the lesion 42 is “present”, the visual assist mark 106 is displayed on the screen 35 in a translucent manner, and in a case where the adhesion of the mucus of the lesion 42 is “absent”, the visual assist mark 106 is displayed on the screen 35 without being made translucent.

In this way, the display aspect of the visual assist mark 106 is changed according to the feature of the lesion 42 that is out of the angle of view, so that the doctor 12 can visually ascertain the feature of the lesion 42 that is out of the angle of view.

The display aspect shown in FIG. 23 is merely an example, and any display aspect may be adopted as long as the feature of the lesion 42 can be visually specified.

In the above-described embodiment, a form example is described in which the positional relationship between the camera 52 and the lesion 42 is specified based on one or more optical flows 104 by the control unit 82B, but the present disclosure is not limited to this. For example, the positional relationship between the camera 52 and the lesion 42 may be specified based on a detection result by an endoscope insertion shape observation device (commonly known as a colonoscope navigation).

Figure 24:
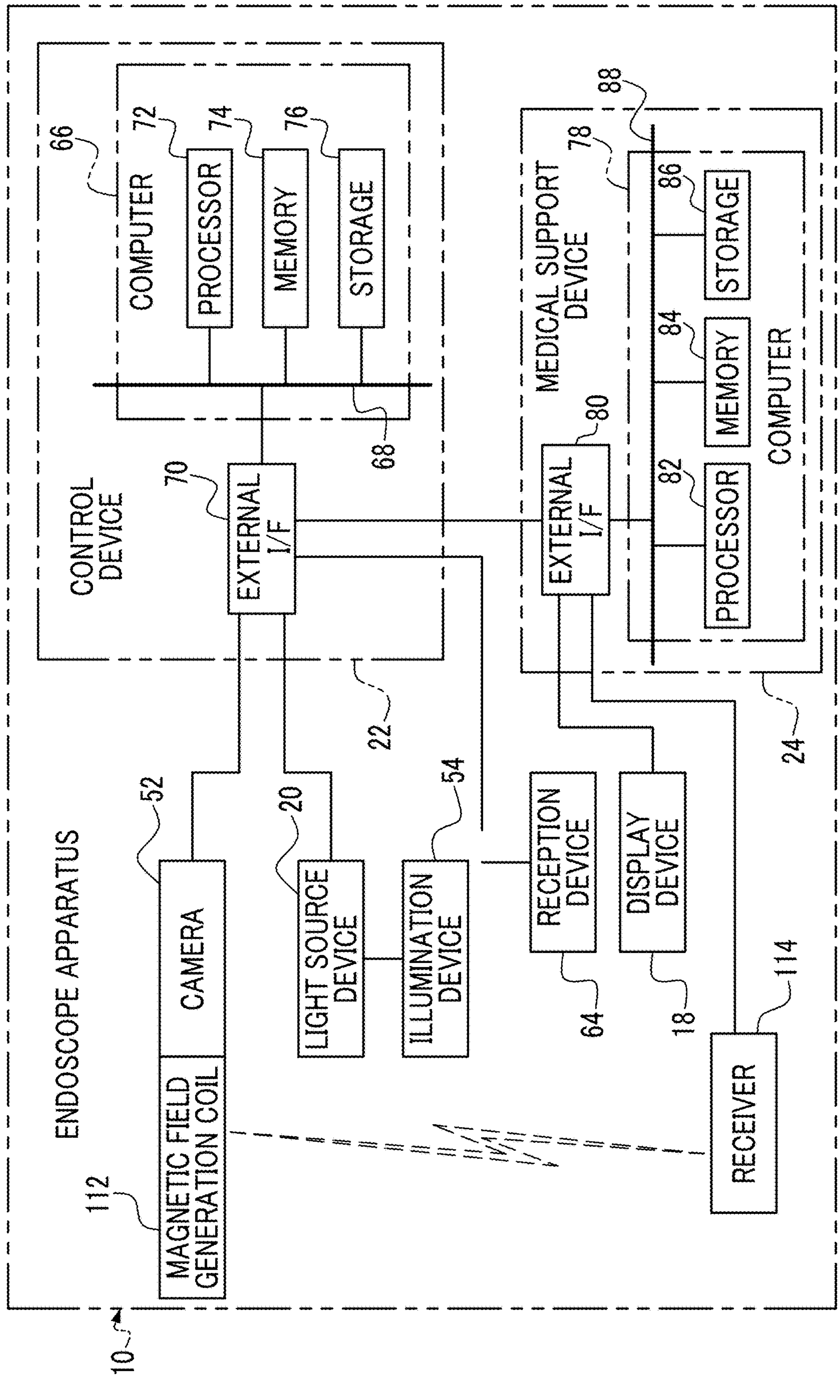
FIG. 24 is a block diagram showing an example of a hardware configuration of the electric system of the endoscope apparatus equipped with an endoscope insertion shape observation device.

In this case, as shown in FIG. 24 as an example, the camera 52 is provided with a magnetic field generation coil 112, and a receiver 114 is connected to the external I/F 80. A magnetic field generated from the magnetic field generation coil 112 is received by the receiver 114. The processor 82 detects a behavior (for example, a position and an orientation) of the camera 52 in the large intestine 28 based on a reception result by the receiver 114, and specifies the positional relationship between the camera 52 and the lesion 42 based on the detection result. In this way, the behavior of the camera 52 in the large intestine 28 is accurately detected, so that the positional relationship between the camera 52 and the lesion 42 can be accurately specified.

The endoscope insertion shape observation device described here is merely an example, and a sensor other than the endoscope insertion shape observation device may be used. For example, the positional relationship between the camera 52 and the lesion 42 in the large intestine 28 may be specified based on a detection result by a sensor capable of detecting the behavior of the camera 52 in the large intestine 28, such as an acceleration sensor, a gyro sensor, and/or a magnetic sensor. The endoscope insertion shape observation device, the acceleration sensor, the gyro sensor, and the magnetic sensor illustrated here are examples of a “sensor” according to the present disclosure.

Figure 25:
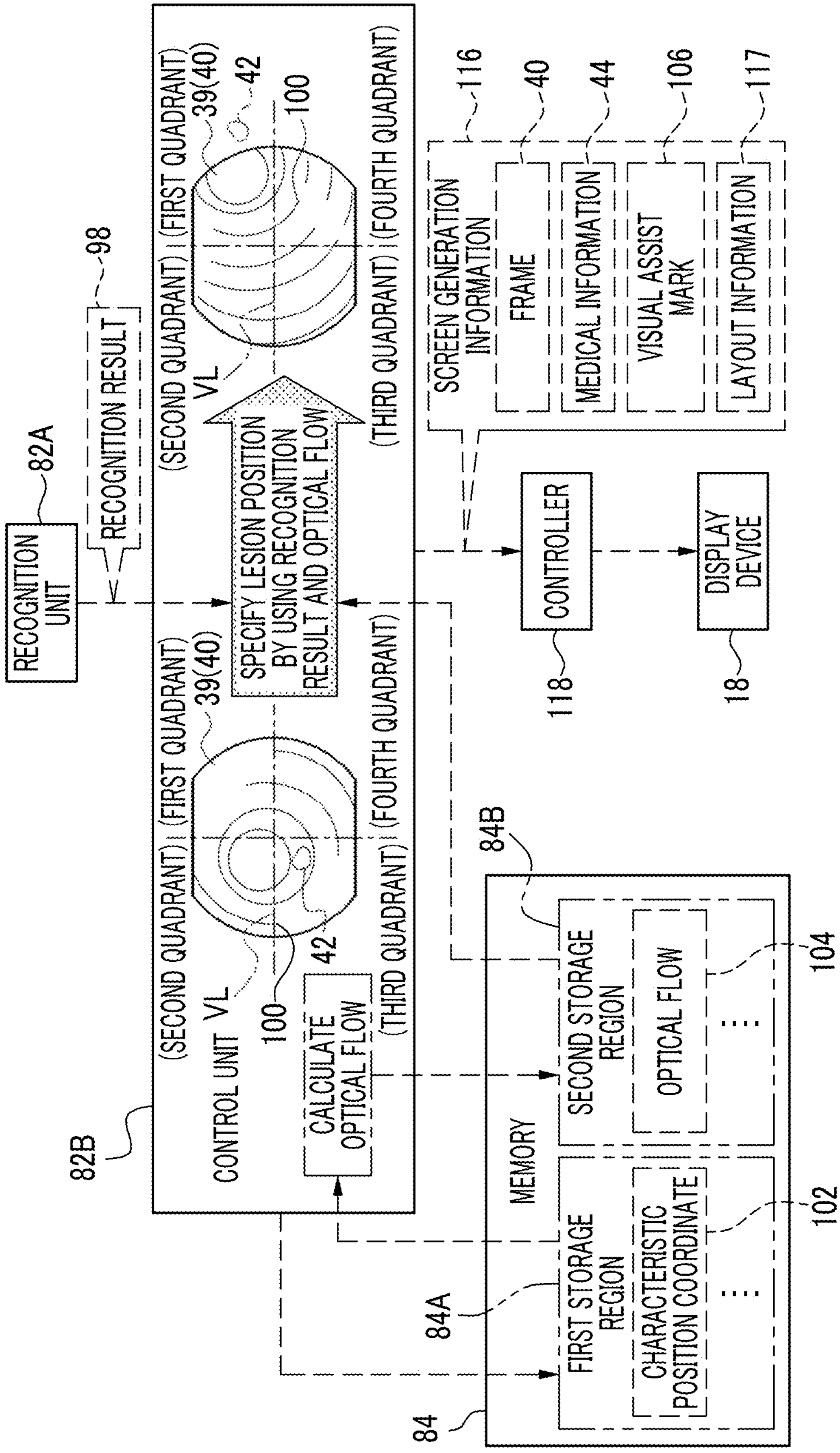
FIG. 25 is a conceptual diagram showing an example of an aspect in which screen generation information is generated and output by the control unit.

In the above-described embodiment, a form example is described in which the screen information 105 is generated by the control unit 82B and output to the display device 18, but the present disclosure is not limited to this. For example, as shown in FIG. 25, the control unit 82B may generate screen generation information 116. The screen generation information 116 includes the frame 40, the medical information 44, the visual assist mark 106, and layout information 117. Here, the screen generation information 116 is an example of “screen generation information” according to the present disclosure, and the layout information 117 is an example of “position indication information” according to the present disclosure.

The layout information 117 is information for defining layouts of the frame 40, the medical information 44, and the visual assist mark 106 in the screen 35. Examples of the information for defining the layout of the frame 40 in the screen 35 include information for indicating a position at which the frame 40 is displayed in the screen 35 (for example, information including coordinates for specifying a position at which the frame 40 is displayed in the screen 35). Examples of the information for defining the layout of the medical information 44 in the screen 35 include information for indicating a position at which the medical information 44 is displayed in the screen 35 (for example, information including coordinates for specifying a position at which the medical information 44 is displayed in the screen 35). Examples of the information for defining the layout of the visual assist mark 106 in the screen 35 include information for indicating a position at which the visual assist mark 106 is displayed in the screen 35 (for example, information including coordinates for specifying a position at which the visual assist mark 106 is displayed in the screen 35).

Here, the position at which the frame 40 is displayed in the screen 35 refers to a position of the first display region 36. In addition, the position at which the medical information 44 is displayed in the screen 35 refers to a position of the second display region 38. In addition, the position at which the visual assist mark 106 is displayed in the screen 35 refers to a position at which the lesion position can be specified on the outside of the first display region 36 in which the frame 40 is displayed.

The position at which the visual assist mark 106 is displayed in the screen 35 is determined by the control unit 82B according to the positional relationship between the camera 52 and the lesion 42, for example, in the same manner as in the above-described embodiment. In a case where the positional relationship between the camera 52 and the lesion 42 is changed, the optical flow 104 is updated, and accordingly, the position at which the visual assist mark 106 is displayed in the screen 35 is updated.

That is, the control unit 82B updates the optical flow 104 according to the change in the positional relationship between the camera 52 and the lesion 42, and updates a part of the information included in the layout information 117 (that is, the information for indicating the position at which the visual assist mark 106 is displayed in the screen 35) according to the updated optical flow 104.

The control unit 82B outputs the screen generation information 116 to a controller 118. Examples of the controller 118 include the control device 22, a tablet terminal, a personal computer, or a server. The display device 18 is connected to the controller 118. The controller 118 generates the screen 35 based on the screen generation information 116 input from the control unit 82B, and displays the screen 35 on the display device 18.

In addition, the control unit 82B updates the screen generation information 116 according to the change in the positional relationship between the camera 52 and the lesion 42. In this case, for example, a position at which the visual assist mark 106 is displayed in the screen 35 is updated according to the change in the positional relationship between the camera 52 and the lesion 42. The display device 18 displays the screen 35 generated by the controller 118 based on the updated screen generation information 116.

As described above, even in a case where the screen generation information 116 including the frame 40, the medical information 44, the visual assist mark 106, and the layout information 117 is generated and output by the control unit 82B, the same effects as those in the above-described embodiment can be expected.

In addition, in the example shown in FIG. 25, a form example is described in which the screen generation information 116 including the frame 40, the medical information 44, the visual assist mark 106, and the layout information 117 is generated and output by the control unit 82B. However, in a case where the visual assist mark 106 is generated by the controller 118, the control unit 82B may generate information including the frame 40, the medical information 44, and the layout information 117 as the screen generation information 116 and output the information to the controller 118.

Here, a form example is described in which the medical information 44 is included in the screen generation information 116, but the medical information 44 may not be included in the screen generation information 116.

In addition, the control unit 82B may divide the screen generation information 116 and output the divided screen generation information 116 to the controller 118. For example, the control unit 82B may output the frame 40, the medical information 44, the visual assist mark 106, and the layout information 117 in a time division manner.

In the above-described embodiment, a form example is described in which the screen information 105 is output to the display device 18, but this is merely an example. The screen information 105 may be output to the storage 76 and/or 86. In addition, the screen information 105 may be output to a processing device (for example, a tablet terminal, a personal computer, and/or a server) existing outside the endoscope apparatus 10. In addition, the screen information 105 may be output to a printer. In this case, for example, the printer prints an image in which the screen 35 indicated by the input screen information 105 is visualized on a medium (for example, paper).

In the above-described embodiment, the lesion 42 is described as an example of an "in-body feature region" according to the present disclosure, but the present disclosure is not limited to this. The medical support process described above is established even in a case where a resection region, a bleeding region, a marking region, an organ, a treatment tool (for example, a hemostatic clip placed in the body), or the like is applied instead of the lesion 42.

In the above-described embodiment, a form example is described in which the frame 40 is input to the recognition unit 82A and the screen information 105 is output from the control unit 82B, but the present disclosure is not limited to this. For example, instruction data (so-called prompt) including the frame 40 may be input to so-called generation AI, and the screen information 105 may be output from the generation AI. Examples of the generation AI include ChatGPT using GPT-4 (Internet search <https://openai.com/gpt-4>).

In addition, instruction data including at least a part (for example, the frame 40 and the visual assist mark 106) of the information included in the screen information 105 may be used as input information for the generation AI. Examples of the information output from the generation AI include information for specifying the positional relationship between the camera 52 and the lesion 42, information for specifying the change in the positional relationship between the camera 52 and the lesion 42, information indicating an operation content of the camera 52, information indicating a content of a medical treatment that is recommended to be performed during the endoscopy, and/or information indicating a content of a medical treatment that is recommended to be performed after the endoscopy. The information output from the generation AI may be stored in various storage regions (for example, the storage 76 and/or 86), displayed on the display device 18 as the medical information 44, printed on a medium by the printer, or output from a speaker as a voice.

In the above-described embodiment, the recognition process 96 using AI in a bounding box method has been described as an example, but this is merely an example. For example, a recognition process using AI in a segmentation method may be performed instead of the recognition process 96 using AI in a bounding box method. In addition, a recognition process in a non-AI method (for example, a template matching method) may be performed instead of the recognition process in an AI method, or a recognition process in which the non-AI method and the AI method are combined may be performed.

In the above-described embodiment, a form example is described in which the medical support process is performed by the computer 78, but the present disclosure is not limited to this. At least some of processing included in the medical support process may be performed by a device provided outside the computer 78. Hereinafter, an example of this case will be described with reference to FIG. 26.

Figure 26:
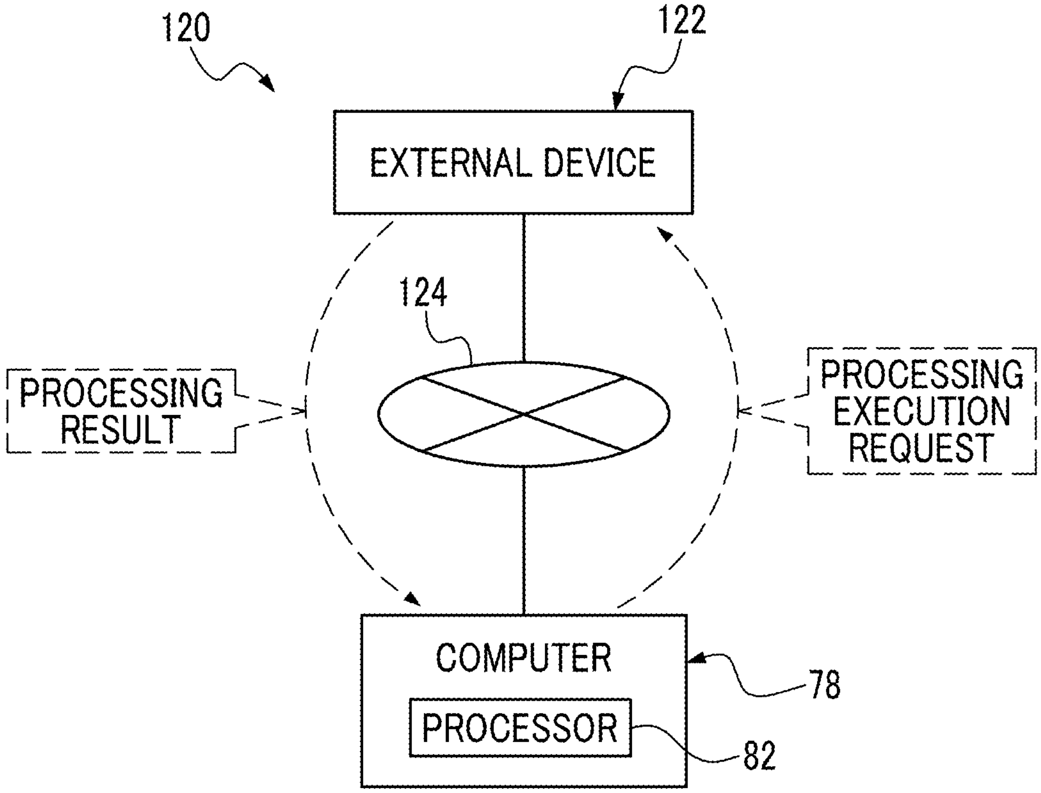
FIG. 26 is a conceptual diagram showing an example of a series of pieces of processing in which a computer gives a processing execution request to an external device via a network, the external device executes processing according to the processing execution request, and the computer receives a processing result from the external device.

FIG. 26 is a conceptual diagram showing an example of a configuration of an endoscope apparatus 120. The endoscope apparatus 120 is an example of an "endoscope apparatus" according to the present disclosure. The endoscope apparatus 120 is different from the endoscope apparatus 10 described in the above-described embodiment in that an external device 122 is provided.

The external device 122 is communicably connected to the computer 78 via a network 124 (for example, a WAN and/or a LAN).

Examples of the external device 122 include at least one server that directly or indirectly performs transmission and reception of data with the computer 78 via the network 124. The external device 122 receives a processing execution instruction given from the processor 82 of the computer 78 via the network 124. Then, the external device 122 executes processing according to the received processing execution instruction and transmits a processing result to the computer 78 via the network 124. In the computer 78, the processor 82 receives the processing result transmitted from the external device 122 via the network 124 and executes a process using the received processing result.

Examples of the processing execution instruction include an instruction for the external device 122 to execute at least a part of the medical support process. First examples of at least a part (that is, processing executed by the external device 122) of the medical support process include the recognition process 96. In this case, the external device 122 executes the recognition process 96 in response to the processing execution instruction given from the processor 82 via the network 124 and transmits the recognition result 98 to the computer 78 via the network 124. In the computer 78, the processor 82 receives the recognition result 98 and executes the same processing as in the above-described embodiment by using the received recognition result 98.

Second examples of at least a part of the medical support process (that is, processing executed by the external device 122) include processing by the control unit 82B. In this case, the external device 122 executes processing by the control unit 82B in response to the processing execution instruction given from the processor 82 via the network 124, and transmits a processing result (for example, the screen information 105) to the computer 78 via the network 124. In the computer 78, the processor 82 receives the processing result and executes the same processing as in the above-described embodiment (for example, the display using the display device 18) by using the received processing result.

For example, the external device 122 is realized by cloud computing. It should be noted that the cloud computing is merely an example, and the external device 122 may be realized by network computing such as fog computing, edge computing, or grid computing. Instead of the server, at least one personal computer or the like may be used as the external device 122. In addition, a computing device having a communication function equipped with a plurality of types of AI functions may be used.

In the above-described embodiment, a form example is described in which the medical support program 90 is stored in the storage 86, but the present disclosure is not limited to this. For example, the medical support program 90 may be stored in a portable computer-readable non-transitory storage medium, such as an SSD or a USB memory. The medical support program 90 stored in the non-transitory storage medium is installed in the computer 78 of the endoscope apparatus 10. The processor 82 executes the medical support process according to the medical support program 90.

In addition, the medical support program 90 may be stored in a storage device of another computer, server, or the like connected to the endoscope apparatus 10 via a network, and the medical support program 90 may be downloaded and installed in the computer 78 in response to a request from the endoscope apparatus 10.

It is not necessary to store all the medical support programs 90 in a storage device of another computer, server device, or the like connected to the endoscope apparatus 10 or to store all the medical support programs 90 in the storage 86, and a part of the medical support programs 90 may be stored.

The following various processors can be used as hardware resources for executing the medical support process. Examples of the processor include a CPU which is a general-purpose processor that executes software, that is, a program, to function as the hardware resource executing the medical support process. In addition, examples of the processor include a dedicated electric circuit which is a processor having a circuit configuration specially designed for executing specific processing, such as an FPGA, a PLD, or an ASIC. A memory is incorporated in or connected to any processor, and any processor executes the medical support process using the memory.

The hardware resource for executing the medical support process may be configured by one of the various processors or by a combination of two or more processors of the same type or different types (for example, a combination of a plurality of FPGAs or a combination of a CPU and an FPGA). Further, the hardware resource for executing the medical support process may be one processor.

As an example of the configuration using one processor, first, there is a form in which one processor is configured by a combination of one or more CPUs and software, and the processor functions as the hardware resource for executing the medical support process. Second, as typified by a SoC or the like, there is a form in which a processor that realizes all functions of a system including a plurality of hardware resources executing the medical support process with one IC chip is used. As described above, the medical support process is realized using one or more of the various processors as the hardware resource.

Further, as a hardware structure of these various processors, more specifically, an electrical circuit in which circuit elements such as semiconductor elements are combined can be used. Further, the above-described medical support process is only an example. Therefore, it is needless to say that unnecessary steps may be deleted, new steps may be added, or a processing order may be changed without departing from the gist of the present disclosure.

The above-described contents and illustrated contents are detailed descriptions of parts related to the present disclosure, and are merely examples of the present disclosure. For example, the above descriptions related to configurations, functions, operations, and advantageous effects are descriptions related to examples of configurations, functions, operations, and advantageous effects of the parts related to the present disclosure. Therefore, it is needless to say that unnecessary parts may be deleted, or new elements may be added or replaced with respect to the above-described contents and illustrated contents without departing from the gist of the present disclosure. In order to avoid complications and easily understand the parts according to the present disclosure, in the above-described contents and illustrated contents, common technical knowledge and the like that do not need to be described to implement the present disclosure are not described.

All documents, patent applications, and technical standards described in the present specification are incorporated in the present specification by reference to the same extent as in a case where each document, patent application, and technical standard are specifically and individually noted to be incorporated by reference.

What is claimed is:

1. A medical support device comprising:

a processor, wherein the processor is configured to:

acquire an image obtained by imaging an inside of a body with a camera; and output screen generation information used for generation of a screen on which the image and presence position information for specifying a presence position of an in-body feature region recognized by executing an object recognition process using the image on an outside of the image are displayed, wherein a display position of the presence position information with respect to the image in the screen is changed according to a change in a positional relationship between the camera and the in-body feature region, wherein the presence position information includes out-of-angle-of-view position information for specifying, on the outside, the presence position in a case where the in-body feature region is out of an angle of view of the camera, and the out-of-angle-of-view position information is displayed on the screen on a condition that the in-body feature region is out of the angle of view, wherein display of the out-of-angle-of-view position information on the screen in a case where a within-angle-of-view time during which the in-body feature region is within the angle of view is less than a certain time is more emphasized than display of the out-of-angle-of-view position information on the screen in a case where the within-angle-of-view time is equal to or longer than the certain time.

2. The medical support device according to claim 1, wherein the change is caused by an operation of the camera and/or a body movement in the inside of the body.

3. The medical support device according to claim 2, wherein the display position is changed according to the change to follow the operation and/or the body movement.

4. The medical support device according to claim 1, wherein a display aspect of the presence position information is changed according to a feature of the change.

5. The medical support device according to claim 4, wherein the feature includes a speed of the change, an amount of the change, and/or a direction of the change.

6. The medical support device according to claim 1, wherein the presence position information includes within-angle-of-view position information for specifying, on the outside, the presence position in a case where the in-body feature region is within the angle of view of the camera, the within-angle-of-view position information is displayed on the screen in a case where the in-body feature region is within the angle of view.

7. The medical support device according to claim 1, wherein a display aspect of the out-of-angle-of-view position information is changed according to a feature of the change.

8. The medical support device according to claim 7, wherein the display aspect includes presence or absence of display, a display intensity, a display time, and/or a speed of changing the display intensity.

9. The medical support device according to claim 1, wherein the in-body feature region is a lesion, and a display aspect of the out-of-angle-of-view position information is changed according to a malignancy grade of the lesion, a site where the lesion is present, a kind of the lesion, a type of the lesion, a form of the lesion, an aspect of a boundary between the lesion and a periphery of the lesion, and/or an adhesion aspect of mucus of the lesion.

10. The medical support device according to claim 1, wherein the out-of-angle-of-view position information is displayed on the screen on a condition that a predetermined time has elapsed after the in-body feature region is out of the angle of view.

11. The medical support device according to claim 1, wherein the out-of-angle-of-view position information is displayed on the screen on the condition that the in-body feature region is out of the angle of view and a degree of the change exceeds a predetermined degree.

12. The medical support device according to claim 1, wherein display of the out-of-angle-of-view position information on the screen in a case where a frequency at which the in-body feature region enters and exits the angle of view exceeds a predetermined frequency within a unit time is more emphasized than display of the out-of-angle-of-view position information on the screen in a case where the frequency is equal to or less than the predetermined frequency.

13. The medical support device according to claim 1, wherein the screen generation information includes the image and position indication information for indicating a position of the presence position information in the screen, and the position indication information is updated according to the change.

14. The medical support device according to claim 13, wherein the screen generation information includes the image, the presence position information, and the position indication information.

15. The medical support device according to claim 1, wherein the object recognition process includes a process of recognizing the in-body feature region based on the image by using AI.

16. The medical support device according to claim 1, wherein the in-body feature region is a lesion.

17. The medical support device according to claim 1, wherein the image is included in a plurality of frames obtained in time series by imaging the inside of the body with the camera, and the processor is configured to:

specify the change based on the plurality of frames; and change the display position according to the specified change.

18. The medical support device according to claim 1, wherein the processor is configured to:

specify the change based on a detection result by a sensor capable of detecting a behavior of the camera in the inside of the body; and change the display position according to the specified change.

19. An endoscope apparatus comprising:

the medical support device according to claim 1; and the camera.

20. A medical support device comprising:

a processor, wherein the processor is configured to:

acquire an image obtained by imaging an inside of a body with a camera; and output screen generation information used for generation of a screen on which a medical image generated based on the image and presence position information for specifying a presence position of an in-body feature region recognized by executing an object recognition process using the image on an outside of the image are displayed, wherein a display position of the presence position information with respect to the medical image in the screen is changed according to a change in a positional relationship between the camera and the in-body feature region, wherein the presence position information includes out-of-angle-of-view position information for specifying, on the outside, the presence position in a case where the in-body feature region is out of an angle of view of the camera, and the out-of-angle-of-view position information is displayed on the screen on a condition that the in-body feature region is out of the angle of view, wherein display of the out-of-angle-of-view position information on the screen in a case where a within-angle-of-view time during which the in-body feature region is within the angle of view is less than a certain time is more emphasized than display of the out-of-angle-of-view position information on the screen in a case where the within-angle-of-view time is equal to or longer than the certain time.

21. A medical support method comprising:

acquiring an image obtained by imaging an inside of a body with a camera; and outputting screen generation information used for generation of a screen on which the image and presence position information for specifying a presence position of an in-body feature region recognized by executing an object recognition process using the image on an outside of the image are displayed, wherein a display position of the presence position information with respect to the image in the screen is changed according to a change in a positional relationship between the camera and the in-body feature region, wherein the presence position information includes out-of-angle-of-view position information for specifying, on the outside, the presence position in a case where the in-body feature region is out of an angle of view of the camera, and the out-of-angle-of-view position information is displayed on the screen on a condition that the in-body feature region is out of the angle of view, wherein display of the out-of-angle-of-view position information on the screen in a case where a within-angle-of-view time during which the in-body feature region is within the angle of view is less than a certain time is more emphasized than display of the out-of-angle-of-view position information on the screen in a case where the within-angle-of-view time is equal to or longer than the certain time.

22. A non-transitory computer-readable storage medium storing a program executable by a computer to execute a medical support process, the medical support process comprising:

acquiring an image obtained by imaging an inside of a body with a camera; and outputting screen generation information used for generation of a screen on which the image and presence position information for specifying a presence position of an in-body feature region recognized by executing an object recognition process using the image on an outside of the image are displayed, wherein a display position of the presence position information with respect to the image in the screen is changed according to a change in a positional relationship between the camera and the in-body feature region, wherein the presence position information includes out-of-angle-of-view position information for specifying, on the outside, the presence position in a case where the in-body feature region is out of an angle of view of the camera, and the out-of-angle-of-view position information is displayed on the screen on a condition that the in-body feature region is out of the angle of view, wherein display of the out-of-angle-of-view position information on the screen in a case where a within-angle-of-view time during which the in-body feature region is within the angle of view is less than a certain time is more emphasized than display of the out-of-angle-of-view position information on the screen in a case where the within-angle-of-view time is equal to or longer than the certain time.

* * * * *